(12) United States Patent
Shah

(10) Patent No.: US 12,016,882 B2
(45) Date of Patent: Jun. 25, 2024

(54) METHOD OF TREATING GLIOBLASTOMA MULTIFORME

(71) Applicant: THE BRIGHAM AND WOMEN'S HOSPITAL, INC., Boston, MA (US)

(72) Inventor: Khalid Shah, Andover, MA (US)

(73) Assignee: THE BRIGHAM AND WOMEN'S HOSPITAL, INC., Boston, MA (US)

( * ) Notice: Subject to any disclaimer, the term of this patent is extended or adjusted under 35 U.S.C. 154(b) by 503 days.

(21) Appl. No.: 16/760,666

(22) PCT Filed: Nov. 20, 2018

(86) PCT No.: PCT/US2018/062011
§ 371 (c)(1),
(2) Date: Apr. 30, 2020

(87) PCT Pub. No.: WO2019/104037
PCT Pub. Date: May 31, 2019

(65) Prior Publication Data
US 2020/0345775 A1    Nov. 5, 2020

Related U.S. Application Data

(60) Provisional application No. 62/590,070, filed on Nov. 22, 2017.

(51) Int. Cl.
| | |
|---|---|
| A61K 35/17 | (2015.01) |
| A61K 9/00 | (2006.01) |
| A61K 35/12 | (2015.01) |
| A61K 35/28 | (2015.01) |
| A61P 35/00 | (2006.01) |
| C07K 14/54 | (2006.01) |
| C07K 14/55 | (2006.01) |
| C07K 14/56 | (2006.01) |
| C07K 14/565 | (2006.01) |
| C07K 14/57 | (2006.01) |
| C07K 14/725 | (2006.01) |
| C07K 16/28 | (2006.01) |
| C07K 16/30 | (2006.01) |

(52) U.S. Cl.
CPC .............. *A61K 35/17* (2013.01); *A61K 35/28* (2013.01); *A61P 35/00* (2018.01); *C07K 14/5409* (2013.01); *C07K 14/5434* (2013.01); *C07K 14/5443* (2013.01); *C07K 14/55* (2013.01); *C07K 14/56* (2013.01); *C07K 14/565* (2013.01); *C07K 14/57* (2013.01); *C07K 14/7051* (2013.01); *C07K 16/2827* (2013.01); *C07K 16/2863* (2013.01); *C07K 16/30* (2013.01); *A61K 9/0019* (2013.01); *A61K 2035/128* (2013.01)

(58) Field of Classification Search
CPC ..... A61K 35/17; A61K 35/28; C07K 14/7051
See application file for complete search history.

(56) References Cited

U.S. PATENT DOCUMENTS

2014/0322275 A1    10/2014    Brogdon et al.

FOREIGN PATENT DOCUMENTS

| WO | 2013158962 A1 | 10/2013 |
| WO | 2016026854 A2 | 2/2016 |
| WO | 2016160918 A1 | 10/2016 |
| WO | 2017167959 A1 | 10/2017 |

OTHER PUBLICATIONS

Cheng et al. "CARs: synthetic immunoreceptors for cancer therapy and beyond." Trends in Molecular Medicine 23(5): 430-450 (2017).
Gao et al. "Therapeutic potential of human mesenchymal stem cells producing IL-12 in a mouse xenograft model of renal cell carcinoma." Cancer Letters 290(2): 157-166 (2010).
Zhang et al., "Engineering CAR-T Cells" Biomarker Research 5:1 1-6 (2017).
International Search Report WO2019104037, In application No. PCT/US2018/62011.

*Primary Examiner* — Elly-Gerald Stoica
(74) *Attorney, Agent, or Firm* — NIXON PEABODY LLP; Mark J. Fitzgerald; Jeanne Jodoin

(57) ABSTRACT

This technology describes novel cell based combined therapeutic modalities that induces mechanism based tumor cell killing in a broad spectrum of sensitive and resistant tumors. These new agents are tumor specific and target a broad spectrum of solid tumors.

1 Claim, 14 Drawing Sheets

Specification includes a Sequence Listing.

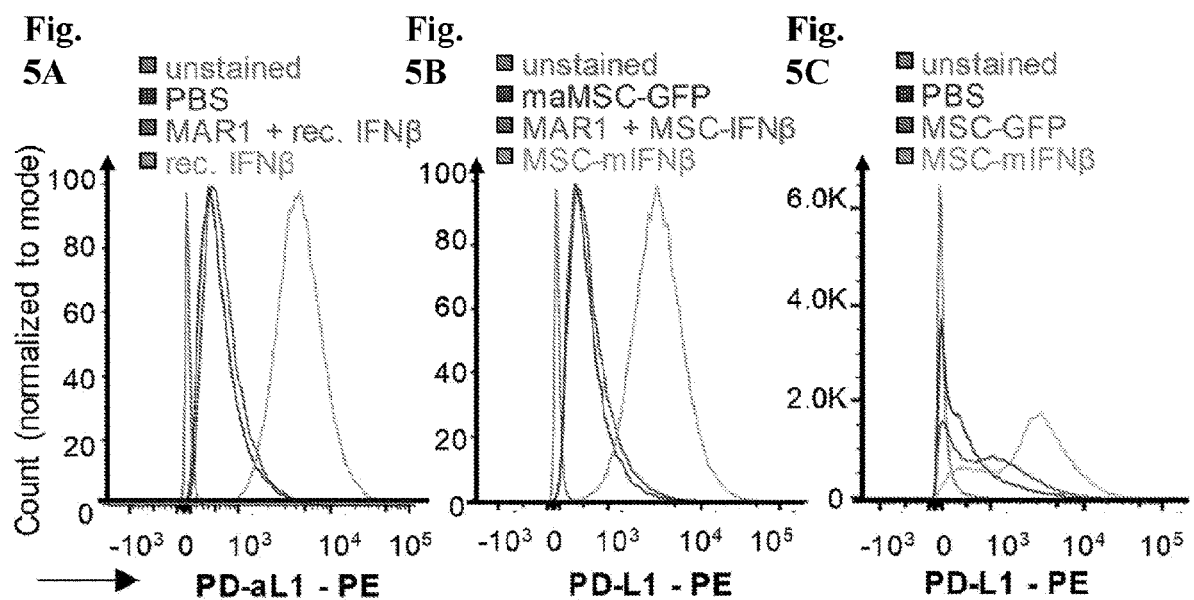

SEQUENCE LISTING

<160> NUMBER OF SEQ ID NOS: 27

<210> SEQ ID NO 1
<211> LENGTH: 290
<212> TYPE: PRT
<213> ORGANISM: Homo sapiens

<400> SEQUENCE: 1

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290

<210> SEQ ID NO 2
<211> LENGTH: 288
<212> TYPE: PRT
<213> ORGANISM: Homo sapiens

<400> SEQUENCE: 2

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp

```
            20                  25                  30
Asn Pro Pro Thr Phe Ser Pro Ala Leu Leu Val Val Thr Glu Gly Asp
         35                  40                  45

Asn Ala Thr Phe Thr Cys Ser Phe Ser Asn Thr Ser Glu Ser Phe Val
 50                  55                  60

Leu Asn Trp Tyr Arg Met Ser Pro Ser Asn Gln Thr Asp Lys Leu Ala
 65                  70                  75                  80

Ala Phe Pro Glu Asp Arg Ser Gln Pro Gly Gln Asp Cys Arg Phe Arg
                 85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

<210> SEQ ID NO 3
<211> LENGTH: 223
<212> TYPE: PRT
<213> ORGANISM: Homo sapiens

<400> SEQUENCE: 3

Met Ala Cys Leu Gly Phe Gln Arg His Lys Ala Gln Leu Asn Leu Ala
 1               5                  10                  15

Thr Arg Thr Trp Pro Cys Thr Leu Leu Phe Phe Leu Leu Phe Ile Pro
                20                  25                  30

Val Phe Cys Lys Ala Met His Val Ala Gln Pro Ala Val Val Leu Ala
            35                  40                  45

Ser Ser Arg Gly Ile Ala Ser Phe Val Cys Glu Tyr Ala Ser Pro Gly
        50                  55                  60

Lys Ala Thr Glu Val Arg Val Thr Val Leu Arg Gln Ala Asp Ser Gln
 65                  70                  75                  80

Val Thr Glu Val Cys Ala Ala Thr Tyr Met Met Gly Asn Glu Leu Thr
                 85                  90                  95

Phe Leu Asp Asp Ser Ile Cys Thr Gly Thr Ser Ser Gly Asn Gln Val
            100                 105                 110
```

```
Asn Leu Thr Ile Gln Gly Leu Arg Ala Met Asp Thr Gly Leu Tyr Ile
            115                 120                 125

Cys Lys Val Glu Leu Met Tyr Pro Pro Pro Tyr Leu Gly Ile Gly
130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
            180                 185                 190

Arg Ser Pro Leu Thr Thr Gly Val Tyr Val Lys Met Pro Pro Thr Glu
            195                 200                 205

Pro Glu Cys Glu Lys Gln Phe Gln Pro Tyr Phe Ile Pro Ile Asn
    210                 215                 220

<210> SEQ ID NO 4
<211> LENGTH: 378
<212> TYPE: PRT
<213> ORGANISM: Homo sapiens

<400> SEQUENCE: 4

Met Ser Lys Glu Pro Leu Ile Leu Trp Leu Met Ile Glu Phe Trp Trp
1               5                   10                  15

Leu Tyr Leu Thr Pro Val Thr Ser Glu Thr Val Val Thr Glu Val Leu
                20                  25                  30

Gly His Arg Val Thr Leu Pro Cys Leu Tyr Ser Ser Trp Ser His Asn
            35                  40                  45

Ser Asn Ser Met Cys Trp Gly Lys Asp Gln Cys Pro Tyr Ser Gly Cys
50                  55                  60

Lys Glu Ala Leu Ile Arg Thr Asp Gly Met Arg Val Thr Ser Arg Lys
65                  70                  75                  80

Ser Ala Lys Tyr Arg Leu Gln Gly Thr Ile Pro Arg Gly Asp Val Ser
                85                  90                  95

Leu Thr Ile Leu Asn Pro Ser Glu Ser Asp Ser Gly Val Tyr Cys Cys
            100                 105                 110

Arg Ile Glu Val Pro Gly Trp Phe Asn Asp Val Lys Ile Asn Val Arg
        115                 120                 125

Leu Asn Leu Gln Arg Ala Ser Thr Thr His Arg Thr Ala Thr Thr
    130                 135                 140

Thr Thr Arg Arg Thr Thr Thr Thr Ser Pro Thr Thr Thr Arg Gln Met
145                 150                 155                 160

Thr Thr Thr Pro Ala Ala Leu Pro Thr Thr Val Val Thr Thr Pro Asp
                165                 170                 175

Leu Thr Thr Gly Thr Pro Leu Gln Met Thr Thr Ile Ala Val Phe Thr
            180                 185                 190

Thr Ala Asn Thr Cys Leu Ser Leu Thr Pro Ser Thr Leu Pro Glu Glu
        195                 200                 205

Ala Thr Gly Leu Leu Thr Pro Glu Pro Ser Lys Glu Gly Pro Ile Leu
    210                 215                 220

Thr Ala Glu Ser Glu Thr Val Leu Pro Ser Asp Ser Trp Ser Ser Val
225                 230                 235                 240

Glu Ser Thr Ser Ala Asp Thr Val Leu Leu Thr Ser Lys Glu Ser Lys
                245                 250                 255

Val Trp Asp Leu Pro Ser Thr Ser His Val Ser Met Trp Lys Thr Ser
            260                 265                 270
```

```
Asp Ser Val Ser Ser Pro Gln Pro Gly Ala Ser Asp Thr Ala Val Pro
            275                 280                 285

Glu Gln Asn Lys Thr Thr Lys Thr Gly Gln Met Asp Gly Ile Pro Met
290                 295                 300

Ser Met Lys Asn Glu Met Pro Ile Ser Gln Leu Leu Met Ile Ile Ala
305                 310                 315                 320

Pro Ser Leu Gly Phe Val Leu Phe Ala Leu Phe Val Ala Phe Leu Leu
                325                 330                 335

Arg Gly Lys Leu Met Glu Thr Tyr Cys Ser Gln Lys His Thr Arg Leu
                340                 345                 350

Asp Tyr Ile Gly Asp Ser Lys Asn Val Leu Asn Asp Val Gln His Gly
                355                 360                 365

Arg Glu Asp Glu Asp Gly Leu Phe Thr Leu
                370                 375

<210> SEQ ID NO 5
<211> LENGTH: 525
<212> TYPE: PRT
<213> ORGANISM: Homo sapiens

<400> SEQUENCE: 5

Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
                20                  25                  30

Trp Ala Gln Glu Gly Ala Pro Ala Gln Leu Pro Cys Ser Pro Thr Ile
            35                  40                  45

Pro Leu Gln Asp Leu Ser Leu Leu Arg Arg Ala Gly Val Thr Trp Gln
        50                  55                  60

His Gln Pro Asp Ser Gly Pro Pro Ala Ala Ala Pro Gly His Pro Leu
65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly
            100                 105                 110

Arg Leu Pro Leu Gln Pro Arg Val Gln Leu Asp Glu Arg Gly Arg Gln
        115                 120                 125

Arg Gly Asp Phe Ser Leu Trp Leu Arg Pro Ala Arg Arg Ala Asp Ala
130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
        195                 200                 205

Gly Arg Val Pro Val Arg Glu Ser Pro His His His Leu Ala Glu Ser
210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
```

```
                    260                 265                 270
Gly Ala Gly Ser Arg Val Gly Leu Pro Cys Arg Leu Pro Ala Gly Val
            275                 280                 285

Gly Thr Arg Ser Phe Leu Thr Ala Lys Trp Thr Pro Gly Gly Gly
            290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
            355                 360                 365

Cys Glu Val Thr Pro Val Ser Gly Gln Glu Arg Phe Val Trp Ser Ser
370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
                405                 410                 415

Gly Glu Arg Leu Leu Gly Ala Ala Val Tyr Phe Thr Glu Leu Ser Ser
            420                 425                 430

Pro Gly Ala Gln Arg Ser Gly Arg Ala Pro Gly Ala Leu Pro Ala Gly
            435                 440                 445

His Leu Leu Leu Phe Leu Ile Leu Gly Val Leu Ser Leu Leu Leu Leu
450                 455                 460

Val Thr Gly Ala Phe Gly Phe His Leu Trp Arg Arg Gln Trp Arg Pro
465                 470                 475                 480

Arg Arg Phe Ser Ala Leu Glu Gln Gly Ile His Pro Pro Gln Ala Gln
                485                 490                 495

Ser Lys Ile Glu Glu Leu Glu Gln Glu Pro Glu Pro Glu Pro Glu Pro
            500                 505                 510

Glu Pro Glu Pro Glu Pro Glu Pro Glu Gln Leu
            515                 520                 525

<210> SEQ ID NO 6
<211> LENGTH: 244
<212> TYPE: PRT
<213> ORGANISM: Homo sapiens

<400> SEQUENCE: 6

Met Arg Trp Cys Leu Leu Leu Ile Trp Ala Gln Gly Leu Arg Gln Ala
1               5                   10                  15

Pro Leu Ala Ser Gly Met Met Thr Gly Thr Ile Glu Thr Thr Gly Asn
            20                  25                  30

Ile Ser Ala Glu Lys Gly Gly Ser Ile Ile Leu Gln Cys His Leu Ser
            35                  40                  45

Ser Thr Thr Ala Gln Val Thr Gln Val Asn Trp Glu Gln Gln Asp Gln
            50                  55                  60

Leu Leu Ala Ile Cys Asn Ala Asp Leu Gly Trp His Ile Ser Pro Ser
65                  70                  75                  80

Phe Lys Asp Arg Val Ala Pro Gly Pro Gly Leu Gly Leu Thr Leu Gln
                85                  90                  95

Ser Leu Thr Val Asn Asp Thr Gly Glu Tyr Phe Cys Ile Tyr His Thr
            100                 105                 110
```

Tyr Pro Asp Gly Thr Tyr Thr Gly Arg Ile Phe Leu Glu Val Leu Glu
            115                 120                 125

Ser Ser Val Ala Glu His Gly Ala Arg Phe Gln Ile Pro Leu Leu Gly
130                 135                 140

Ala Met Ala Ala Thr Leu Val Val Ile Cys Thr Ala Val Ile Val Val
145                 150                 155                 160

Val Ala Leu Thr Arg Lys Lys Ala Leu Arg Ile His Ser Val Glu
                165                 170                 175

Gly Asp Leu Arg Arg Lys Ser Ala Gly Gln Glu Glu Trp Ser Pro Ser
                180                 185                 190

Ala Pro Ser Pro Pro Gly Ser Cys Val Gln Ala Glu Ala Pro Ala
                195                 200                 205

Gly Leu Cys Gly Glu Gln Arg Gly Glu Asp Cys Ala Glu Leu His Asp
210                 215                 220

Tyr Phe Asn Val Leu Ser Tyr Arg Ser Leu Gly Asn Cys Ser Phe Phe
225                 230                 235                 240

Thr Glu Thr Gly

<210> SEQ ID NO 7
<211> LENGTH: 241
<212> TYPE: PRT
<213> ORGANISM: Mus musculus

<400> SEQUENCE: 7

Met His Gly Trp Leu Leu Val Trp Val Gln Gly Leu Ile Gln Ala
1               5                   10                  15

Ala Phe Leu Ala Thr Gly Ala Thr Ala Gly Thr Ile Asp Thr Lys Arg
                20                  25                  30

Asn Ile Ser Ala Glu Glu Gly Gly Ser Val Ile Leu Gln Cys His Phe
                35                  40                  45

Ser Ser Asp Thr Ala Glu Val Thr Gln Val Asp Trp Lys Gln Gln Asp
50                  55                  60

Gln Leu Leu Ala Ile Tyr Ser Val Asp Leu Gly Trp His Val Ala Ser
65                  70                  75                  80

Val Phe Ser Asp Arg Val Val Pro Gly Pro Ser Leu Gly Leu Thr Phe
                85                  90                  95

Gln Ser Leu Thr Met Asn Asp Thr Gly Glu Tyr Phe Cys Thr Tyr His
                100                 105                 110

Thr Tyr Pro Gly Gly Ile Tyr Lys Gly Arg Ile Phe Leu Lys Val Gln
            115                 120                 125

Glu Ser Ser Val Ala Gln Phe Gln Thr Ala Pro Leu Gly Gly Thr Met
130                 135                 140

Ala Ala Val Leu Gly Leu Ile Cys Leu Met Val Thr Gly Val Thr Val
145                 150                 155                 160

Leu Ala Arg Lys Lys Ser Ile Arg Met His Ser Ile Glu Ser Gly Leu
                165                 170                 175

Gly Arg Thr Glu Ala Glu Pro Gln Glu Trp Asn Leu Arg Ser Leu Ser
                180                 185                 190

Ser Pro Gly Ser Pro Val Gln Thr Gln Thr Ala Pro Ala Gly Pro Cys
                195                 200                 205

Gly Glu Gln Ala Glu Asp Asp Tyr Ala Asp Pro Gln Glu Tyr Phe Asn
210                 215                 220

Val Leu Ser Tyr Arg Ser Leu Glu Ser Phe Ile Ala Val Ser Lys Thr
225                 230                 235                 240

Gly

```
<210> SEQ ID NO 8
<211> LENGTH: 223
<212> TYPE: PRT
<213> ORGANISM: Mus musculus

<400> SEQUENCE: 8
```

Met Ala Cys Leu Gly Leu Arg Arg Tyr Lys Ala Gln Leu Gln Leu Pro
1               5                   10                  15

Ser Arg Thr Trp Pro Phe Val Ala Leu Thr Leu Leu Phe Ile Pro
            20                  25                  30

Val Phe Ser Glu Ala Ile Gln Val Thr Gln Pro Ser Val Leu Ala
        35                  40                  45

Ser Ser His Gly Val Ala Ser Phe Pro Cys Glu Tyr Ser Pro Ser His
    50                  55                  60

Asn Thr Asp Glu Val Arg Val Thr Val Leu Arg Gln Thr Asn Asp Gln
65                  70                  75                  80

Met Thr Glu Val Cys Ala Thr Thr Phe Thr Glu Lys Asn Thr Val Gly
                85                  90                  95

Phe Leu Asp Tyr Pro Phe Cys Ser Gly Thr Phe Asn Glu Ser Arg Val
            100                 105                 110

Asn Leu Thr Ile Gln Gly Leu Arg Ala Val Asp Thr Gly Leu Tyr Leu
        115                 120                 125

Cys Lys Val Glu Leu Met Tyr Pro Pro Tyr Phe Val Gly Met Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Val Ala Val Ser Leu Gly Leu Phe Phe
                165                 170                 175

Tyr Ser Phe Leu Val Thr Ala Val Ser Leu Ser Lys Met Leu Lys Lys
            180                 185                 190

Arg Ser Pro Leu Thr Thr Gly Val Tyr Val Lys Met Pro Pro Thr Glu
        195                 200                 205

Pro Glu Cys Glu Lys Gln Phe Gln Pro Tyr Phe Ile Pro Ile Asn
    210                 215                 220

```
<210> SEQ ID NO 9
<211> LENGTH: 301
<212> TYPE: PRT
<213> ORGANISM: Homo sapiens

<400> SEQUENCE: 9
```

Met Phe Ser His Leu Pro Phe Asp Cys Val Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
        35                  40                  45

Val Pro Val Cys Trp Gly Lys Gly Ala Cys Pro Val Phe Glu Cys Gly
    50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile

```
                    100                 105                 110
Gln Ile Pro Gly Ile Met Asn Asp Glu Lys Phe Asn Leu Lys Leu Val
                115                 120                 125

Ile Lys Pro Ala Lys Val Thr Pro Ala Pro Thr Arg Gln Arg Asp Phe
            130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Ile Gly Ile Tyr Ile Gly Ala Gly
                195                 200                 205

Ile Cys Ala Gly Leu Ala Leu Ala Leu Ile Phe Gly Ala Leu Ile Phe
            210                 215                 220

Lys Trp Tyr Ser His Ser Lys Glu Lys Ile Gln Asn Leu Ser Leu Ile
225                 230                 235                 240

Ser Leu Ala Asn Leu Pro Pro Ser Gly Leu Ala Asn Ala Val Ala Glu
                245                 250                 255

Gly Ile Arg Ser Glu Glu Asn Ile Tyr Thr Ile Glu Glu Asn Val Tyr
            260                 265                 270

Glu Val Glu Glu Pro Asn Glu Tyr Tyr Cys Tyr Val Ser Ser Arg Gln
                275                 280                 285

Gln Pro Ser Gln Pro Leu Gly Cys Arg Phe Ala Met Pro
            290                 295                 300

<210> SEQ ID NO 10
<211> LENGTH: 281
<212> TYPE: PRT
<213> ORGANISM: Mus musculus

<400> SEQUENCE: 10

Met Phe Ser Gly Leu Thr Leu Asn Cys Val Leu Leu Leu Leu Gln Leu
1               5                   10                  15

Leu Leu Ala Arg Ser Leu Glu Asn Ala Tyr Val Phe Glu Val Gly Lys
                20                  25                  30

Asn Ala Tyr Leu Pro Cys Ser Tyr Thr Leu Ser Thr Pro Gly Ala Leu
            35                  40                  45

Val Pro Met Cys Trp Gly Lys Gly Phe Cys Pro Trp Ser Gln Cys Thr
        50                  55                  60

Asn Glu Leu Leu Arg Thr Asp Glu Arg Asn Val Thr Tyr Gln Lys Ser
65                  70                  75                  80

Ser Arg Tyr Gln Leu Lys Gly Asp Leu Asn Lys Gly Asp Val Ser Leu
                85                  90                  95

Ile Ile Lys Asn Val Thr Leu Asp Asp His Gly Thr Tyr Cys Cys Arg
            100                 105                 110

Ile Gln Phe Pro Gly Leu Met Asn Asp Lys Lys Leu Glu Leu Lys Leu
        115                 120                 125

Asp Ile Lys Ala Ala Lys Val Thr Pro Ala Gln Thr Ala His Gly Asp
    130                 135                 140

Ser Thr Thr Ala Ser Pro Arg Thr Leu Thr Thr Glu Arg Asn Gly Ser
145                 150                 155                 160

Glu Thr Gln Thr Leu Val Thr Leu His Asn Asn Gly Thr Lys Ile
                165                 170                 175
```

```
Ser Thr Trp Ala Asp Glu Ile Lys Asp Ser Gly Glu Thr Ile Arg Thr
            180                 185                 190

Ala Ile His Ile Gly Val Gly Val Ser Ala Gly Leu Thr Leu Ala Leu
        195                 200                 205

Ile Ile Gly Val Leu Ile Leu Lys Trp Tyr Ser Cys Lys Lys Lys Lys
    210                 215                 220

Leu Ser Ser Leu Ser Leu Ile Thr Leu Ala Asn Leu Pro Pro Gly Gly
225                 230                 235                 240

Leu Ala Asn Ala Gly Ala Val Arg Ile Arg Ser Glu Glu Asn Ile Tyr
                245                 250                 255

Thr Ile Glu Glu Asn Val Tyr Glu Val Glu Asn Ser Asn Glu Tyr Tyr
            260                 265                 270

Cys Tyr Val Asn Ser Gln Gln Pro Ser
        275                 280

<210> SEQ ID NO 11
<211> LENGTH: 521
<212> TYPE: PRT
<213> ORGANISM: Mus musculus

<400> SEQUENCE: 11

Met Arg Glu Asp Leu Leu Gly Phe Leu Leu Gly Leu Leu Trp
1               5                   10                  15

Glu Ala Pro Val Val Ser Ser Gly Pro Gly Lys Glu Leu Pro Val Val
                20                  25                  30

Trp Ala Gln Glu Gly Ala Pro Val His Leu Pro Cys Ser Leu Lys Ser
            35                  40                  45

Pro Asn Leu Asp Pro Asn Phe Leu Arg Arg Gly Gly Val Ile Trp Gln
    50                  55                  60

His Gln Pro Asp Ser Gly Gln Pro Thr Pro Ile Pro Ala Leu Asp Leu
65                  70                  75                  80

His Gln Gly Met Pro Ser Pro Arg Gln Pro Ala Pro Gly Arg Tyr Thr
                85                  90                  95

Val Leu Ser Val Ala Pro Gly Gly Leu Arg Ser Gly Arg Gln Pro Leu
                100                 105                 110

His Pro His Val Gln Leu Glu Glu Arg Gly Leu Gln Arg Gly Asp Phe
            115                 120                 125

Ser Leu Trp Leu Arg Pro Ala Leu Arg Thr Asp Ala Gly Glu Tyr His
    130                 135                 140

Ala Thr Val Arg Leu Pro Asn Arg Ala Leu Ser Cys Ser Leu Arg Leu
145                 150                 155                 160

Arg Val Gly Gln Ala Ser Met Ile Ala Ser Pro Ser Gly Val Leu Lys
                165                 170                 175

Leu Ser Asp Trp Val Leu Leu Asn Cys Ser Phe Ser Arg Pro Asp Arg
            180                 185                 190

Pro Val Ser Val His Trp Phe Gln Gly Gln Asn Arg Val Pro Val Tyr
        195                 200                 205

Asn Ser Pro Arg His Phe Leu Ala Glu Thr Phe Leu Leu Leu Pro Gln
    210                 215                 220

Val Ser Pro Leu Asp Ser Gly Thr Trp Gly Cys Val Leu Thr Tyr Arg
225                 230                 235                 240

Asp Gly Phe Asn Val Ser Ile Thr Tyr Asn Leu Lys Val Leu Gly Leu
                245                 250                 255

Glu Pro Val Ala Pro Leu Thr Val Tyr Ala Ala Glu Gly Ser Arg Val
            260                 265                 270
```

Glu Leu Pro Cys His Leu Pro Pro Gly Val Gly Thr Pro Ser Leu Leu
            275                 280                 285

Ile Ala Lys Trp Thr Pro Pro Gly Gly Pro Glu Leu Pro Val Ala
        290                 295                 300

Gly Lys Ser Gly Asn Phe Thr Leu His Leu Glu Ala Val Gly Leu Ala
305                 310                 315                 320

Gln Ala Gly Thr Tyr Thr Cys Ser Ile His Leu Gln Gly Gln Gln Leu
                325                 330                 335

Asn Ala Thr Val Thr Leu Ala Val Ile Thr Val Thr Pro Lys Ser Phe
                340                 345                 350

Gly Leu Pro Gly Ser Arg Gly Lys Leu Leu Cys Glu Val Thr Pro Ala
            355                 360                 365

Ser Gly Lys Glu Arg Phe Val Trp Arg Pro Leu Asn Asn Leu Ser Arg
        370                 375                 380

Ser Cys Pro Gly Pro Val Leu Glu Ile Gln Glu Ala Arg Leu Leu Ala
385                 390                 395                 400

Glu Arg Trp Gln Cys Gln Leu Tyr Glu Gly Gln Arg Leu Leu Gly Ala
                405                 410                 415

Thr Val Tyr Ala Ala Glu Ser Ser Ser Gly Ala His Ser Ala Arg Arg
                420                 425                 430

Ile Ser Gly Asp Leu Lys Gly Gly His Leu Val Leu Val Leu Ile Leu
            435                 440                 445

Gly Ala Leu Ser Leu Phe Leu Leu Val Ala Gly Ala Phe Gly Phe His
450                 455                 460

Trp Trp Arg Lys Gln Leu Leu Leu Arg Arg Phe Ser Ala Leu Glu His
465                 470                 475                 480

Gly Ile Gln Pro Phe Pro Ala Gln Arg Lys Ile Glu Glu Leu Glu Arg
                485                 490                 495

Glu Leu Glu Thr Glu Met Gly Gln Glu Pro Glu Pro Glu Pro Glu Pro
            500                 505                 510

Gln Leu Glu Pro Glu Pro Arg Gln Leu
            515                 520

<210> SEQ ID NO 12
<211> LENGTH: 176
<212> TYPE: PRT
<213> ORGANISM: Homo sapiens

<400> SEQUENCE: 12

Met Arg Ile Phe Ala Val Phe Ile Phe Met Thr Tyr Trp His Leu Leu
1               5                   10                  15

Asn Ala Pro Tyr Asn Lys Ile Asn Gln Arg Ile Leu Val Val Asp Pro
            20                  25                  30

Val Thr Ser Glu His Glu Leu Thr Cys Gln Ala Glu Gly Tyr Pro Lys
        35                  40                  45

Ala Glu Val Ile Trp Thr Ser Ser Asp His Gln Val Leu Ser Gly Lys
    50                  55                  60

Thr Thr Thr Thr Asn Ser Lys Arg Glu Glu Lys Leu Phe Asn Val Thr
65                  70                  75                  80

Ser Thr Leu Arg Ile Asn Thr Thr Asn Glu Ile Phe Tyr Cys Thr
                85                  90                  95

Phe Arg Arg Leu Asp Pro Glu Glu Asn His Thr Ala Glu Leu Val Ile
                100                 105                 110

Pro Glu Leu Pro Leu Ala His Pro Pro Asn Glu Arg Thr His Leu Val

```
                115                 120                 125
Ile Leu Gly Ala Ile Leu Leu Cys Leu Gly Val Ala Leu Thr Phe Ile
            130                 135                 140

Phe Arg Leu Arg Lys Gly Arg Met Met Asp Val Lys Lys Cys Gly Ile
145                 150                 155                 160

Gln Asp Thr Asn Ser Lys Lys Gln Ser Asp Thr His Leu Glu Glu Thr
                165                 170                 175

<210> SEQ ID NO 13
<211> LENGTH: 245
<212> TYPE: PRT
<213> ORGANISM: Homo sapiens

<400> SEQUENCE: 13

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Gly Asn Ile Leu Asn Val Ser Ile Lys Ile Cys Leu Thr
225                 230                 235                 240

Leu Ser Pro Ser Thr
                245

<210> SEQ ID NO 14
<211> LENGTH: 290
<212> TYPE: PRT
<213> ORGANISM: Mus musculus

<400> SEQUENCE: 14

Met Arg Ile Phe Ala Gly Ile Ile Phe Thr Ala Cys Cys His Leu Leu
1               5                   10                  15

Arg Ala Phe Thr Ile Thr Ala Pro Lys Asp Leu Tyr Val Val Glu Tyr
```

```
            20                  25                  30
Gly Ser Asn Val Thr Met Glu Cys Arg Phe Pro Val Glu Arg Glu Leu
        35                  40                  45

Asp Leu Leu Ala Leu Val Val Tyr Trp Glu Lys Glu Asp Glu Gln Val
    50                  55                  60

Ile Gln Phe Val Ala Gly Glu Glu Asp Leu Lys Pro Gln His Ser Asn
65                  70                  75                  80

Phe Arg Gly Arg Ala Ser Leu Pro Lys Asp Gln Leu Leu Lys Gly Asn
                85                  90                  95

Ala Ala Leu Gln Ile Thr Asp Val Lys Leu Gln Asp Ala Gly Val Tyr
            100                 105                 110

Cys Cys Ile Ile Ser Tyr Gly Gly Ala Asp Tyr Lys Arg Ile Thr Leu
        115                 120                 125

Lys Val Asn Ala Pro Tyr Arg Lys Ile Asn Gln Arg Ile Ser Val Asp
    130                 135                 140

Pro Ala Thr Ser Glu His Glu Leu Ile Cys Gln Ala Glu Gly Tyr Pro
145                 150                 155                 160

Glu Ala Glu Val Ile Trp Thr Asn Ser Asp His Gln Pro Val Ser Gly
                165                 170                 175

Lys Arg Ser Val Thr Thr Ser Arg Thr Glu Gly Met Leu Leu Asn Val
            180                 185                 190

Thr Ser Ser Leu Arg Val Asn Ala Thr Ala Asn Asp Val Phe Tyr Cys
        195                 200                 205

Thr Phe Trp Arg Ser Gln Pro Gly Gln Asn His Thr Ala Glu Leu Ile
    210                 215                 220

Ile Pro Glu Leu Pro Ala Thr His Pro Pro Gln Asn Arg Thr His Trp
225                 230                 235                 240

Val Leu Leu Gly Ser Ile Leu Leu Phe Leu Ile Val Val Ser Thr Val
                245                 250                 255

Leu Leu Phe Leu Arg Lys Gln Val Arg Met Leu Asp Val Glu Lys Cys
            260                 265                 270

Gly Val Glu Asp Thr Ser Ser Lys Asn Arg Asn Asp Thr Gln Phe Glu
        275                 280                 285

Glu Thr
    290

<210> SEQ ID NO 15
<211> LENGTH: 288
<212> TYPE: PRT
<213> ORGANISM: Mus musculus

<400> SEQUENCE: 15

Met Trp Val Arg Gln Val Pro Trp Ser Phe Thr Trp Ala Val Leu Gln
1               5                   10                  15

Leu Ser Trp Gln Ser Gly Trp Leu Leu Glu Val Pro Asn Gly Pro Trp
            20                  25                  30

Arg Ser Leu Thr Phe Tyr Pro Ala Trp Leu Thr Val Ser Glu Gly Ala
        35                  40                  45

Asn Ala Thr Phe Thr Cys Ser Leu Ser Asn Trp Ser Glu Asp Leu Met
    50                  55                  60

Leu Asn Trp Asn Arg Leu Ser Pro Ser Asn Gln Thr Glu Lys Gln Ala
65                  70                  75                  80

Ala Phe Cys Asn Gly Leu Ser Gln Pro Val Gln Asp Ala Arg Phe Gln
                85                  90                  95
```

Ile Ile Gln Leu Pro Asn Arg His Asp Phe His Met Asn Ile Leu Asp
              100                 105                 110

Thr Arg Arg Asn Asp Ser Gly Ile Tyr Leu Cys Gly Ala Ile Ser Leu
        115                 120                 125

His Pro Lys Ala Lys Ile Glu Glu Ser Pro Gly Ala Glu Leu Val Val
    130                 135                 140

Thr Glu Arg Ile Leu Glu Thr Ser Thr Arg Tyr Pro Ser Pro Ser Pro
145                 150                 155                 160

Lys Pro Glu Gly Arg Phe Gln Gly Met Val Ile Gly Ile Met Ser Ala
                165                 170                 175

Leu Val Gly Ile Pro Val Leu Leu Leu Ala Trp Ala Leu Ala Val
            180                 185                 190

Phe Cys Ser Thr Ser Met Ser Glu Ala Arg Gly Ala Gly Ser Lys Asp
        195                 200                 205

Asp Thr Leu Lys Glu Glu Pro Ser Ala Ala Pro Val Pro Ser Val Ala
    210                 215                 220

Tyr Glu Glu Leu Asp Phe Gln Gly Arg Gly Lys Thr Pro Glu Leu Pro
225                 230                 235                 240

Thr Ala Cys Val His Thr Glu Tyr Ala Thr Ile Val Phe Thr Glu Gly
                245                 250                 255

Leu Gly Ala Ser Ala Met Gly Arg Arg Gly Ser Ala Asp Gly Leu Gln
            260                 265                 270

Gly Pro Arg Pro Pro Arg His Glu Asp Gly His Cys Ser Trp Pro Leu
        275                 280                 285

<210> SEQ ID NO 16
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 17
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro

```
                    85                  90                  95
Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
                195                 200                 205

Ser Phe Asn Arg Gly Glu Cys
                210                 215
```

<210> SEQ ID NO 18
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

```
Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Tyr Met Tyr Trp Val Arg Gln Ala Pro Gly Gln Gly Leu Glu Trp Met
            35                  40                  45

Gly Gly Ile Asn Pro Ser Asn Gly Gly Thr Asn Phe Asn Glu Lys Phe
50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Lys Thr Tyr Thr Cys Asn Val Asp His Lys
                195                 200                 205

Pro Ser Asn Thr Lys Val Asp Lys Arg Val Glu Ser Lys Tyr Gly Pro
            210                 215                 220
```

```
Pro Cys Pro Pro Cys Pro Ala Pro Glu Phe Leu Gly Gly Pro Ser Val
225                 230                 235                 240

Phe Leu Phe Pro Lys Pro Lys Asp Thr Leu Met Ile Ser Arg Thr
            245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 19
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140
```

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
            165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 20
<211> LENGTH: 440
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln

```
            275                 280                 285
Phe Asn Ser Thr Tyr Arg Val Val Ser Val Leu Thr Val Leu His Gln
290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
                340                 345                 350

Lys Asn Gln Val Ser Leu Thr Cys Leu Val Lys Gly Phe Tyr Pro Ser
                355                 360                 365

Asp Ile Ala Val Glu Trp Glu Ser Asn Gly Gln Pro Glu Asn Asn Tyr
                370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
                420                 425                 430

Ser Leu Ser Leu Ser Leu Gly Lys
                435                 440
```

<210> SEQ ID NO 21
<211> LENGTH: 214
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 21

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190
```

```
Ala Cys Glu Val Thr His Gln Gly Leu Ser Ser Pro Val Thr Lys Ser
            195                 200                 205

Phe Asn Arg Gly Glu Cys
    210

<210> SEQ ID NO 22
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335
```

-continued

```
Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 23
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 24
<211> LENGTH: 114
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 24

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser
            20                  25                  30

Tyr Asp Met Ser Trp Val Arg Gln Ala Pro Gly Lys Gly Leu Asp Trp
        35                  40                  45

Val Ser Thr Ile Ser Gly Gly Thr Tyr Thr Tyr Tyr Gln Asp Ser
50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Ser Met Asp Tyr Trp Gly Gln Gly Thr Thr Val Thr Val Ser
            100                 105                 110

Ser Ala
```

<210> SEQ ID NO 25
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Arg Tyr
            20                  25                  30

Leu Asn Trp Tyr His Gln Lys Pro Gly Lys Ala Pro Lys Leu Leu Ile
        35                  40                  45

Tyr Gly Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Ser His Ser Ala Pro Leu
                85                  90                  95

Thr Phe Gly Gly Gly Thr Lys Val Glu Ile Lys Arg
            100                 105
```

<210> SEQ ID NO 26
<211> LENGTH: 1091
<212> TYPE: PRT
<213> ORGANISM: Homo sapiens

<400> SEQUENCE: 26

```
Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45
```

```
Leu Ser Leu Gln Arg Met Phe Asn Asn Cys Glu Val Val Leu Gly Asn
 50                  55                      60
Leu Glu Ile Thr Tyr Val Gln Arg Asn Tyr Asp Leu Ser Phe Leu Lys
 65                      70                  75                  80
Thr Ile Gln Glu Val Ala Gly Tyr Val Leu Ile Ala Leu Asn Thr Val
                     85                  90                  95
Glu Arg Ile Pro Leu Glu Asn Leu Gln Ile Ile Arg Gly Asn Met Tyr
                100                 105                 110
Tyr Glu Asn Ser Tyr Ala Leu Ala Val Leu Ser Asn Tyr Asp Ala Asn
            115                 120                 125
Lys Thr Gly Leu Lys Glu Leu Pro Met Arg Asn Leu Gln Gly Gln Lys
130                 135                 140
Cys Asp Pro Ser Cys Pro Asn Gly Ser Cys Trp Gly Ala Gly Glu Glu
145                 150                 155                 160
Asn Cys Gln Lys Leu Thr Lys Ile Ile Cys Ala Gln Gln Cys Ser Gly
                165                 170                 175
Arg Cys Arg Gly Lys Ser Pro Ser Asp Cys Cys His Asn Gln Cys Ala
            180                 185                 190
Ala Gly Cys Thr Gly Pro Arg Glu Ser Asp Cys Leu Val Cys Arg Lys
        195                 200                 205
Phe Arg Asp Glu Ala Thr Cys Lys Asp Thr Cys Pro Pro Leu Met Leu
210                 215                 220
Tyr Asn Pro Thr Thr Tyr Gln Met Asp Val Asn Pro Glu Gly Lys Tyr
225                 230                 235                 240
Ser Phe Gly Ala Thr Cys Val Lys Lys Cys Pro Arg Asn Tyr Val Val
                245                 250                 255
Thr Asp His Gly Ser Cys Val Arg Ala Cys Gly Ala Asp Ser Tyr Glu
            260                 265                 270
Met Glu Glu Asp Gly Val Arg Lys Cys Lys Cys Glu Gly Pro Cys
        275                 280                 285
Arg Lys Val Cys Asn Gly Ile Gly Ile Gly Glu Phe Lys Asp Ser Leu
            290                 295                 300
Ser Ile Asn Ala Thr Asn Ile Lys His Phe Lys Asn Cys Thr Ser Ile
305                 310                 315                 320
Ser Gly Asp Leu His Ile Leu Pro Val Ala Phe Arg Gly Asp Ser Phe
                325                 330                 335
Thr His Thr Pro Pro Leu Asp Pro Gln Glu Leu Asp Ile Leu Lys Thr
            340                 345                 350
Val Lys Glu Ile Thr Gly Phe Leu Leu Ile Gln Ala Trp Pro Glu Asn
        355                 360                 365
Arg Thr Asp Leu His Ala Phe Glu Asn Leu Glu Ile Ile Arg Gly Arg
370                 375                 380
Thr Lys Gln His Gly Gln Phe Ser Leu Ala Val Val Ser Leu Asn Ile
385                 390                 395                 400
Thr Ser Leu Gly Leu Arg Ser Leu Lys Glu Ile Ser Asp Gly Asp Val
                405                 410                 415
Ile Ile Ser Gly Asn Lys Asn Leu Cys Tyr Ala Asn Thr Ile Asn Trp
            420                 425                 430
Lys Lys Leu Phe Gly Thr Ser Gly Gln Lys Thr Lys Ile Ile Ser Asn
        435                 440                 445
Arg Gly Glu Asn Ser Cys Lys Ala Thr Gly Gln Val Cys His Ala Leu
450                 455                 460
Cys Ser Pro Glu Gly Cys Trp Gly Pro Glu Pro Arg Asp Cys Val Ser
```

```
              465                 470                 475                 480
        Cys Arg Asn Val Ser Arg Gly Arg Glu Cys Val Asp Lys Cys Asn Leu
                            485                 490                 495

Leu Glu Gly Glu Pro Arg Glu Phe Val Glu Asn Ser Glu Cys Ile Gln
                        500                 505                 510

Cys His Pro Glu Cys Leu Pro Gln Ala Met Asn Ile Thr Cys Thr Gly
                        515                 520                 525

Arg Gly Pro Asp Asn Cys Ile Gln Cys Ala His Tyr Ile Asp Gly Pro
                        530                 535                 540

His Cys Val Lys Thr Cys Pro Ala Gly Val Met Gly Glu Asn Asn Thr
        545                 550                 555                 560

Leu Val Trp Lys Tyr Ala Asp Ala Gly His Val Cys His Leu Cys His
                            565                 570                 575

Pro Asn Cys Thr Tyr Gly Cys Thr Gly Pro Gly Leu Glu Gly Cys Pro
                        580                 585                 590

Thr Asn Gly Pro Lys Ile Pro Ser Ile Ala Thr Gly Met Val Gly Ala
                        595                 600                 605

Leu Leu Leu Leu Leu Val Val Ala Leu Gly Ile Gly Leu Phe Met Arg
                    610                 615                 620

Arg Arg His Ile Val Arg Lys Arg Thr Leu Arg Arg Leu Leu Gln Glu
        625                 630                 635                 640

Arg Glu Leu Val Glu Pro Leu Thr Pro Ser Gly Glu Ala Pro Asn Gln
                            645                 650                 655

Ala Leu Leu Arg Ile Leu Lys Glu Thr Glu Phe Lys Lys Ile Lys Val
                        660                 665                 670

Leu Gly Ser Gly Ala Phe Gly Thr Val Tyr Lys Gly Leu Trp Ile Pro
                    675                 680                 685

Glu Gly Glu Lys Val Lys Ile Pro Val Ala Ile Lys Glu Leu Arg Glu
                        690                 695                 700

Ala Thr Ser Pro Lys Ala Asn Lys Glu Ile Leu Asp Glu Ala Tyr Val
        705                 710                 715                 720

Met Ala Ser Val Asp Asn Pro His Val Cys Arg Leu Leu Gly Ile Cys
                            725                 730                 735

Leu Thr Ser Thr Val Gln Leu Ile Thr Gln Leu Met Pro Phe Gly Cys
                        740                 745                 750

Leu Leu Asp Tyr Val Arg Glu His Lys Asp Asn Ile Gly Ser Gln Tyr
                    755                 760                 765

Leu Leu Asn Trp Cys Val Gln Ile Ala Lys Gly Met Asn Tyr Leu Glu
                    770                 775                 780

Asp Arg Arg Leu Val His Arg Asp Leu Ala Ala Arg Asn Val Leu Val
        785                 790                 795                 800

Lys Thr Pro Gln His Val Lys Ile Thr Asp Phe Gly Leu Ala Lys Leu
                            805                 810                 815

Leu Gly Ala Glu Glu Lys Glu Tyr His Ala Glu Gly Gly Lys Val Pro
                        820                 825                 830

Ile Lys Trp Met Ala Leu Glu Ser Ile Leu His Arg Ile Tyr Thr His
                    835                 840                 845

Gln Ser Asp Val Trp Ser Tyr Gly Val Thr Val Trp Glu Leu Met Thr
        850                 855                 860

Phe Gly Ser Lys Pro Tyr Asp Gly Ile Pro Ala Ser Glu Ile Ser Ser
        865                 870                 875                 880

Ile Leu Glu Lys Gly Glu Arg Leu Pro Gln Pro Ile Cys Thr Ile
                            885                 890                 895
```

```
Asp Val Tyr Met Ile Met Val Lys Cys Trp Met Ile Asp Ala Asp Ser
            900                 905                 910

Arg Pro Lys Phe Arg Glu Leu Ile Ile Glu Phe Ser Lys Met Ala Arg
            915                 920                 925

Asp Pro Gln Arg Tyr Leu Val Ile Gln Gly Asp Glu Arg Met His Leu
            930                 935                 940

Pro Ser Pro Thr Asp Ser Asn Phe Tyr Arg Ala Leu Met Asp Glu Glu
945                 950                 955                 960

Asp Met Asp Asp Val Val Asp Ala Asp Glu Tyr Leu Ile Pro Gln Gln
                965                 970                 975

Gly Phe Phe Ser Ser Pro Ser Thr Ser Arg Thr Pro Leu Leu Ser Ser
            980                 985                 990

Leu Ser Ala Thr Ser Asn Asn Ser  Thr Val Ala Cys Ile Asp Arg Asn
            995                 1000                1005

Gly Leu Gln Ser Cys Pro Ile  Lys Glu Asp Ser Phe  Leu Gln Arg
            1010            1015                1020

Tyr Ser  Ser Asp Pro Thr Gly  Ala Leu Thr Glu Asp  Ser Ile Asp
            1025            1030                1035

Asp Thr  Phe Leu Pro Val Pro  Gly Glu Trp Leu Val  Trp Lys Gln
            1040            1045                1050

Ser Cys  Ser Ser Thr Ser Ser  Thr His Ser Ala Ala  Ala Ser Leu
            1055            1060                1065

Gln Cys  Pro Ser Gln Val Leu  Pro Pro Ala Ser Pro  Glu Gly Glu
            1070            1075                1080

Thr Val  Ala Asp Leu Gln Thr  Gln
            1085            1090

<210> SEQ ID NO 27
<211> LENGTH: 1210
<212> TYPE: PRT
<213> ORGANISM: Mus musculus

<400> SEQUENCE: 27

Met Arg Pro Ser Gly Thr Ala Arg Thr Thr Leu Leu Val Leu Leu Thr
1               5                   10                  15

Ala Leu Cys Ala Ala Gly Gly Ala Leu Glu Glu Lys Lys Val Cys Gln
            20                  25                  30

Gly Thr Ser Asn Arg Leu Thr Gln Leu Gly Thr Phe Glu Asp His Phe
            35                  40                  45

Leu Ser Leu Gln Arg Met Tyr Asn Asn Cys Glu Val Val Leu Gly Asn
50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Ala Leu
            100                 105                 110

Tyr Glu Asn Thr Tyr Ala Leu Ala Ile Leu Ser Asn Tyr Gly Thr Asn
            115                 120                 125

Arg Thr Gly Leu Arg Glu Leu Pro Met Arg Asn Leu Gln Glu Ile Leu
            130                 135                 140

Ile Gly Ala Val Arg Phe Ser Asn Asn Pro Ile Leu Cys Asn Met Asp
145                 150                 155                 160

Thr Ile Gln Trp Arg Asp Ile Val Gln Asn Val Phe Met Ser Asn Met
```

```
            165                 170                 175
Ser Met Asp Leu Gln Ser His Pro Ser Ser Cys Pro Lys Cys Asp Pro
            180                 185                 190

Ser Cys Pro Asn Gly Ser Cys Trp Gly Gly Glu Glu Asn Cys Gln
            195                 200                 205

Lys Leu Thr Lys Ile Ile Cys Ala Gln Gln Cys Ser His Arg Cys Arg
            210                 215                 220

Gly Arg Ser Pro Ser Asp Cys Cys His Asn Gln Cys Ala Ala Gly Cys
225                 230                 235                 240

Thr Gly Pro Arg Glu Ser Asp Cys Leu Val Cys Gln Lys Phe Gln Asp
                245                 250                 255

Glu Ala Thr Cys Lys Asp Thr Cys Pro Pro Leu Met Leu Tyr Asn Pro
                260                 265                 270

Thr Thr Tyr Gln Met Asp Val Asn Pro Glu Gly Lys Tyr Ser Phe Gly
                275                 280                 285

Ala Thr Cys Val Lys Lys Cys Pro Arg Asn Tyr Val Val Thr Asp His
                290                 295                 300

Gly Ser Cys Val Arg Ala Cys Gly Pro Asp Tyr Tyr Glu Val Glu Glu
305                 310                 315                 320

Asp Gly Ile Arg Lys Cys Lys Lys Cys Asp Gly Pro Cys Arg Lys Val
                325                 330                 335

Cys Asn Gly Ile Gly Ile Gly Glu Phe Lys Asp Thr Leu Ser Ile Asn
                340                 345                 350

Ala Thr Asn Ile Lys His Phe Lys Tyr Cys Thr Ala Ile Ser Gly Asp
                355                 360                 365

Leu His Ile Leu Pro Val Ala Phe Lys Gly Asp Ser Phe Thr Arg Thr
                370                 375                 380

Pro Pro Leu Asp Pro Arg Glu Leu Glu Ile Leu Lys Thr Val Lys Glu
385                 390                 395                 400

Ile Thr Gly Phe Leu Leu Ile Gln Ala Trp Pro Asp Asn Trp Thr Asp
                405                 410                 415

Leu His Ala Phe Glu Asn Leu Glu Ile Ile Arg Gly Arg Thr Lys Gln
                420                 425                 430

His Gly Gln Phe Ser Leu Ala Val Val Gly Leu Asn Ile Thr Ser Leu
                435                 440                 445

Gly Leu Arg Ser Leu Lys Glu Ile Ser Asp Gly Asp Val Ile Ile Ser
                450                 455                 460

Gly Asn Arg Asn Leu Cys Tyr Ala Asn Thr Ile Asn Trp Lys Lys Leu
465                 470                 475                 480

Phe Gly Thr Pro Asn Gln Lys Thr Lys Ile Met Asn Asn Arg Ala Glu
                485                 490                 495

Lys Asp Cys Lys Ala Val Asn His Val Cys Asn Pro Leu Cys Ser Ser
                500                 505                 510

Glu Gly Cys Trp Gly Pro Glu Pro Arg Asp Cys Val Ser Cys Gln Asn
                515                 520                 525

Val Ser Arg Gly Arg Glu Cys Val Glu Lys Cys Asn Ile Leu Glu Gly
                530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
                580                 585                 590
```

```
Lys Thr Cys Pro Ala Gly Ile Met Gly Glu Asn Asn Thr Leu Val Trp
    595                 600                 605

Lys Tyr Ala Asp Ala Asn Asn Val Cys His Leu Cys His Ala Asn Cys
    610                 615                 620

Thr Tyr Gly Cys Ala Gly Pro Gly Leu Gln Gly Cys Glu Val Trp Pro
625                 630                 635                 640

Ser Gly Pro Lys Ile Pro Ser Ile Ala Thr Gly Ile Val Gly Gly Leu
                645                 650                 655

Leu Phe Ile Val Val Ala Leu Gly Ile Gly Leu Phe Met Arg Arg
            660                 665                 670

Arg His Ile Val Arg Lys Arg Thr Leu Arg Arg Leu Leu Gln Glu Arg
        675                 680                 685

Glu Leu Val Glu Pro Leu Thr Pro Ser Gly Glu Ala Pro Asn Gln Ala
    690                 695                 700

His Leu Arg Ile Leu Lys Glu Thr Glu Phe Lys Lys Ile Lys Val Leu
705                 710                 715                 720

Gly Ser Gly Ala Phe Gly Thr Val Tyr Lys Gly Leu Trp Ile Pro Glu
                725                 730                 735

Gly Glu Lys Val Lys Ile Pro Val Ala Ile Lys Glu Leu Arg Glu Ala
            740                 745                 750

Thr Ser Pro Lys Ala Asn Lys Glu Ile Leu Asp Glu Ala Tyr Val Met
    755                 760                 765

Ala Ser Val Asp Asn Pro His Val Cys Arg Leu Leu Gly Ile Cys Leu
770                 775                 780

Thr Ser Thr Val Gln Leu Ile Thr Gln Leu Met Pro Tyr Gly Cys Leu
785                 790                 795                 800

Leu Asp Tyr Val Arg Glu His Lys Asp Asn Ile Gly Ser Gln Tyr Leu
                805                 810                 815

Leu Asn Trp Cys Val Gln Ile Ala Lys Gly Met Asn Tyr Leu Glu Asp
            820                 825                 830

Arg Arg Leu Val His Arg Asp Leu Ala Ala Arg Asn Val Leu Val Lys
        835                 840                 845

Thr Pro Gln His Val Lys Ile Thr Asp Phe Gly Leu Ala Lys Leu Leu
    850                 855                 860

Gly Ala Glu Glu Lys Glu Tyr His Ala Glu Gly Gly Lys Val Pro Ile
865                 870                 875                 880

Lys Trp Met Ala Leu Glu Ser Ile Leu His Arg Ile Tyr Thr His Gln
                885                 890                 895

Ser Asp Val Trp Ser Tyr Gly Val Thr Val Trp Glu Leu Met Thr Phe
            900                 905                 910

Gly Ser Lys Pro Tyr Asp Gly Ile Pro Ala Ser Asp Ile Ser Ser Ile
        915                 920                 925

Leu Glu Lys Gly Glu Arg Leu Pro Gln Pro Ile Cys Thr Ile Asp
    930                 935                 940

Val Tyr Met Ile Met Val Lys Cys Trp Met Ile Asp Ala Asp Ser Arg
945                 950                 955                 960

Pro Lys Phe Arg Glu Leu Ile Leu Glu Phe Ser Lys Met Ala Arg Asp
                965                 970                 975

Pro Gln Arg Tyr Leu Val Ile Gln Gly Asp Glu Arg Met His Leu Pro
            980                 985                 990

Ser Pro Thr Asp Ser Asn Phe Tyr  Arg Ala Leu Met Asp  Glu Glu Asp
        995                 1000                 1005
```

-continued

```
Met Glu Asp Val Val Asp Ala Asp Glu Tyr Leu Ile Pro Gln Gln
    1010            1015            1020

Gly Phe Phe Asn Ser Pro Ser Thr Ser Arg Thr Pro Leu Leu Ser
    1025            1030            1035

Ser Leu Ser Ala Thr Ser Asn Asn Ser Thr Val Ala Cys Ile Asn
    1040            1045            1050

Arg Asn Gly Ser Cys Arg Val Lys Glu Asp Ala Phe Leu Gln Arg
    1055            1060            1065

Tyr Ser Ser Asp Pro Thr Gly Ala Val Thr Glu Asp Asn Ile Asp
    1070            1075            1080

Asp Ala Phe Leu Pro Val Pro Glu Tyr Val Asn Gln Ser Val Pro
    1085            1090            1095

Lys Arg Pro Ala Gly Ser Val Gln Asn Pro Val Tyr His Asn Gln
    1100            1105            1110

Pro Leu His Pro Ala Pro Gly Arg Asp Leu His Tyr Gln Asn Pro
    1115            1120            1125

His Ser Asn Ala Val Gly Asn Pro Glu Tyr Leu Asn Thr Ala Gln
    1130            1135            1140

Pro Thr Cys Leu Ser Ser Gly Phe Asn Ser Pro Ala Leu Trp Ile
    1145            1150            1155

Gln Lys Gly Ser His Gln Met Ser Leu Asp Asn Pro Asp Tyr Gln
    1160            1165            1170

Gln Asp Phe Phe Pro Lys Glu Thr Lys Pro Asn Gly Ile Phe Lys
    1175            1180            1185

Gly Pro Thr Ala Glu Asn Ala Glu Tyr Leu Arg Val Ala Pro Pro
    1190            1195            1200

Ser Ser Glu Phe Ile Gly Ala
    1205            1210
```

METHOD OF TREATING GLIOBLASTOMA MULTIFORME

CROSS-REFERENCE TO RELATED APPLICATIONS

This application is a 35 U.S.C. § 371 National Phase Entry of the International Application No. PCT/US2018/062011 filed Nov. 20, 2018, which designates the U.S. and which claims benefit under 35 U.S.C. § 119(e) of U.S. Provisional Application No. 62/590,070 filed Nov. 22, 2017, the contents of each of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Apr. 30, 2020, is named 043214-090410WOPT_SL.txt and is 85,449 bytes in size.

TECHNICAL FIELD

The field of the invention relates to immunotherapy.

BACKGROUND

Cancer is a life-threatening disease in which cells hyperproliferate, resulting in abnormal function, unregulated cell growth, lack of differentiation, local tissue invasion, and metastasis. Cancer therapies exploiting alterations in or characterized by the immune system's ability to destroy cells expressing particular cell-surface markers are showing success against cancers such as leukemias that do not form solid tumors. In particular, chimeric antigen receptor-expressing T cells (CAR-Ts) are used, which artificially target cytotoxic T cells for the killing of cancer cells. However, targeting solid tumors with this approach is proving more challenging. The solid tumor microenvironment tends to be immunosuppressive, often containing more than one layer of protection that obstructs the ability of immune cells to effectively reach and kill transformed cells of the tumor. Thus, new therapies that target solid tumors are needed for the treatment of cancer.

SUMMARY

One aspect of the technology described herein provides a method of treating a solid tumor cancer in a subject, the method comprises: (a) administering a genetically modified T cell expressing on its cell surface a chimeric T cell antigen receptor comprising a heterologous binding domain that specifically binds a tumor antigen expressed on the surface of cells of the cancer, and an intracellular signaling domain, wherein binding of the heterologous binding domain to the tumor antigen on the surface of a cancer cell activates the intracellular signaling domain and the T cell; and (b) administering a first genetically modified mesenchymal stem cell (MSC), that expresses a heterologous immunomodulatory polypeptide, wherein the heterologous immunomodulatory polypeptide potentiates cancer cell killing by the genetically modified T cell.

In one embodiment, the method further comprises before the administering steps, the step of resecting a solid tumor from the subject, wherein the resecting creates a cavity formerly occupied by tumor tissue.

In another embodiment, the first genetically modified mesenchymal stem cell is administered systemically.

In another embodiment, the first genetically modified mesenchymal stem cell is administered in the cavity formed by resection of the tumor.

In another embodiment, the first genetically modified mesenchymal stem cell is encapsulated in a matrix.

In another embodiment, the matrix permits cell migration out of the matrix.

In another embodiment, the matrix comprises a synthetic extracellular matrix.

In another embodiment, the matrix comprises a thiol-modified hyaluronic acid and a thiol-reactive cross-linker molecule.

In another embodiment, the thiol-reactive cross-linker molecule is polyethylene glycol diacrylate.

In another embodiment, the heterologous immunomodulatory polypeptide is a checkpoint inhibitor polypeptide.

In another embodiment, the heterologous immunomodulatory polypeptide is Interleukin (IL) IL-12, IL-2, IL-5, IL-15, interferon α, interferon β, interferon γ, or a combination thereof.

In another embodiment, the checkpoint inhibitor polypeptide comprises an antibody or antigen-binding domain thereof that binds a checkpoint polypeptide selected from the group consisting of PD-L1, PD-1, CTLA-4, TIM-3, LAG-3, and TIGIT.

In another embodiment, the checkpoint inhibitor polypeptide comprises an antibody or antigen-binding domain thereof that binds PD-L1.

In another embodiment, the heterologous binding domain comprises a nanobody or an scFv.

In another embodiment, the heterologous binding domain that specifically binds a tumor antigen expressed on the surface of cells of the cancer specifically binds a polypeptide selected from the group consisting of EGFRvIII, HER2, CD133, EGFR, IL13RA2, HER2, CSF1-R, L1-CAM, CTAG1B, GD2 and EGFR.

In another embodiment, the heterologous binding domain specifically binds to EGFRvIII.

In another embodiment, the genetically modified T cell is encapsulated in a matrix.

In another embodiment, the matrix permits cell migration out of the matrix.

In another embodiment, the genetically modified T cell is administered to the cavity formed by resection of the tumor.

In another embodiment, the cancer is metastatic cancer.

In another embodiment, the cancer is glioblastoma, glioma, medulloblastoma, breast cancer, melanoma, or non-small cell lung cancer.

In another embodiment, the first genetically modified mesenchymal stem cell additionally expresses a heterologous polypeptide selected from the group consisting of: TRAIL, EGFR nanobody-TRAIL fusion, Thrombospondin (TSP)-1, HSV-TK, cytosine deaminase (CD) or a combination thereof, or encodes and delivers an oncolytic virus.

In another embodiment, the oncolytic virus is an oHSV, oHSV-TRAIL, oHSV-granulocyte-macrophage colony-stimulating factor (GMCSF), or an oncolytic adenovirus.

In another embodiment, the method further comprises administering a second genetically modified mesenchymal stem cell, the second genetically modified mesenchymal stem cell expressing a heterologous polypeptide other than that expressed by the first mesenchymal stem cell, wherein the heterologous polypeptide is selected from the group consisting of: Interleukin (IL)-12, IL-2, IL-5, IL-15, TRAIL, EGFR nanobody-TRAIL fusion, Thrombospondin (TSP)-1, interferon α, interferon β, interferon γ, HSV-TK, and cytosine deaminase (CD); or encodes and delivers an oncolytic virus; or a combination thereof.

In another embodiment, the oncolytic virus is an oHSV, oHSV-TRAIL, oHSV-GMCSF, or an oncolytic adenovirus.

In another embodiment, the second genetically modified mesenchymal stem cell is encapsulated in a matrix.

In another embodiment, the matrix permits cell migration out of the matrix.

In another embodiment, the genetically modified mesenchymal stem cell and/or genetically modified T cell is administered within 6 days of tumor resection.

Another aspect of the technology described herein provides a composition comprising (a) a genetically modified T cell expressing on its cell surface a chimeric T cell antigen receptor comprising a heterologous binding domain that specifically binds a tumor antigen expressed on the surface of cells of a cancerous tumor, and an intracellular signaling domain, wherein binding of the heterologous binding domain to the tumor antigen on the surface of a cancer cell activates the intracellular signaling domain and the T cell; and (b) a first genetically modified mesenchymal stem cell, that expresses a heterologous immunomodulatory polypeptide.

In one embodiment, the composition further comprises a second genetically modified mesenchymal stem cell, the second genetically modified mesenchymal stem cell expressing a heterologous polypeptide different from that expressed by the first genetically-modified MSC, selected from the group consisting of: TRAIL, EGFR nanobody-TRAIL fusion, Thrombospondin (TSP)-1, interferon α, interferon β, interferon γ, HSV-TK, cytosine deaminase (CD), or encodes and expresses an oncolytic virus, or a combination thereof.

In another embodiment, the first genetically modified mesenchymal stem cell and the second genetically modified mesenchymal stem cell, if present, is/are encapsulated in a matrix.

In another embodiment, the genetically modified T cell is encapsulated in a matrix.

In another embodiment, the matrix permits cell migration out of the matrix.

In another embodiment, the heterologous immunomodulatory polypeptide is a checkpoint inhibitor polypeptide.

In another embodiment, the checkpoint inhibitor polypeptide comprises an antibody or antigen-binding domain thereof that binds a checkpoint polypeptide selected from the group consisting of PD-L1, PD-1, CTLA-4, TIM-3, LAG-3, or TIGIT.

In another embodiment, the checkpoint inhibitor polypeptide comprises an antibody or antigen-binding domain thereof that binds PD-L1.

In another embodiment, the heterologous binding domain that specifically binds a tumor antigen expressed on the surface of cells of the cancer specifically binds a polypeptide selected from the group consisting of EGFRvIII, HER2, CD133, EGFR, IL13RA2, HER2, CSF1-R, L1-CAM, CTAG1B, GD2 and EGFR.

In another embodiment, the heterologous binding domain specifically binds EGFRvIII.

In another embodiment, the composition described herein further comprises a pharmaceutically acceptable carrier.

In another embodiment, the composition described herein is for use in the treatment of a solid tumor cancer.

In another embodiment, the cancer is a metastatic cancer.

In another embodiment, the cancer is glioblastoma, glioma, medulloblastoma, breast cancer, melanoma, or non-small cell lung cancer.

Another aspect of the technology described herein provides a kit for treatment of a solid tumor, the kit comprising an embodiment of a composition comprising (a) a genetically modified T cell expressing on its cell surface a chimeric T cell antigen receptor comprising a heterologous binding domain that specifically binds a tumor antigen expressed on the surface of cells of a cancerous tumor, and an intracellular signaling domain, wherein binding of the heterologous binding domain to the tumor antigen on the surface of a cancer cell activates the intracellular signaling domain and the T cell; and (b) a first genetically modified mesenchymal stem cell, that expresses a heterologous immunomodulatory polypeptide as described herein, and packaging materials therefor. In one embodiment, the kit further comprises a second genetically modified MSC, which expresses a different heterologous polypeptide, e.g., one including, but not limited to IL-12, IL-2, IL-5, IL-15, TRAIL, EGFR nanobody-TRAIL fusion, Thrombospondin (TSP)-1, interferon α, interferon β, interferon γ, HSV-TK, and cytosine deaminase (CD); or encodes and delivers an oncolytic virus; or a combination thereof. In one embodiment, the genetically modified mesenchymal stem cell, the genetically-modified T cell, or both is/are encapsulated in a matrix as described herein. In another embodiment, the matrix permits cell migration out of the matrix.

Definitions

The terms "decrease", "reduce", "inhibit", or other grammatical forms thereof are used herein to mean a decrease by a statistically significant amount. In some embodiments, "reduce" or "decrease" or "inhibit" typically means a decrease by at least 10% as compared to a reference level (e.g. the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "inhibition" does not encompass a complete inhibition as compared to a reference level. "Complete inhibition" is a 100% inhibition as compared to a reference level. Where applicable, a decrease can be preferably down to a level accepted as within the range of normal for an subject without a given disease (e.g., cancer).

The terms "increased", "increase", "enhance", or grammatical forms thereof are used herein to mean an increase by a statically significant amount. In some embodiments, the terms "increased", "increase", or "enhance", can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

As used herein, a "subject" means a human or animal. Usually the animal is a vertebrate such as a primate, rodent, domestic animal or game animal. Primates include, for example, chimpanzees, cynomolgus monkeys, spider monkeys, and macaques, e.g., Rhesus. Rodents include, for example, mice, rats, woodchucks, ferrets, rabbits and hamsters. Domestic and game animals include, for example, cows, horses, pigs, deer, bison, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human.

Preferably, the subject is a mammal. The mammal can be a human, non-human primate, mouse, rat, dog, cat, horse, or cow, but is not limited to these examples. Mammals other than humans can be advantageously used as subjects that represent animal models of disease e.g., cancer. A subject can be male or female.

A subject can be one who has been previously diagnosed with or identified as suffering from or having a condition in need of treatment (e.g. glioblastoma or another type of cancer, among others) or one or more complications related to such a condition, and optionally, have already undergone treatment for the condition or the one or more complications related to the condition. Alternatively, a subject can also be one who has not been previously diagnosed as having such condition or related complications. For example, a subject can be one who exhibits one or more risk factors for the condition or one or more complications related to the condition or a subject who does not exhibit risk factors.

As used herein, the term "chimeric" refers to the product of the fusion of portions of at least two or more different polynucleotide molecules. In one embodiment, the term "chimeric" refers to a gene expression element produced through the manipulation of known elements or other polynucleotide molecules.

As used herein, "genetically modified" refers to a cell (e.g., T cell, or MSC) that has been altered to introduce changes to its genetic composition. A cell can be genetically modified to contain and/or express a gene product from one or more exogenous nucleic acid sequences not found in its genome (e.g., a T cell that is genetically modified to express a chimeric T cell antigen receptor, or an MSC genetically modified to express a gene product from a heterologous nucleic acid sequence). Alternatively, a cell can be genetically modified to either overexpress or inactivate or disrupt the expression of one or more genes or polypeptides. One skilled in the art will know how to introduce changes to the cell's genome using standard gene editing approaches.

In some embodiments, "activation" can refer to the state of a T cell that has been sufficiently stimulated to induce detectable cellular proliferation. T cell activation induces cytokine production including, but not limited to the production of IL-2. T cell activation can also refer to the upregulation of detectable effector functions, including but not limited to target cell cytotoxicity. At a minimum, an "activated T cell" as used herein is a proliferative T cell.

As used herein, the term "specifically binds" refer to a physical interaction between two molecules, compounds, cells and/or particles wherein the first entity binds to the second, target, entity with greater specificity and affinity than it binds to a third entity which is a non-target. In some embodiments, specific binding can refer to an affinity of the first entity for the second target, entity, which is at least 10 times, at least 50 times, at least 100 times, at least 500 times, at least 1000 times or more, greater than the affinity for the third non-target entity under the same conditions. A reagent specific for a given target is one that exhibits specific binding for that target under the conditions of the assay being utilized. A non-limiting example includes an antibody, or a ligand, which recognizes and binds with a cognate binding partner (for example, a tumor antigen or a checkpoint polypeptide) protein. For the avoidance of doubt, as used herein, "specifically binds" also requires the ability of a binding factor, such as a polypeptide or antibody binding domain to bind to a target, such as a molecule present on the cell surface, with a $K_D$ of $10^{-5}$ M (10000 nM) or less, e.g., $10^{-6}$ M or less, $10^{-7}$ M or less, $10^{-8}$ M or less, $10^{-9}$ M or less, $10^{-10}$ M or less, $10^{-11}$ M or less, or $10^{-12}$ M or less. Specific binding can be influenced by, for example, the affinity and avidity of the polypeptide agent and the concentration of polypeptide agent. The person of ordinary skill in the art can determine appropriate conditions under which binding agents described herein selectively bind the targets using any suitable methods, such as titration of a polypeptide agent in a suitable cell binding assay.

In one embodiment, the term "engineered" and its grammatical equivalents as used herein can refer to one or more human-designed alterations of a nucleic acid, e.g., the nucleic acid within an organism's genome or genetic composition. The term can refer to alterations, additions, and/or deletion of genes. An "engineered cell" can refer to a cell with an added, deleted and/or altered gene (e.g., a T cell engineered to express a chimeric T cell antigen receptor). The term "cell" or "engineered cell" and their grammatical equivalents as used herein can refer to a cell of human or non-human animal origin.

The term "polypeptide" as used herein refers to a polymer of amino acids. The terms "protein" and "polypeptide" are used interchangeably herein. A peptide is a relatively short polypeptide, typically between about 2 and 60 amino acids in length. Polypeptides used herein typically contain amino acids such as the 20 L-amino acids that are most commonly found in proteins. However, other amino acids and/or amino acid analogs known in the art can be used. One or more of the amino acids in a polypeptide may be modified, for example, by the addition of a chemical entity such as a carbohydrate group, a phosphate group, a fatty acid group, a linker for conjugation, functionalization, etc. A polypeptide that has a nonpolypeptide moiety covalently or noncovalently associated therewith is still considered a "polypeptide." Exemplary modifications include glycosylation and palmitoylation. Polypeptides can be purified from natural sources, produced using recombinant DNA technology or synthesized through chemical means such as conventional solid phase peptide synthesis, etc. The term "polypeptide sequence" or "amino acid sequence" as used herein can refer to the polypeptide material itself and/or to the sequence information (i.e., the succession of letters or three letter codes used as abbreviations for amino acid names) that biochemically characterizes a polypeptide. A polypeptide sequence presented herein is presented in an N-terminal to C-terminal direction unless otherwise indicated.

In some embodiments, a nucleic acid encoding a polypeptide as described herein (e.g. an immunomodulatory polypeptide) is comprised by a vector. In some of the aspects described herein, a nucleic acid sequence encoding a given polypeptide as described herein, or any module thereof, is operably linked to a vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, artificial chromosome, virus, virion, etc.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

As used herein, the term "viral vector" refers to a nucleic acid vector construct that includes at least one element of viral origin and has the capacity to be packaged into a viral vector particle. The viral vector can contain a nucleic acid encoding a polypeptide as described herein in place of non-essential viral genes. The vector and/or particle may be utilized for the purpose of transferring nucleic acids into cells either in vitro or in vivo. Numerous forms of viral vectors are known in the art.

By "recombinant vector" is meant a vector that includes a heterologous nucleic acid sequence, or "transgene" that is capable of expression in vivo. It should be understood that the vectors described herein can, in some embodiments, be combined with other suitable compositions and therapies. In some embodiments, the vector is episomal. The use of a suitable episomal vector provides a means of maintaining the nucleotide of interest in the subject in high copy number extra-chromosomal DNA thereby eliminating potential effects of chromosomal integration.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. glioblastoma or other solid tumor cancer. The term "treating" includes reducing or alleviating at least one adverse effect or symptom of a condition, disease or disorder. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "administering," refers to the placement of a therapeutic or pharmaceutical composition as disclosed herein into a subject by a method or route which results in at least partial delivery of the agent at a desired site. Pharmaceutical compositions comprising agents as disclosed herein can be administered by any appropriate route which results in an effective treatment in the subject.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Other terms are defined within the description of the various aspects and embodiments of the technology of the following.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1C-E shows flow cytometry plots (C) and plots (D-E) showing CD4+ and CD8+ effector T cells at different time points.

FIG. 2A shows RT-PCR analysis of IFNβ1/2 transcript in CT-2A and GL261 cDNA extracts. FIG. 2B shows Western blot analysis on CT2A cell lysates post-treatment with mIFN13 showing phosphorylation status of STAT1, p38. FIG. 2C shows representative flow cytometry density plots of cell cycle analysis. FIG. 2D shows plot showing viability of CT2A cells treated with MSC-mIFN13 and MSC-GFP conditioned medium. A representative fluorescence image MSC expressing mIFN13 is shown. FIG. 2E shows Kaplan-Meier survival curves of C57/B6 or SCID mice bearing CT2A-FmC injected intratumorally with MSC-mIFN13 or MSC-GFP.

FIG. 3A-B shows (A) Western blot and (B) flow cytometry analysis on mouse GBM cells to assess PD-L1 expression. Unstained cells shown as blue were used for comparison. FIG. 3C depicts the design of retroviral vector expressing secretable ScFv-PD-L1. FIG. 3D depicts a plot showing survival of GBM cells expressing EGFRvIII-Fluc treated with conditioned medium from MSC-ScFV-PD-L1 and EGFRvIII CAR T cells (GBM:T cells ratio 1:5.) Fluorescence image of MSC transduced with RV-ScFV-PD-L1 is shown. FIG. 3E shows Kaplan-Meier survival curves of C57/B6 mice bearing CT2A-FmC tumors intratumorally injected with MSC-ScFv-PD-L1 or MSC-GFP.

FIG. 5A-C shows MSC-IFNβ treatment upregulates PD-L1 on tumor cells in vitro and in vivo. FIG. 5A-B shows Gl261-FmC were treated with (A) recombinant IFNβ or (B) co-cultured with MSC-IFNβ or MSC-GFP in the presence or absence of 10 μg/mL IFNaR1 blocking antibody, MAR1-5A3 followed by FACS analysis of tumor cell PD-L1 expression 48 h post treatment. FIG. 5C shows FACS analysis showing PD-L1 expression on tumor cells isolated from GL261-FmC tumor bearing mice 3 days post-intratumoral injection with MSC-IFNβ or MSC-GFP.

FIG. 6A shows Photomicrograph of mouse MSC expressing IL-12. FIG. 6B shows Western blot analysis showing expression of IL-12 in cells lysates and conditioned medium. FIG. 6C depicts a plot showing sorted T cells activated with anti-CD3 and anti-CD28 and cultured in presence of 1 μL of conc. supernatant from MSC-IL-12 and MSC-GFP. FIG. 6D-E shows activated T cells were followed by intracellular staining for IFNγ and granzyme B. Plots showing % IFNγ+ cells in CD4 T cells (D) and % granzyme B+ cells in CD8+ T cells (E). Insets show representative flow cytometry plots. FIG. 6F shows that mice bearing syngeneic brain tumors were implanted intratumorally with $5 \times 10^5$ MSC-IL-12 or MSC-GFP. Plot showing changes in tumor volumes over time.

FIG. 7A shows regulatable dual promoter vector design. FIG. 7B-C shows plot and representative images showing activity of MSC expressing regulatable GFP-Fluc post 9 TB-Dox induction in vitro (1 μg/mL) (B) and in mice implanted intracranially with MSC-GFP-Fluc ($1 \times 10^5$) and administered 9 TB-dox (10 mg/kg) i.p. twice daily with initial dose starting at 12 hours post MSC implantation (C). FIG. 7D shows Western blot analysis on the lysates MSC-N1KO transduced with LV-TET-IL2 and treated with 9 TB-Dox.

FIG. 8A shows human and mouse EGFRvIII CAR design. FIG. 8B shows lentiviral and retroviral constructs for transduction of T cells. FIG. 8C shows T cells were isolated from PBMCs and were activated with anti-CD3+28 beads for 24 hours followed by addition of LV-EGFRvII CAR-Fluc supernatant. Three days post-transduction, T cells were harvested for flow cytometry analysis where cells were gated on live cells by SYTOX™ live/dead staining followed by GFP expression, and transduced T cells served as control (C). FIG. 8D shows Western blot analysis with CD3z antibody. FIG. 8E-F shows human GBM-vIII-mcherry-fluc cells were co-cultured with CAR transduced T cells or un-transduced cells for 24 hours. Live GBM cells were detected by Rluc bioluminescence and mCherry fluorescence. % specific lysis was calculated.

FIG. 9B shows mice bearing human GBM expressing vIII variant of EGFR and Rluc were treated intravenously with EGFRvIII CAR T or T cells expressing Fluc ($1 \times 10^6$ cells). Mice were imaged sequentially for Fluc (T cells) and Rluc (Tumor cells) in vivo. Representative images and include T cell imaging, tumor imaging, and representative plots showing changes in tumor volumes post T cell treatment.

FIG. 10A-B shows EGFRvIII CAR engineered T cells implanted intratumorally have efficacy in mice bearing brain tumors. FIG. 10A shows the experimental outline. FIG. 10B shows Mice bearing human GBM expressing vIII variant of EGFR and Rluc were implanted intratumorally with EGFRvIII CAR T or T cells ($5 \times 10^5$ cells). Mice were imaged for tumor volumes by Rluc imaging in vivo. Representative images and plots showing changes in tumor volumes post T cell treatment are shown.

FIG. 11A shows the experimental outline. FIG. 11B shows mice bearing human GBM expressing vIII variant of EGFR and Fluc were resected and implanted with sECM encapsulated EGFRvII CAR T and MSC-IL-12 or MSC-GFP ($5 \times 10^5$ each population). Mice were imaged for tumor volumes by Fluc imaging in vivo. Representative plot showing changes in tumor volumes post treatment.

DETAILED DESCRIPTION

Figure 1A:
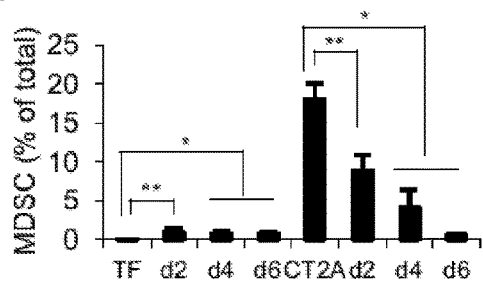
FIGS. 1A-E depicts experimental data showing that surgical GBM tumor resection reduces myeloid derived suppressor cells (MDSCs) and enhances infiltration of DC and T cells. Mono nuclear cells isolated from whole brains from different tumor free (TF) and CT2A-FmC tumor bearing brains pre and post resection and stained with antibodies recognizing CD45, CD11b, Gr-1, CD11c, CD4 and CD8, and analyzed by flow cytometry. The percentage of (FIG. 1A) MDSC ($CD45^{high}CD11b^{high}Gr-1^{high}$) and (FIG. 1B) lymphocytes ($CD45^{high}CD11b^{low}$) are shown.
Figure 1B:
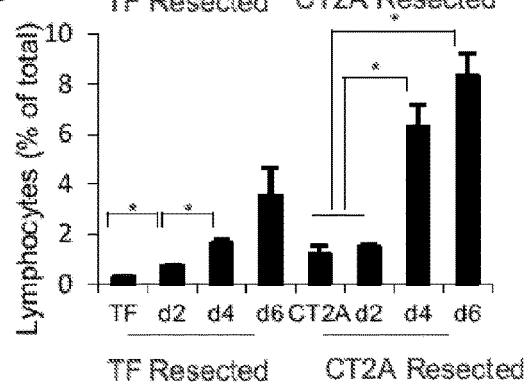
Figure 1C:
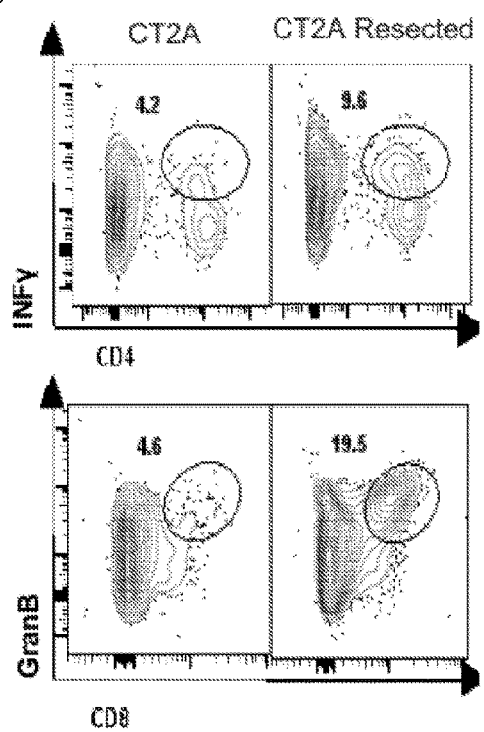
Figure 1D:
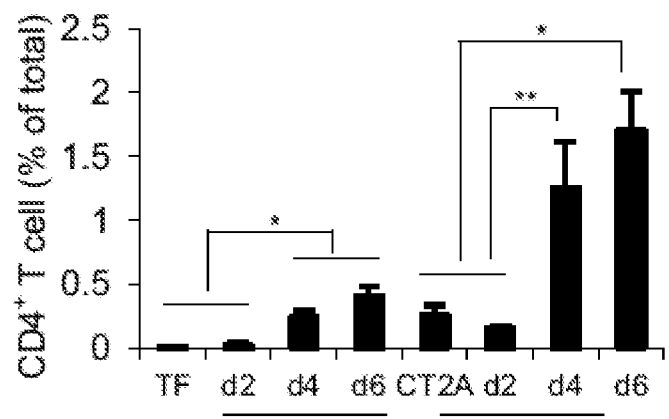
Figure 1E:
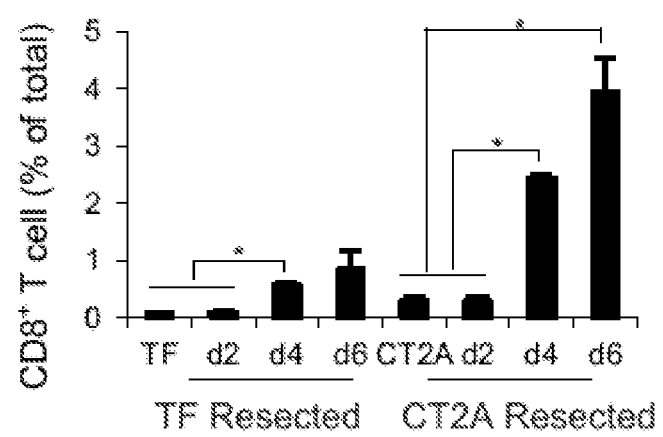

Cancer therapies exploiting the immune system's ability to destroy cells expressing particular cell-surface markers are showing success against cancers such as leukemias that do not form solid tumors. In particular, chimeric antigen receptor-expressing T cells (CAR T) are used, which artificially target cytotoxic T cells to kill tumor cells by introducing a modified T cell receptor construct to the T cells, in which the receptor's native antigen-binding domain is replaced with a binding domain, most often involving an antibody's antigen-binding domain, that binds a tumor antigen. CAR Ts are proving very effective against non-solid tumor cancers. However, targeting solid tumors with this approach is proving more challenging. The solid tumor microenvironment, it turns out, is immunosuppressive, often containing more than one layer of protection that obstructs the ability of immune cells to effectively reach and kill transformed cells of the tumor. As but one example, many tumors express immune checkpoint ligands, such as PD-L1, the normal functions of which are to assist in maintaining immune homeostasis and thereby avoid autoimmunity. A tumor expressing PD-L1 will tend to suppress the activity of cytotoxic T cells reaching the tumor by interaction with the negative immunoregulator PD-1 expressed on the T cells.

A particularly difficult scenario is presented in the case of brain tumors, such as glioblastoma, glioma and medulloblastoma. Among other things, the blood-brain barrier tends to limit access of systemically administered agents to the brain tissue and to tumors therein. Not only are glioblastomas difficult to reach with systemically administered agents, the form in which they grow and encroach into normal brain tissues renders them difficult to remove surgically—glioblastomas, in particular, tend to extend tendrils out from the tumor mass that essentially ensure that surgery cannot capture all tumor cells.

One approach for overcoming the immunosuppressive effects of tumor-expressed immune checkpoint molecules in solid tumors is to use inhibitors of the immune checkpoint molecules, referred to as checkpoint inhibitors. Delivery of checkpoint inhibitors such as antibodies or constructs including antigen-binding domains thereof to the tumor microenvironment would be expected to counter the checkpoint molecule's suppressive signal and permit CAR Ts to effectively target the tumor's cells.

Systemic delivery of checkpoint inhibitors is effective in some instances, but comes with the likelihood of unwanted side effects, and limitations due to circulating half-life. One approach to addressing this is to administer a cell expressing the checkpoint inhibitor polypeptide, thereby providing a continuous supply of the inhibitor.

Methods of increasing T cell recruitment to tumors can improve the anti-tumor effects of CAR Ts. Mesenchymal stem cells are known to both home to sites of solid tumors, and to promote T cell recruitment. As such, MSCs would tend to be attractive candidates for the delivery of therapeutic molecules to the site of a tumor. However, MSCs are also well known for their immunosuppressive effects—that is, MSCs suppress T cell proliferation and cytokine production, inhibit dendritic cell expansion and function, reduce natural killer (NK) cell activity, and enhance immunosuppressive Treg cell activities. See, e.g., Lee et al. *Scientific Reports* (2017). MSCs are known to recruit T cells to the site of a tumor, but their overall effect in the tumor microenvironment may hinder the effects of such recruited cells. Therefore, while MSCs have desirable characteristics for a cell to deliver an anti-tumor therapy, given their well-known immunosuppressive activities, one would not necessarily expect delivery of an anti-tumor agent, or even a checkpoint inhibitor to the site of a tumor by an MSC to assist with CAR T-mediated cancer cell killing. To the contrary, one would expect the immunosuppressive activities of MSCs to limit or impede the efficacy of CAR Ts. However, as described herein, the use of MSCs to deliver immunomodulatory agents can potentiate CAR-T cell-mediated cancer cell killing.

Further, the resection of a tumor promotes a reduction of myeloid-derived suppressor cells and a simultaneous recruitment of CD4/CD8 T cells. As such, apart from simply removing the cancerous tissue, resection can assist in countering the immunosuppressive tumor microenvironment, and can be combined with the approach of administering modified MSCs and CAR T cells as described herein, to beneficial effect.

Engineered stem cells and CAR T based therapies are used in cancer research. However, the art fails to teach the efficacy of creating and using bimodal MSC expressing immunomodulatory agents and immune checkpoint inhibitors and CART cells. Described herein is: (1) the local delivery of engineered stem cells and systemic delivery of tumor cell surface directed CAR T for efficient recruitment and functionality of CAR T; and (2) a bi-modal immunomodulatory stem cell that releases immune modulatory agents and immune check point inhibitors locally within the resected tumor microenvironment and influences tumor progression.

The MSCs described herein are engineered to deliver, for example, cytokines, immunomodulators, viruses, or other agents that complement the activity of co-administered CAR T cells targeting a solid tumor. The CAR T cells are engineered to be directed, for example, to tumors expressing EGFRvIII and IL13Ra2, cell surface receptors specifically expressed in tumor cells. The ability of engineered stem cells to target cell surface receptors on tumor cells to enhance the immune function and simultaneously recruit systemically injected CAR T cells under diverse conditions and with diverse delivery modalities can permit this approach to become a widely used tool in cancer therapeutics. The technology described herein is therefore a new class of therapeutics, ESC-CAR T (engineered stem cells and CAR T) and methods of using them in cancer therapy are taught herein.

Accordingly, one aspect of the technology described herein provides a method for treating a solid tumor comprising administering a genetically modified T cell expressing on its cell surface a chimeric T cell antigen receptor comprising a heterologous binding domain that specifically binds a tumor antigen expressed on the surface of cells of the cancer, and an intracellular signaling domain, wherein binding of the heterologous binding domain to the tumor antigen on the surface of a cancer cell activates the intracellular signaling domain and the T cell; and administering a first genetically modified mesenchymal stem cell (MSC), that expresses a heterologous immunomodulatory polypeptide, wherein the heterologous immunomodulatory polypeptide potentiates cancer cell killing by the genetically modified T cell.

"Cancer" as used herein can refer to a hyperproliferation of cells that exhibit a loss of normal cellular control that results in unregulated growth, lack of differentiation, local tissue invasion, and metastasis. Cancer can be a solid tumor, leukemia, lymphoma, or multiple myeloma. Methods and compositions described herein are mainly directed at the treatment of solid tumors. As used herein, the term "tumor" refers to an abnormal growth of cells or tissues, e.g., of malignant type or benign type. Non-limiting examples of solid tumors include Adrenocortical Tumor, Alveolar Soft Part Sarcoma, Carcinoma, Chondrosarcoma, Colorectal Carcinoma, Desmoid Tumors, Desmoplastic Small Round Cell Tumor, Endocrine Tumors, Endodermal Sinus Tumor, Epithelioid Hemangioendothelioma, Ewing Sarcoma, Germ Cell Tumors (Solid Tumor), Giant Cell Tumor of Bone and Soft Tissue, Glioblastoma, Hepatoblastoma, Hepatocellular Carcinoma, Melanoma, Nephroma, Neuroblastoma, Non-Rhabdomyosarcoma Soft Tissue Sarcoma (NRSTS), Osteosarcoma, Paraspinal Sarcoma, Renal Cell Carcinoma, Retinoblastoma, Rhabdomyosarcoma, Synovial Sarcoma, and Wilms Tumor. Solid tumors can be found in bones, muscles, the brain, or organs, and can be sarcomas or carcinomas, where the technology described herein can overcome barriers to solid tumor treatment with CAR T cells. It is contemplated that aspects of the technology described herein can be used to treat all types of solid tumor cancers, including cancers not listed in the instant specification.

CAR T Cells

As used herein, "chimeric antigen receptor" or "CAR" refers to an artificially constructed hybrid polypeptide comprising an antigen-binding domain (e.g., an antigen-binding portion of an antibody (e.g., a scFV)), a transmembrane domain, and a T-cell signaling and/or T-cell activation domain (e.g., intracellular signaling domain). CARs have the ability to redirect T-cell specificity and reactivity toward a selected target in a non-MHC-restricted manner, exploiting the antigen-binding properties of monoclonal antibodies. The non-MHC-restricted antigen recognition gives T-cells expressing CARs the ability to recognize an antigen independent of antigen processing, thus bypassing a major mechanism of tumor escape. Moreover, when expressed in T-cells, CARs advantageously do not dimerize with endogenous T-cell receptor (TCR) alpha and beta chains. Most commonly, the CAR's extracellular binding domain is composed of a single chain variable fragment (scFv) derived from fusing the variable heavy and light regions of a murine or humanized monoclonal antibody. Alternatively, scFvs may be used that are derived from Fab's (instead of from an antibody, e.g., obtained from Fab libraries), in various embodiments, this scFv is fused to a transmembrane domain and then to an intracellular signaling domain. "First-generation" CARs include those that provide CD3zeta (CD3ζ) signals upon antigen binding, "Second-generation" CARs provide both costimulation (e.g., CD28 or CD 137) and activation (CD3ζ). "Third-generation" CARs provide multiple costimulatory (e.g., CD28 and CD 137) domains and activation domains (e.g., CD3ζ). In one embodiment, the CAR polypeptide of the technology is selected to have high affinity or avidity for the antigen. Further discussion of CARs can be found, e.g., in Maus et al. *Blood* 2014 123:2624-35; Reardon et al. *Neuro-Oncology* 2014 16:1441-1458; Hoyos et al. *Haematologica* 2012 97:1622; Byrd et al. *J Clin Oncol* 2014 32:3039-47; Maher et al. *Cancer Res* 2009 69:4559-4562; and Tamada et al. *Clin Cancer Res* 2012 18:6436-6445; each of which is incorporated by reference herein in its entirety.

In some embodiments, a chimeric T cell antigen receptor comprises an extracellular binding domain that comprises a heterologous binding domain that specifically binds EGFRvIII; a transmembrane domain; one or more intracellular co-stimulatory signaling domains; and a primary signaling domain. As used herein, the terms, "binding domain," "extracellular domain," "extracellular binding domain," "antigen-specific binding domain," and "extracellular antigen specific binding domain," are used interchangeably and provide a chimeric T cell antigen receptor with the ability to specifically bind to the target antigen of interest, e.g., EFGRvIII. The binding domain can be derived either from a natural, synthetic, semi-synthetic, or recombinant source.

In some embodiments, the binding domain of the chimeric T cell antigen receptor can be followed by one or more "spacer domains," which refers to a region that moves the antigen binding domain away from the effector cell surface to enable proper cell/cell contact, antigen binding and activation. The spacer domain can be derived either from a natural, synthetic, semi-synthetic, or recombinant source.

The binding domain of the chimeric T cell antigen receptor is generally followed by one or more "hinge domains," which plays a role in positioning the antigen binding domain away from the effector cell surface to permit proper cell/cell contact, antigen binding and activation. A chimeric T cell antigen receptor generally comprises one or more hinge domains between the binding domain and the transmembrane domain (TM). The hinge domain may be derived either from a natural, synthetic, semi-synthetic, or recombinant source. The hinge domain can include the amino acid sequence of a naturally occurring immunoglobulin hinge region or an altered immunoglobulin hinge region. Illustrative hinge domains suitable for use in the chimeric T cell antigen receptor described herein include the hinge region derived from the extracellular regions of type 1 membrane proteins such as CD8α, CD4, CD28 and CD7, which may be wild-type hinge regions from these molecules or may be altered. In one embodiment, the hinge domain comprises a human CD8α hinge region. In another embodiment, the hinge region comprises a mouse CD28 hinge region.

The "transmembrane domain" is the portion of the chimeric T cell antigen receptor that fuses the extracellular binding portion and intracellular signaling domain and anchors the chimeric T cell antigen receptor to the plasma membrane of the immune effector cell. The TM domain may be derived either from a natural, synthetic, semi-synthetic, or recombinant source. The TM domain may be derived from (i.e., comprise at least the transmembrane region(s) of) the alpha, beta or zeta chain of the T-cell receptor, CD3ε, CD3ζ, CD4, CD5, CD8α, CD9, CD 16, CD22, CD27, CD28, CD33, CD37, CD45, CD64, CD80, CD86, CD 134, CD137, CD152, CD 154, and PD1. In one embodiment, the transmembrane domain comprises a human CD8α transmembrane domain. In another embodiment, the transmembrane domain comprises a mouse CD28 transmembrane domain.

In some embodiments, chimeric T cell antigen receptors contemplated herein comprise an intracellular signaling domain. An "intracellular signaling domain," refers to the part of a chimeric T cell antigen receptor that participates in transducing the message of effective chimeric T cell antigen receptor binding to a target antigen into the interior of the immune effector cell to elicit effector cell function, e.g., activation, cytokine production, proliferation and cytotoxic activity, including the release of cytotoxic factors to the chimeric T cell antigen receptor-bound target cell, or other cellular responses elicited with antigen binding to the extracellular domain of the chimeric T cell antigen receptor. In some embodiments, a chimeric T cell antigen receptor contemplated herein comprises an intracellular signaling domain that comprises one or more "co-stimulatory signaling domain" and a "primary signaling domain."

As used herein, the term, "co-stimulatory signaling domain," or "co-stimulatory domain", refers to an intracellular signaling domain of a co-stimulatory molecule. Co-stimulatory molecules are cell surface molecules other than antigen receptors or Fc receptors that provide a second signal required for efficient activation and function of T lymphocytes upon binding to antigen. Illustrative examples of such co-stimulatory molecules include CARD11, CD2, CD7, CD27, CD28, CD30, CD40, CD54 (ICAM), CD83, CD134 (OX40), CD137 (4-1BB), CD150 (SLAMF1), CD152 (CTLA4), CD223 (LAG3), CD270 (HVEM), CD273 (PD-L2), CD274 (PD-L1), CD278 (ICOS), DAP10, LAT, NKD2C SLP76, TRIM, and ZAP70. In one embodiment, the intracellular domain is the intracellular domain of human 4-1BB. In another embodiment, the intracellular domain is the intracellular domain of mouse CD28.

Primary signaling domains regulate primary activation of the TCR complex either in a stimulatory way, or in an inhibitory way. Primary signaling domains that act in a stimulatory manner may contain signaling motifs which are known as immunoreceptor tyrosine-based activation motifs or ITAMs. Illustrative examples of ITAM containing primary signaling domains that are of particular use in the invention include those derived from TCRζ, FcRγ, FcRβ, CD3γ, CD3δ, CD3ε, CD3ζ, CD22, CD79a, CD79b, and CD66d. In one embodiment, the primary signaling domain is mouse CD3ζ. In another embodiment, the primary signaling domain is human CD3ζ.

In one embodiment, the chimeric T cell antigen receptor comprises a mouse CD8α leader sequence, a 3C10 scFv, a mouse CD28 hinge region, a mouse CD28 transmembrane domain, a mouse CD28 intracellular signaling domain, and a mouse CD3z primary signaling domain.

In another embodiment, the chimeric T cell antigen receptor comprises a human CD8α leader sequence, a 139 scFv, a human CD8α hinge region, a human CD8α transmembrane domain, a human 4-1BB intracellular signaling domain, and a human CD3ζ primary signaling domain.

In one embodiment, the chimeric T cell antigen receptor comprises a heterologous binding domain that binds a tumor antigen. As used herein, the term "tumor antigen" refers to antigens which are differentially expressed by cancer cells and can thereby be exploited in order to target cancer cells. Tumor antigens are antigens which can potentially stimulate tumor-specific immune responses. Some of these antigens are encoded, although not necessarily expressed, by normal cells. These antigens can be characterized as those which are normally silent (i.e., not expressed) in normal cells, those that are expressed only at certain stages of differentiation and those that are temporally expressed such as embryonic and fetal antigens. Other tumor antigens are encoded by mutant cellular genes, such as oncogenes (e.g., activated ras oncogene), suppressor genes (e.g., mutant p53), and fusion proteins resulting from internal deletions or chromosomal translocations. Still other tumor antigens can be encoded by viral genes such as those carried on RNA and DNA tumor viruses. Many tumor antigens have been defined in terms of multiple solid tumors: MAGE 1, 2, & 3, defined by immunity; MART-1/Melan-A, gp100, carcinoembryonic antigen (CEA), HER2, mucins (i.e., MUC-1), prostate-specific antigen (PSA), and prostatic acid phosphatase (PAP). In addition, viral proteins such as some encoded by hepatitis B (HBV), Epstein-Barr (EBV), and human papilloma (HPV) have been shown to be important in the development of hepatocellular carcinoma, lymphoma, and cervical cancer, respectively.

In one embodiment, the tumor antigen is EGFRvIII. As used herein, the term "EGFRvII" or "Epidermal growth factor receptor" or "EGFR" refers to a transmembrane protein that is a receptor for members of the epidermal growth factor family of extracellular protein ligands. EGFR is a member of the ErbB family of receptors. EGFR sequences are known for a number of species, e.g., human CD28 (NCBI Gene ID: 1956), mRNA (NCBI Ref Seq NM_001346897.1), and polypeptide sequences (NP_001333826.1, SEQ ID NO: 26), and mouse polypeptide sequences (NP_997538.1, SEQ ID NO: 27). EGFR can refer to human EGFR, including naturally occurring variants and alleles thereof. In some embodiments of, e.g., in veterinary applications, EGFR can refer to the CD28 of, e.g., dog, cat, cow, horse, pig, and the like. Homologs and/or orthologues of human EGFR are readily identified for such species by one of skill in the art, e.g., using the NCBI orthologues search function or searching available sequence data for a given species for sequence similar to a reference EGFR sequence. Examples of antibodies that bind to EGFRvIII can be found in US20140322275A1 summarized in Table 1.

Over expression of EGFR signaling and mutations resulting in EGFR variants have been linked to disease states, such as cancer. Specifically, aberrant signaling of EGFR variant III (EGFRvIII) has been shown to be important in driving tumor progression and often correlates with poor prognosis; EGFRvIII is associated with increase proliferation of glioma cells in subjects diagnosed with glioblastoma.

EGFRvIII is the most common extracellular mutation of EGFR, and is also known as de2-7EGFR and ΔEGFR. EGFRvIII results from in-frame deletion of 801 base pairs spanning exons 2-7 of the EGFR coding sequence, resulting in the deletion of 267 amino acids from the extracellular domain.

Antibody Reagents

As used herein, the term "antibody" refers to immunoglobulin molecules and immunologically active portions of immunoglobulin molecules, i.e., molecules that contain an antigen binding site that immunospecifically binds an antigen. The term also refers to antibodies comprised of two immunoglobulin heavy chains and two immunoglobulin light chains as well as a variety of forms including full length antibodies and antigen-binding portions thereof; including, for example, an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody (dAb), a diabody, a multispecific antibody, a dual specific antibody, an anti-idiotypic antibody, a bispecific antibody, a functionally active epitope-binding portion thereof, and/or bifunctional hybrid antibodies.

In some embodiments, the antibody or antigen-binding portion thereof is a fully human antibody. In some embodiments, the antibody, antigen-binding portion thereof, is a humanized antibody or antibody reagent. In some embodiments, the antibody, antigen-binding portion thereof, is a fully humanized antibody or antibody reagent. In some embodiments, the antibody or antigen-binding portion thereof, is a chimeric antibody or antibody reagent. In some embodiments, the antibody, antigen-binding portion thereof, is a recombinant polypeptide. In some embodiments, the chimeric T cell antigen receptor comprises an extracellular domain that binds EGFRvIII, wherein the extracellular domain comprises a humanized or chimeric antibody or antigen-binding portion thereof.

The term "human antibody" refers to antibodies whose variable and constant regions correspond to or are derived from immunoglobulin sequences of the human germ line, as described, for example, by Kabat et al. (see Kabat, et al. (1991) Sequences of Proteins of Immunological Interest, Fifth Edition, U.S. Department of Health and Human Services, NIH Publication No. 91-3242). However, the human antibodies can contain amino acid residues not encoded by human germ line immunoglobulin sequences (for example mutations which have been introduced by random or site-specific mutagenesis in vitro or by somatic mutation in vivo), for example in the CDRs, and in particular in CDR3. Recombinant human antibodies as described herein have variable regions and may also contain constant regions derived from immunoglobulin sequences of the human germ line (see Kabat, E. A., et al. (1991) Sequences of Proteins of Immunological Interest, Fifth Edition, U.S. Department of Health and Human Services, NIH Publication No. 91-3242). According to particular embodiments, however, such recombinant human antibodies are subjected to in-vitro mutagenesis (or to a somatic in-vivo mutagenesis, if an animal is used which is transgenic due to human Ig sequences) so that the amino acid sequences of the VH and VL regions of the recombinant antibodies are sequences which although related to or derived from VH and VL sequences of the human germ line, do not naturally exist in vivo within the human antibody germ line repertoire. According to particular embodiments, recombinant antibodies of this kind are the result of selective mutagenesis or back mutation or of both. Preferably, mutagenesis leads to an affinity to the target which is greater, and/or an affinity to non-target structures which is smaller than that of the parent antibody. Generating a humanized antibody from the sequences and information provided herein can be practiced by those of ordinary skill in the art without undue experimentation. In one approach, there are four general steps employed to humanize a monoclonal antibody, see, e.g., U.S. Pat. Nos. 5,585,089; 6,835,823; 6,824,989. These are: (1) determining the nucleotide and predicted amino acid sequence of the starting antibody light and heavy variable domains; (2) designing the humanized antibody, i.e., deciding which antibody framework region to use during the humanizing process; (3) the actual humanizing methodologies/techniques; and (4) the transfection and expression of the humanized antibody.

Usually the CDR regions in humanized antibodies and human antibody variants are substantially identical, and more usually, identical to the corresponding CDR regions in the mouse or human antibody from which they were derived. In some embodiments, it is possible to make one or more 1-27. Table 1 summarizes examples of antibodies that can be used in the compositions and methods described herein.

TABLE 1

SUMMARY OF ANTIBODY TARGETS AND ANTIBODIES

| Polypeptide | Protein SEQ ID NOs: | Antibodies | Antibody SEQ ID NOs: | References |
|---|---|---|---|---|
| CTLA-4 | SEQ ID NO: 3, SEQ ID NO: 8 | ipilimumab (CTLA-4; Bristol Meyers Squibb); tremelimumab (CTLA-4; Medimmune); | SEQ ID NO: 16, SEQ ID NO: 17 | Metzler et al. *Nat Struct Biol.* 1997; US20150283234 |
| PD-1 | SEQ ID NO: 2, SEQ ID NO: 15 | pembrolizumab (PD-1; Merck); nivolumab (PD-1; Bristol Meyers Squibb); AUNP12 (PD-1; Aurigene); | SEQ ID NO: 18, SEQ ID NO: 19, SEQ ID NO: 20, SEQ ID NO: 21 | US2012135408; US2013173223 |
| PD-L1 | SEQ ID NO: 1, SEQ ID NOs: 12-14 | atezolizumab (PD-L1; Genentech); MPDL3280A (PD-L1; Roche); MEDI4736 (PD-L1; AstraZeneca); MSB0010718C (PD-L1; EMD Serono); avelumab (PD-L1; Merck); MSB0010718C (PD-L1; EMD Serono); durvalumab (PD-L1; Medimmune); | SEQ ID NO: 22 SEQ ID NO: 23 | US8217149B2 |
| TIM-3 | SEQ ID NO: 4, SEQ ID NO: 10 | TSR-022 (TIM3; Tesaro) | SEQ ID NO: 24; SEQ ID NO: 25 | WO2018129553A1 |
| LAG-3 | SEQ ID NO: 5, SEQ ID NO: 11 | IMP321 (LAG3: Immuntep); BMS-986016 (LAG3; Bristol Meyers Squibb); | See Sequences in US20110150892A1 | US9579382B2; US20110150892A1 |
| TIGIT | SEQ ID NOs: 6-7 | Anti-Tigit (Compugen Ltd) | See Sequences (e.g. SEQ ID NOs: 160 and 165) in US20180280506A1 | US20180280506A1 |
| EGFRvIII | SEQ ID NOs: 26-27 | Anti-EGFRvIII (University of Pennsylvania, Novartis Inst for BioMedical Res Inc.) | See Sequences (e.g. SEQ ID NO: 11) in US20140322275A1 | US20140322275A1 | conservative amino acid substitutions of CDR residues without appreciably affecting the binding affinity of the resulting humanized immunoglobulin or human antibody variant. In some embodiments, substitutions of CDR regions can enhance binding affinity.

In some embodiments, the antibody is a nanobody. As used herein, a "nanobody" refers to a single-domain antibody comprising a single monomeric variable antibody domain. A nanobody selectively binds to a specific antigen, similar to an antibody. A nanobody is typically small in size, ranging from 12-15 kDa. Methods for designing and producing nanobodies are known in the art and are further described in Ghahroudi, *FEBS Letters*. September 1997, 414:3 (521-526), which is incorporated herein in its entirety by reference.

In some embodiments, the checkpoint inhibitor polypeptide as described herein comprises an antibody or antigen-binding domain thereof that binds a checkpoint polypeptide selected from the group consisting of PD-L1, PD-1, CTLA-4, TIM-3, LAG-3, or TIGIT. In some embodiments, the antibody binds to an amino acid sequence complimentary to any one of the sequences described herein SEQ ID NO:

Genetically Modified Mesenchymal Stem Cells

A mesenchymal stem cell (MSC) is a self-renewing, multipotent stem cell that comprises the capacity to differentiate into various cell types including, but not limited to, white adipocytes, brown adipocytes, myoblast, skeletal muscle, cardiac muscle, smooth muscle, chondrocytes, and a mature osteoblast upon introduction of proper differentiation cues. An MSC can be produced using techniques known in the art, for example, by a process comprising obtaining a cell by dispersing an embryonic stem (ES) cell colony and culturing the cell with MSC conditioned media. A population of MSCs can be confirmed by assessing the surface markers of the MSC population. For example, at a minimum, 95% or more of an MSC cell population expresses CD73/5'-Nucleotidase, CD90/Thy1, and CD105/Endoglin, and 2% or less of an MSC cell population expresses CD34, CD45, CD11b/Integrin alpha M or CD14, CD79 alpha or CD19, and HLA Class II. The expression of these surface markers can be assessed using techniques known in the art, e.g., FACS analysis.

MSCs can be easily extracted and, given their propensity to move to the site of tumors, are useful for the delivery of therapeutics to said tumors and tumor microenviroments. MSCs tumor tropism (movement to the site of a tumor) is thought to be driven by paracrine signaling between the tumor microenvironment and the corresponding receptors on the cell surface of the MSC. Further discussion of MSCs therapeutic uses is found, for example, in Sage et al., *Cytotherapy* 18: 1435-1445 (2016).

MSCs recruit monocytes, T cells and dendritic cells to sites of inflammation following an infection or injury (e.g., tumor resection) via expression of chemokine (C—C motif) ligand 2 (CCL2, as known as MCP-1 and small inducible cytokine A2). CCL2 sequences are known for a number of species, e.g., human CD28 (NCBI Gene ID: 6347). CCL2 can refer to human CCL2, including naturally occurring variants and alleles thereof. In some embodiments of, e.g., in veterinary applications, CCL2 can refer to the CCL2 of, e.g., dog, cat, cow, horse, pig, and the like. Homologs and/or orthologs of human CCL2 are readily identified for such species by one of skill in the art, e.g., using the NCBI ortholog search function or searching available sequence data for a given species for sequence similar to a reference CCL2 sequence. It is contemplated that an MSC genetically modified to express increased levels of CCL2 (compared to wild-type CCL2 levels) will have a greater capacity to recruit T cells to the site of injury (e.g., tumor resection) compared to a wild-type MSC.

In one embodiment, a cell (e.g., a T cell, or MSC) is genetically modified to express a polypeptide comprising an immunomodulator. An "immunomodulator" refers to an agent with the capacity to modify the immune system of a subject, for example, the polypeptide can induce, amplify, attenuate, or prevent an immune response. It should be understood that while any antigen can be an immunomodulator in the sense that it induces an immune response, an "immunomodulator" as the term is used herein modifies the immune microenvironment of a tumor, e.g., in terms of recruitment of immune effectors, activity of immune effectors, or suppression of immunosuppressive factors, their expression, or their activity. Immunomodulators can be naturally occurring (for example a regulatory T cell, or cell signaling molecules), or engineered (e.g., immunotherapies). Exemplary immunomodulators include, e.g., check point inhibitors, afutuzumab (available from Roche®), pegfilgrastim (Neulasta®), IL-12, IL-2, IL-5, IL-15, TRAIL, EGFR nanobody-TRAIL fusion, Thrombospondin (TSP)-1, interferon α, interferon β, interferon γ, HSV-TK, cytosine deaminase (CD), oncolytic viruses such as oHSV, oHSV-TRAIL, oHSV-GMCSF, or adenovirus.

In one embodiment, the immunomodulatory peptide potentiates cancer cell killing. As used herein, "potentiates cancer cell killing" refers to the increased capacity for a cancer cell to be killed by a genetically modified T cell in the presence of a genetically modified MSC comprising an immunodulatory polypeptide compared to the capacity for a cancer cell to be killed by a genetically modified T cell either alone, or alternatively, in the presence of an MSC that does not comprise an immunodulatory polypeptide.

The presence of an immunomodulatory peptide as described herein increases the efficacy of a genetically modified T cell to kill a cancer cell.

In one embodiment, the immunomodulatory polypeptide is a checkpoint inhibitor polypeptide. In one embodiment, the checkpoint inhibitor polypeptide is an antibody, antibody reagent, or an antigen-binding fragment thereof that specifically binds to at least one immune checkpoint polypeptide. Common checkpoints that are targeted for therapeutics include, but are not limited to PD-1, TIGIT, CTLA4, TIM3, LAG3 and PD-L1. Inhibitors of their checkpoint activities are known in the art. Non-limiting examples of checkpoint inhibitors (with checkpoint targets and manufacturers noted in parentheses) can include: MGA271 (B7-H3: MacroGenics); ipilimumab (CTLA-4; Bristol Meyers Squibb); pembrolizumab (PD-1; Merck); nivolumab (PD-1; Bristol Meyers Squibb); atezolizumab (PD-L1; Genentech); galiximab (B7.1; Biogen); IMP321 (LAG3: Immuntep); BMS-986016 (LAG3; Bristol Meyers Squibb); SMB-663513 (CD137; Bristol-Meyers Squibb); PF-05082566 (CD137; Pfizer); IPH2101 (KIR; Innate Pharma); KW-0761 (CCR4; Kyowa Kirin); CDX-1127 (CD27; CellDex); MEDI-6769 (Ox40; MedImmune); CP-870,893 (CD40; Genentech); tremelimumab (CTLA-4; Medimmune); pidilizumab (PD-1; Medivation); MPDL3280A (PD-L1; Roche); MEDI4736 (PD-L1; AstraZeneca); MSB0010718C (PD-L1; EMD Serono); AUNP12 (PD-1; Aurigene); avelumab (PD-L1; Merck); durvalumab (PD-L1; Medimmune); TSR-022 (TIM3; Tesaro). In one embodiment, a checkpoint inhibitor polypeptide comprises an antibody or antigen-binding reagent thereof that binds PD-L1.

As used herein, "PD-1" or "programmed cell death 1" or "cluster of differentiation 279" or CD279" is a surface receptor protein that suppresses the immune system expressed by T cells and pro-B cells. PD-1 is encoded by the PDCD-1 gene (Gene ID: 5133). Sequences for PD-1 are known for a number of species, e.g., human PD-L1 mRNA sequences (e.g., NM_005018.2) and polypeptide sequences (e.g., NP_005009.2, SEQ ID NO: 2), as well as murine PD-1 polypeptide sequences (e.g., NP_032824.1, SEQ ID NO: 15), together with any naturally occurring allelic, splice variants, and processed forms thereof.

As used herein, "PD-L1" or "programmed cell death 1 ligand 1" or "cluster of differentiation 274" or CD274" or "B7 homolog 1" or "B7-H1" is a protein that suppresses the immune system expressed by T cells, natural killer cells, macrophages, myeloid dendritic cells, epithelial cells, B-cells, and vascular endothelial cells. PD-L1 is encoded by the PD-L1 gene (Gene ID: 29126). Sequences for PD-L1 are known for a number of species, e.g., human PD-L1 isoforms a, b, and c mRNA sequences (e.g., the PD-L1 NCBI Reference Sequences are NM_014143.3, NM_001267706.1, NR_052005.1) and polypeptide sequences (e.g., NP_054862.1, SEQ ID NO: 1, 001254635.1, SEQ ID NO: 12, and NP_001300958.1, SEQ ID NO: 13), as well as murine PD-L1 polypeptide sequences (e.g., NP_068693.1, SEQ ID NO: 14), together with any naturally occurring allelic, splice variants, and processed forms thereof.

Binding of PD-L1 to its receptor, PD-1, transmits an inhibitory signal that reduces the proliferation of T cells and can induce apoptosis. Aberrant PD-L1 and/or PD-1 signalling has been shown to promote cancer cell evasion in various tumors. PD-L1/PD-1 blockade can be accomplished by a variety of mechanisms including antibodies that bind PD-1 or its ligand, PD-L1. Examples of PD-1 and PD-L1 blockers are described in U.S. Pat. Nos. 7,488,802; 7,943,743; 8,008,449; 8,168,757; 8,217,149, and PCT Published Patent Application Nos: WO03042402, WO2008156712, WO2010089411, WO2010036959, WO2011066342, WO2011159877, WO2011082400, and WO2011161699; which are incorporated by reference herein in their entireties. In certain embodiments, the PD-1 inhibitors include anti-PD-L1 antibodies. PD-1 inhibitors include anti-PD-1 antibodies and similar binding proteins such as anti-PD-1 antibody clone RMP1-14, nivolumab (MDX 1106, BMS 936558, ONO 4538), a fully human IgG4 antibody that binds to and blocks the activation of PD-1 by its ligands PD-L1 and PD-L2; lambrolizumab (MK-3475 or SCH 900475), a humanized monoclonal IgG4 antibody against PD-1; CT-011 a humanized antibody that binds PD-1; AMP-224, a fusion protein of B7-DC; an antibody Fc portion; BMS-936559 (MDX-1105-01) for PD-L1 (B7-H1) blockade.

As used herein, "TIGIT" or "T-Cell Immunoreceptor With Ig And ITIM Domains" refers to an immunoglobin protein of the PVR (poliovirus receptor) family encoded by the TIGIT gene. Sequences for TIGIT are known for a number of species, e.g., human TIGIT (the TIGIT NCBI Gene ID is 201633) mRNA sequences (e.g., NM_173799.3), and polypeptide sequences (e.g., NP_776160.2, SEQ ID NO: 6), as well as murine TIGIT polypeptide sequences (e.g., NP_001139797.1, SEQ ID NO: 7), together with any naturally occurring allelic, splice variants, and processed forms thereof. Anti-TIGIT antibodies are known in the art and described herein, for example, in Table 1 and references therein.

Nucleic acids encoding the binding domains of any of the checkpoint inhibitor antibodies described herein or known in the art can be used to engineer the expression of a checkpoint inhibitor by an MSC as described herein. Similarly, nucleic acids encoding the binding domains of a tumor antigen-binding antibody as described herein or as known in the art can be used to engineer the expression of a chimeric T cell antigen receptor as described herein.

As used herein, "CTLA-4" or "cytotoxic T-lymphocyte-associated protein 4" or "CD152" refers to a protein receptor that down regulates immune responses and is constitutively expressed by regulatory T cells. CTLA-4 is encoded by the CTLA-4 gene (Gene ID: 1493). Sequences for CTLA-4 are known for a number of species, e.g., human CTLA-4 mRNA sequences (e.g., NM_005214.5), and polypeptide sequences (e.g., NP_005205.2, SEQ ID NO: 3) as well as murine CTLA-4 polypeptide sequences (e.g., NP_033973.2, SEQ ID NO: 8), together with any naturally occurring allelic, splice variants, and processed forms thereof. Anti-CTLA-4 antibodies are known in the art and described herein, for example, in Table 1 and references therein.

As used herein, "TIM-3" or "T-cell immunoglobulin and mucin-domain containing-3" or "Hepatitis A virus cellular receptor" or "HAVCR2" refers to a cell surface protein expressed by CD4+ Th1 and CD8+ Tc1 cells that mediates T cell exhaustion and loss of function. TIM-3 is encoded by the HAVCR2 gene (Gene ID: 84868). Sequences for TIM-3 are known for a number of species, e.g., human TIM-3 mRNA sequences (e.g., NM_032782.4), and polypeptide sequences (e.g., NP_116171.3, SEQ ID NO: 4 and SEQ ID NO: 9) as well as murine TIM-3 polypeptide sequences (e.g., NP_599011.2, SEQ ID NO: 10), together with any naturally occurring allelic, splice variants, and processed forms thereof. Anti-TIM-3 antibodies are known in the art and described herein, for example, in Table 1 and references therein.

As used herein, "LAG-3" or "lymphocyte-activation gene 3" or "cluster of differentiation 223" or "CD223" refers to a cell surface molecule that negatively regulates cell proliferation, activation, and homeostasis of T cells in a similar mechanism to PD-1 and CTLA-4. LAG-3 is expressed by activated T cells, natural killer cells, B cells, and plasmacytoid dendritic cells. LAG-3 is encoded by the LAG3 gene (Gene ID: 3902). Sequences for LAG-3 are known for a number of species, e.g., human LAG-3 mRNA sequences (e.g., NM_002286.5), and polypeptide sequences (e.g., NP_002277.4, SEQ ID NO: 5) as well as murine LAG-3 polypeptide sequences (e.g., NP_002277.4, SEQ ID NO: 11), together with any naturally occurring allelic, splice variants, and processed forms thereof. Anti-LAG-3 antibodies are known in the art and described herein, for example, in Table 1 and references therein.

In one embodiment, a second genetically modified MSC is engineered to deliver a heterologous polypeptide comprising a cytokine, (e.g., Interleukin (IL)-12B (NCBI Gene ID: 3593), IL-2 (NCBI Gene ID: 3558), IL-5 (NCBI Gene ID: 3567), IL-15 (NCBI Gene ID: 3600), TNF-related apoptosis-inducing ligand (TRAIL; also known as TNF superfamily member 10, TL2, CD253, or TNLG6A; NCBI Gene ID: 8743), an EGFR nanobody-TRAIL fusion, Thrombospondin (THBS)-1 (NCBI Gene ID: 7057), an interferon (e.g., interferon α-1 (NCBI Gene ID: 3439), interferon β-1 (NCBI Gene ID: 3456), or interferon γ (NCBI Gene ID: 3458)), Herpes simplex virus-1 Thymidine kinase (HSV-TK; NCBI Gene ID: 7083), or cytosine deaminase (e.g., *E. coli* (CD; NCBI Gene ID: 944996). Unless otherwise noted, these polypeptides can refer to human polypeptides, including naturally occurring variants and alleles thereof. In some embodiments of, e.g., in veterinary applications, the polypeptides can refer to the polypeptides of, e.g., dog, cat, cow, horse, pig, and the like. Homologs and/or orthologs of these polypeptides are readily identified for such species by one of skill in the art, e.g., using the NCBI ortholog search function or searching available sequence data for a given species for sequence similar to a given reference sequence.

It is also contemplated that an MSC can be used to deliver an oncolytic virus, e.g., an oncolytic HSV, adenovirus, or other oncolytic construct. Delivery of oncolytic viruses is further described in Application Nos. PCT/US2013/031,949 and PCT/2014/069,734, which are incorporated herein by reference in their entireties. Non-limiting examples of oncolytic viruses include oncolytic Herpes Simplex Viruses (oHSV), HSV-TRAIL, and oHSV-granulocyte-macrophage colony-stimulating factor (GMC SF).

Local Cell Delivery and Matrix Encapsulation

Local delivery of cells, whether genetically modified MSCs as described herein or CAR-T's as described herein, can provide benefits for cancer therapy. In one aspect, local delivery can provide a high local concentration of the therapeutic polypeptide(s) or effector cells. However, one of the benefits of CAR-T therapy is that the targeting moiety on the chimeric receptor permits localization to the cancer cells via systemic delivery, and one of the benefits of MSCs to deliver therapeutic polypeptides to the tumor microenvironment is their natural tumor-homing activity. These benefits of systemic administration can be hampered for certain tumor types, notably brain tumors, where the blood-brain barrier can limit access of systemically administered cells to a tumor. For this reason, local delivery to the site of a tumor, and especially considering the immunostimulatory effects of tumor resection demonstrated herein, local delivery of therapeutic cells to the site of tumor resection, can be of particular benefit for the treatment of brain tumors, including but not limited to GBM, which are notoriously difficult to treat.

In one embodiment, the genetically modified MSCs are encapsulated in a matrix. In another embodiment, the CAR-T cells are encapsulated in a matrix. In another embodiment, both the MSCs and the CAR-T cells are encapsulated in a matrix. This can assist in retaining MSCs in a given location, such as a tumor resection cavity. The matrix can minimize wash out of cells from the resection cavity, e.g., by CSF in the case of brain tumors.

A matrix useful in the methods and compositions described herein will permit MSCs and/or CAR-T's to migrate away from the matrix, rather than containing the cells within the matrix permanently. As used herein, "matrix" refers to a biological material that comprises a "biocompatible substrate" that can be used as a material that is suitable for implantation into a subject or into which a cell population can be deposited. A biocompatible substrate does not cause toxic or injurious effects once implanted in the subject. The biocompatible substrate can but need not necessarily provide the supportive framework that allows cells to attach to it, and grow on it. Cultured populations of cells (e.g., genetically modified MSCs or CAR-Ts) can be prepared with the biocompatible substrate (i.e., the matrix), which provides the appropriate interstitial distances required, e.g., for cell-cell interaction. As used herein, "encapsulated" refers to a cell that is enclosed within the matrix.

A matrix can be used to aid in further controlling and directing a cell or population of genetically modified MSCs and CAR T cells as described herein. A matrix can be designed or selected to provide environmental cues to control and direct the migration of cells to a site of injury or disease. A structure can be engineered from a nanometer to micrometer to millimeter to macroscopic length, and can further comprise or be based on factors such as, but not limited to, material mechanical properties, material solubility, spatial patterning of bioactive compounds, spatial patterning of topological features, soluble bioactive compounds, mechanical perturbation (cyclical or static strain, stress, shear, etc.), electrical stimulation, and thermal perturbation.

In one embodiment, the matrix comprises a synthetic matrix. In one embodiment, the matrix comprises a thiol-modified hyaluronic acid and a thiol-reactive cross-linker molecule. In one embodiment, the thiol-reactive cross-linker molecule is polyethylene glycol diacrylate. Further description of components useful in constructing a matrix, as well as instruction for making a matrix, can be found in U.S. patent application Ser. No. 15/225,202, which is incorporated herein in its entirety by reference.

Methods of encapsulation of stem cells are known in the art and can be found, for example, in Shah et al. *Biomatter.* 2013 and Kauer et al. *Nature Neuroscience.* 2013.

For example, the synthetic extracellular matrix (ECM) components, such as those from Hystem and Extralink (Glycosan Hystem-C, Biotime Inc.), can be reconstituted according to the manufacturer's protocols. Stem cells (e.g. $1\times10^5$, $2\times10^5$ or $4\times10^5$ cells) can be re-suspended in Hystem (e.g. 14 µl) and the matrix is cross-linked by adding Extralink (e.g. 6 µl). After about 20 minutes (gelation time) at 25° C., the stein cell and ECM hydrogel can be placed in the center of different sizes (35 or 60 mm) of glass-bottomed dish. Bioluminescence imaging can be used to determine the viability of the MSCs expressing a detectable label. To assess the numbers of cells expressing immunomodulatory polypeptides and the amounts of such polypeptides expressed, methods known in the art can be used such as flow cytometry, Western blotting, immunohistochemistry, or enzyme-linked immunosorbent assay (ELISA).

Detectable Labels

For tracking purposes, cells can be tagged with a detectable label. As used herein, the term "detectable label" refers to a composition capable of producing a detectable signal indicative of the presence of a target. Detectable labels include any composition detectable by spectroscopic, photochemical, biochemical, immunochemical, electrical, optical or chemical means. Suitable labels include fluorescent molecules, radioisotopes, nucleotide chromophores, enzymes, substrates, chemiluminescent moieties, biluminescent moieties, and the like. As such, a label is any composition detectable by spectroscopic, photochemical, biochemical, immunochemical, electrical, optical or chemical means needed for the methods and devices described herein.

A wide variety of fluorescent reporter dyes are known in the art. Typically, the fluorophore is an aromatic or heteroaromatic compound and can be a pyrene, anthracene, naphthalene, acridine, stilbene, indole, benzoindole, oxazole, thiazole, benzothiazole, cyanine, carbocyanine, salicylate, anthranilate, coumarin, fluorescein, rhodamine or other like compound.

Exemplary fluorophores include, but are not limited to, 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein (pH 10); 5-Carboxytetramethylrhodamine (5-TAMRA); 5-FAM (5-Carboxyfluorescein); 5-Hydroxy Tryptamine (HAT); 5-ROX (carboxy-X-rhodamine); 5-TAMRA (5-Carboxytetramethylrhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Aequorin (Photoprotein); Alexa Fluor 350™; Alexa Fluor 430™; Alexa. Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC, AMCA-S; AMCA (Aminomethylcoumarin); AMCA-X; Aminoactinomycin D; Aminocoumarin; Anilin Blue; Anthrocyl stearate; APC-Cy7; APTS; Astrazon Brilliant Red 4G; Astrazon Orange R; Astrazon Red 6B; Astrazon Yellow 7 GLL; Atabrine; ATTO-TAGTM CBQCA; ATTO-TAG™ FQ; Auramine; Aurophosphine G; Aurophosphine; BAO 9 (Bisaminophenyloxadiazole); BCECF (high pH); BCECF (low pH); Berberine Sulphate; Beta Lactamase; BFP blue shifted GFP (Y66H); BG-647; Bimane; Bisbenzamide; Blancophor FFG; Blancophor SV; BOBO™-1; BOBO™-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; Calcein; Calcein Blue; Calcium Crimson™; Calcium Green; Calcium Green-1 Ca2+ Dye; Calcium Green-2 Ca2+; Calcium Green-5N Ca2+; Calcium Green-C18 Ca2+; Calcium Orange; Calcofluor White; Carboxy-X-rhodamine (5-ROX); Cascade Blue™; Cascade Yellow; Catecholamine; CFDA; CFP—Cyan Fluorescent Protein; Chlorophyll; Chromomycin A; Chromomycin A; CMFDA; Coelenterazine; Coelenterazine cp; Coelenterazine f; Coelenterazine fcp; Coelenterazine h; Coelenterazine hcp; Coelenterazine ip; Coelenterazine O; Coumarin Phalloidin; CPM Methylcoumarin; CTC; Cy2™; Cy3.1 8; Cy3.5™; Cy3™; Cy5.1 8; Cy5.5™; Cy5™; Cy7™; Cyan GFP; cyclic AMP Fluorosensor (FiCRhR); d2; Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3; DCFDA; DCFH (Dichlorodihydrofluorescein Diacetate); DDAO; DHR (Dihydrorhodamine 123); Di-4-ANEPPS; Di-8-ANEPPS (non-ratio); DiA (4-Di-16-ASP); DIDS;

Dihydrorhodamine 123 (DHR); DiO (DiOC18(3)); DiR; DiR (DiIC18(7)); Dopamine; DsRed; DTAF; DY-630-NHS; DY-635-NHS; EBFP; ECFP; EGFP; ELF 97; Eosin; Erythrosin; Erythrosin ITC; Ethidium homodimer-1 (EthD-1); Euchrysin; Europium (III) chloride; Europium; EYFP; Fast Blue; FDA; Feulgen (Pararosaniline); FITC; FL-645; Flazo Orange; Fluo-3; Fluo-4; Fluorescein Diacetate; Fluoro-Emerald; Fluoro-Gold (Hydroxystilbamidine); Fluor-Ruby; FluorX; FM 1-43™; FM 4-46; Fura Red™ (high pH); Fura-2, high calcium; Fura-2, low calcium; Genacryl Brilliant Red B; Genacryl Brilliant Yellow 10GF; Genacryl Pink 3G; Genacryl Yellow 5GF; GFP (S65T); GFP red shifted (rsGFP); GFP wild type, non-UV excitation (wtGFP); GFP wild type, UV excitation (wtGFP); GFPuv; Gloxalic Acid; Granular Blue; Haematoporphyrin; Hoechst 33258; Hoechst 33342; Hoechst 34580; HPTS; Hydroxycoumarin; Hydroxystilbamidine (FluoroGold); Hydroxytryptamine; Indodicarbocyanine (DiD); Indotricarbocyanine (DiR); Intrawhite Cf; JC-1; JO-JO-1; JO-PRO-1; LaserPro; Laurodan; LDS 751; Leucophor PAF; Leucophor SF; Leucophor WS; Lissamine Rhodamine; Lissamine Rhodamine B; LOLO-1; LO-PRO-1; Lucifer Yellow; Mag Green; Magdala Red (Phloxin B); Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxadidole; Noradrenaline; Nuclear Fast Red; Nuclear Yellow; Nylosan Brilliant lavin E8G; Oregon Green™; Oregon Green 488-X; Oregon Green™ 488; Oregon Green™ 500; Oregon Green™ 514; Pacific Blue; Pararosaniline (Feulgen); PE-Cy5; PE-Cy7; PerCP; PerCP-Cy5.5; PE-TexasRed (Red 613); Phloxin B (Magdala Red); Phorwite AR; Phorwite BKL; Phorwite Rev; Phorwite RPA; Phosphine 3R; PhotoResist; Phycoerythrin B [PE]; Phycoerythrin R [PE]; PKH26; PKH67; PMIA; Pontochrome Blue Black; POPO-1; POPO-3; PO-PRO-1; PO-PRO-3; Primuline; Procion Yellow; Propidium Iodid (PI); PyMPO; Pyrene; Pyronine; Pyronine B; Pyrozal Brilliant Flavin 7GF; QSY 7; Quinacrine Mustard; Resorufin; RH 414; Rhod-2; Rhodamine; Rhodamine 110; Rhodamine 123; Rhodamine 5 GLD; Rhodamine 6G; Rhodamine B 540; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycoerythrin (PE); red shifted GFP (rsGFP, S65T); S65A; S65C; S65L; S65T; Sapphire GFP; Serotonin; Sevron Brilliant Red 2B; Sevron Brilliant Red 4G; Sevron Brilliant Red B; Sevron Orange; Sevron Yellow L; sgBFP™; sgBFP™ (super glow BFP); sgGFP™; sgGFP™ (super glow GFP); SITS; SITS (Primuline); SITS (Stilbene Isothiosulphonic Acid); SPQ (6-methoxy-N-(3-sulfopropyl)-quinolinium); Stilbene; Sulphorhodamine B can C; Sulphorhodamine G Extra; Tetracycline; Tetramethylrhodamine; Texas Red™; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC (TetramethylRodamineIsoThioCyanate); True Blue; TruRed; Ultralite; Uranine B; Uvitex SFC; wt GFP; WW 781; XL665; X-Rhodamine; XRITC; Xylene Orange; Y66F; Y66H; Y66W; Yellow GFP; YFP; YO-PRO-1; YO-PRO-3; YOYO-1; and YOYO-3. Many suitable forms of these fluorescent compounds are available and can be used.

Other exemplary detectable labels include luminescent and bioluminescent markers (e.g., biotin, luciferase (e.g., bacterial, firefly, click beetle and the like), luciferin, and aequorin), radiolabels (e.g., 3H, 125I, 35S, 14C, or 32P), enzymes (e.g., galactosidases, glucorinidases, phosphatases (e.g., alkaline phosphatase), peroxidases (e.g., horseradish peroxidase), and cholinesterases), and calorimetric labels such as colloidal gold or colored glass or plastic (e.g., polystyrene, polypropylene, and latex) beads. Patents teaching the use of such labels include U.S. Pat. Nos. 3,817,837, 3,850,752, 3,939,350, 3,996,345, 4,277,437, 4,275,149, and 4,366,241, each of which is incorporated herein by reference.

Means of detecting such labels are well known to those of skill in the art. Thus, for example, radiolabels can be detected using photographic film or scintillation counters, fluorescent markers can be detected using a photo-detector to detect emitted light. Enzymatic labels are typically detected by providing the enzyme with an enzyme substrate and detecting the reaction product produced by the action of the enzyme on the enzyme substrate, and calorimetric labels can be detected by visualizing the colored label Administration In some embodiments, the methods described herein relate to treating a subject having or diagnosed a solid tumor cancer by administering a mammalian cell comprising any of the genetically modified T cell described herein, and a modified MSC that expresses an immunomodulatory polypeptide. In one embodiment, the solid tumor has been resected prior to administration. Subjects having a condition (e.g., glioblastoma) can be identified by a physician using current methods of diagnosing the condition. Symptoms and/or complications of the condition, which characterize these conditions and aid in diagnosis are well known in the art and include but are not limited to, fatigue, persistent infections, and persistent bleeding. Tests that may aid in a diagnosis of, e.g. the condition, but are not limited to, blood screening and imaging (e.g., PET scan), and are known in the art for a given condition. A family history for a condition, or exposure to risk factors for a condition can also aid in determining if a subject is likely to have the condition or in making a diagnosis of the condition.

In one embodiment, the genetically modified MSC described herein are administered directly into the cavity formed by resection of the tumor, and the genetically modified T cells described herein are administered systemically. In another embodiment, the genetically modified MSCs and the genetically modified T cells are administered directly into the cavity formed by resection of the tumor at substantially the same time. In another embodiment, the genetically modified MSCs and the genetically modified T cells are administered systemically at substantially the same time, or at different time points. In yet another embodiment, the genetically modified MSC are administered systemically, and the genetically modified T cells are administered directly into the cavity formed by resection of the tumor. The natural tumor-homing activity of MSCs can assist in the tumor-localization of systemically-administered MSCs.

The compositions described herein can be administered to a subject having or diagnosed as having a condition. In some embodiments, the methods described herein comprise administering an effective amount of activated genetically modified T cells and genetically modified MSCs as described herein to a subject in order to alleviate a symptom of the condition. As used herein, "alleviating a symptom of the condition" is ameliorating any condition or symptom associated with the condition. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. In one embodiment, the compositions described herein are administered systemically or locally. In a preferred embodiment, the compositions described herein are administered intravenously. In another embodiment, the compositions described herein are administered at the site of the tumor or tumor resection.

The term "effective amount" as used herein refers to the amount of genetically modified T cells and genetically modified MSCs needed to alleviate at least one or more symptom of the disease (e.g., glioblastoma), and relates to a sufficient amount of the cell preparation or composition to provide the desired effect. The term "therapeutically effective amount" therefore refers to an amount genetically modified T cells and MSCs that is sufficient to provide a particular anti-condition effect when administered to a typical subject. An effective amount as used herein, in various contexts, would also include an amount sufficient to delay the development of a symptom of the disease, alter the course of a symptom disease (for example but not limited to, slowing the progression of a condition), or reverse a symptom of the condition. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be evaluated by standard pharmaceutical procedures in cell cultures or experimental animals. The dosage can vary depending upon the dosage form employed and the route of administration utilized.

While MSCs will most often be administered locally and CAR T cells systemically, in one aspect, the technology described herein relates to a pharmaceutical composition comprising activated genetically modified T cells and modified MSCs as described herein, and optionally a pharmaceutically acceptable carrier. The active ingredients of the pharmaceutical composition at a minimum comprise genetically modified T cells and genetically modified MSCs as described herein. In some embodiments, the active ingredients of the pharmaceutical composition consist essentially of genetically modified T cells and genetically modified MSCs as described herein. In some embodiments, the active ingredients of the pharmaceutical composition consist of genetically modified T cells and genetically modified MSCs as described herein. Pharmaceutically acceptable carriers for cell-based therapeutic formulation include saline and aqueous buffer solutions, Ringer's solution, and serum component, such as serum albumin, HDL and LDL. The terms such as "excipient", "carrier", "pharmaceutically acceptable carrier" or the like are used interchangeably herein.

In some embodiments, the pharmaceutical composition comprising genetically modified T cells and genetically modified MSCs cells as described herein can be a parenteral dose form. Since administration of parenteral dosage forms typically bypasses the patient's natural defenses against contaminants, the components apart from the genetically modified T cells and genetically modified MSCs themselves are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. Any of these can be added to the preparation of genetically modified T cells and MSCs prior to administration.

Suitable vehicles that can be used to provide parenteral dosage forms of genetically modified T cells and MSCs as disclosed within are well known to those skilled in the art. Examples include, without limitation: saline solution; glucose solution; aqueous vehicles including but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

Dosage

"Unit dosage form" as the term is used herein refers to a dosage suitable for one administration. By way of example a unit dosage form can be an amount of therapeutic disposed in a delivery device, e.g., a syringe or intravenous drip bag. In one embodiment, a unit dosage form is administered in a single administration. In another embodiment, more than one unit dosage form can be administered simultaneously.

A pharmaceutical composition comprising the genetically modified T cells and genetically modified MSCs described herein can generally be administered at a dosage of $10^4$ to $10^9$ cells/kg body weight, in some instances $10^5$ to $10^6$ cells/kg body weight, including all integer values within those ranges. If necessary, genetically modified T cells and/or genetically modified MSCs can also be administered multiple times at these dosages. The cells can be administered by using infusion techniques that are commonly known in immunotherapy (see, e.g., Rosenberg et al., New Eng. J. of Med. 319:1676, 1988).

In certain aspects, it may be desired to administer genetically modified T cells to a subject and then subsequently redraw blood (or have an apheresis performed), activate T cells therefrom as described herein, and reinfuse the patient with these activated and expanded T cells. This process can be carried out multiple times every few weeks. In certain aspects, T cells can be activated from blood draws of from 10 cc to 400 cc. In certain aspects, T cells are activated from blood draws of 20 cc, 30 cc, 40 cc, 50 cc, 60 cc, 70 cc, 80 cc, 90 cc, or 100 cc.

Modes of administration can include, for example intravenous (i.v.) injection or infusion. The compositions described herein can be administered to a patient transarterially, intratumorally, intranodally, or intramedullary. In some embodiments, the compositions of genetically modified T cells and genetically modified MSCs may be injected directly into a tumor, lymph node, or site of infection. In one embodiment, the compositions described herein are administered into a body cavity or body fluid (e.g., ascites, pleural fluid, peritoneal fluid, or cerebrospinal fluid).

The dosage of the above treatments to be administered to a patient will vary with the precise nature of the condition being treated and the recipient of the treatment. The scaling of dosages for human administration can be performed according to art-accepted practices.

In some embodiments, a single treatment regimen is required. In others, administration of one or more subsequent doses or treatment regimens can be performed. For example, after treatment biweekly for three months, treatment can be repeated once per month, for six months or a year or longer. In some embodiments, no additional treatments are administered following the initial treatment. In one embodiment, genetically modified T cells are administered once, and genetically modified MSCs are administered at least one additional time. In one embodiment, genetically modified MSCs are administered once, and genetically modified T cells are administered at least one additional time.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to administer further cells, discontinue treatment, resume treatment, or make other alterations to the treatment regimen. The dosage should not be so large as to cause adverse side effects, such as cytokine release syndrome. Generally, the dosage will vary with the age, condition, and sex of the patient and can be determined by one of skill in the art. The dosage can also be adjusted by the individual physician in the event of any complication.

Table 2 shows non-limiting examples of known tumor antigens associated with a particular cancer type.

TABLE 2

Tumor antigens associated with a given cancer.

| Cancer | Tumor Antigen |
| --- | --- |
| Glioblastoma | EGFRvIII |
| Glioma | HER2 |
| Medulloblastoma | CD133 |
|  | EGFR |
|  | IL13RA2 |
| Melanoma | L1-CAM |
|  | CTAG1B |
|  | GD2 |
| Breast Cancer | HER2 |
| Non-small Cell Lung Cancer | EGFR |

EXAMPLES

Example 1: Dual Stem Cell and CAR-T Based Immune Therapies for Resected Tumors

As tissue damage is known to result in activation of both innate and adaptive immune response 1, flow cytometry analysis indicates a gradual, time-dependent increase in the number of mononuclear cells up to day 6 post-tumor resection. Furthermore, sub-analysis on mononuclear cells indicated that significant numbers of myeloid derived suppressor cells (MDSC) resided within CT2A-Fmc tumors, which were markedly reduced after tumor resection (FIG. 1A). Tumor resection enhanced recruitment of both CD4+ and CD8+ effector T cells into resected area at day 5 post-tumor resection (FIGS. 1B-E). Together, these results indicate that surgical resection of CT2A tumors greatly decreases the number of tumor-associated MDSCs and simultaneously increases the number of effector T lymphocytes recruited into the remaining tumor area. These studies are promising and provide a new platform for testing novel immune based therapeutics in such models.

Figure 2A:
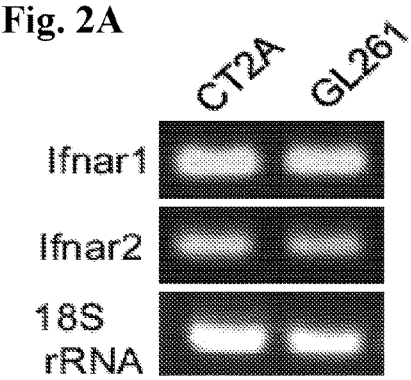
FIG. 2A-E depicts experimental data showing that MSC-IFNβ has dual cytotoxic and immunomodulatory function.
Figure 2B:
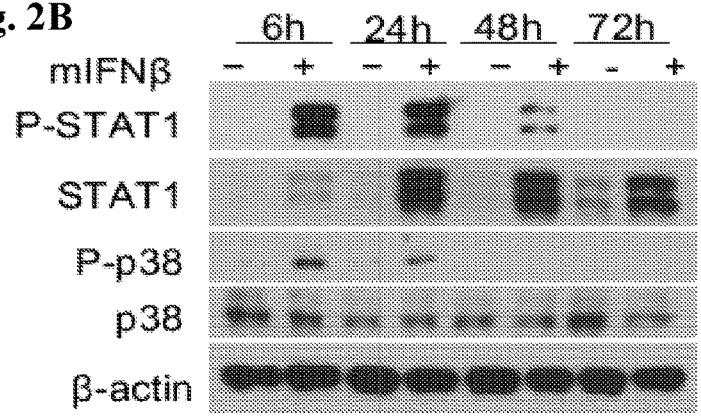
Figure 2C:
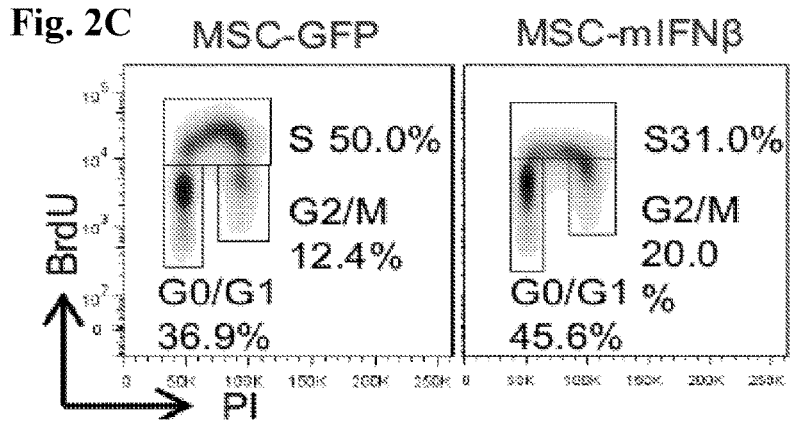
Figure 2D:
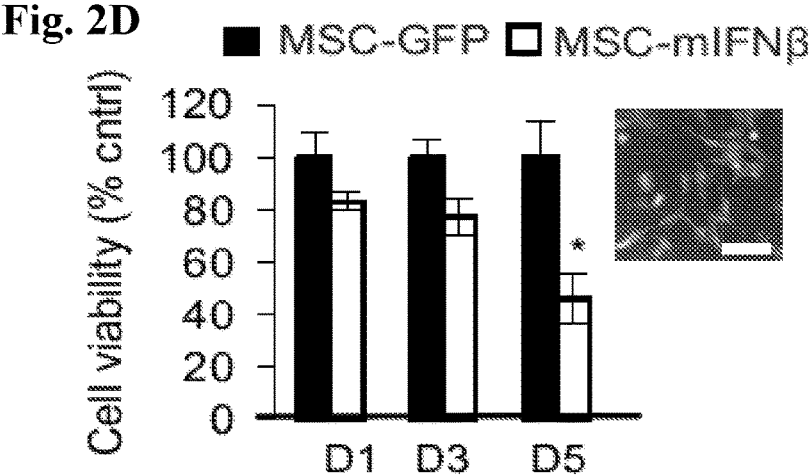
Figure 2E:
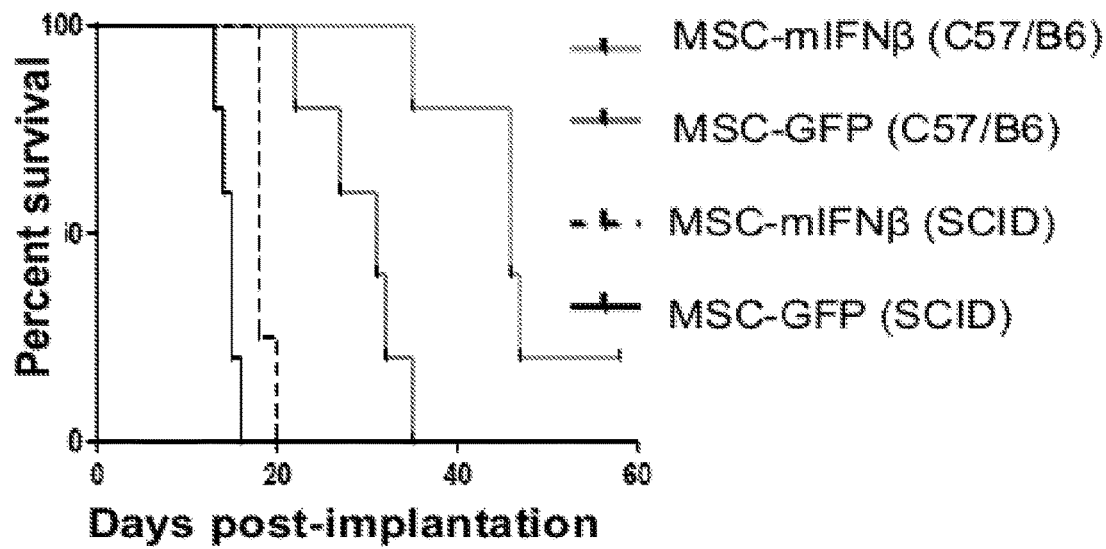
Figure 3A:
FIG. 3A-E depicts experimental data showing that mouse GBM cells express PD-L1 and MSC-ScFv-PD-L1 have antitumor efficacy in resected GBM.
Figure 3B:
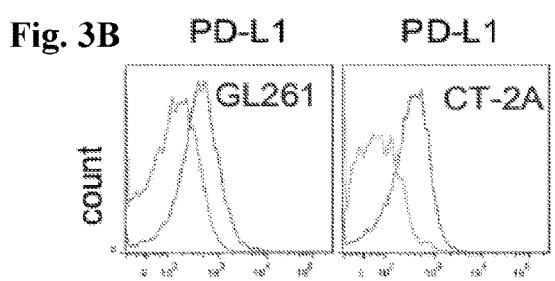
Figure 3C:
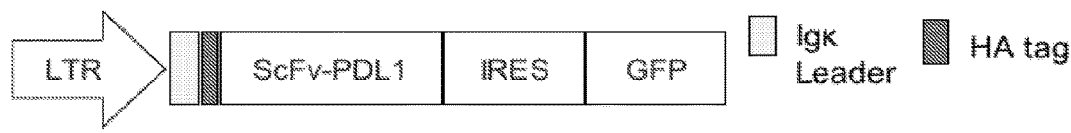
Figure 3D:
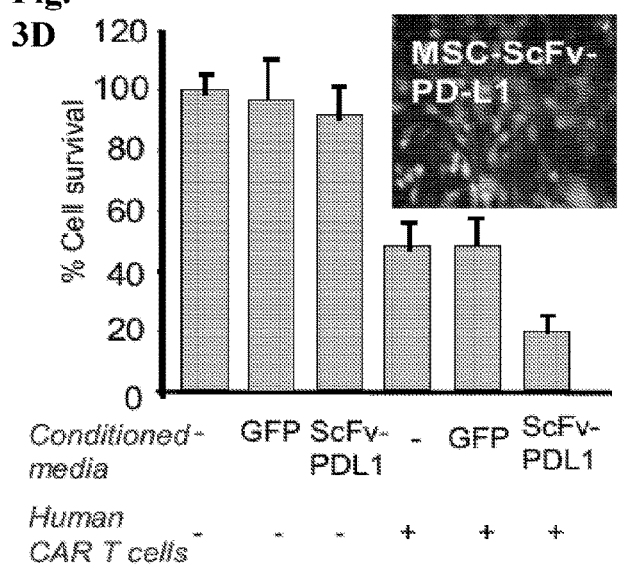
Figure 3E:
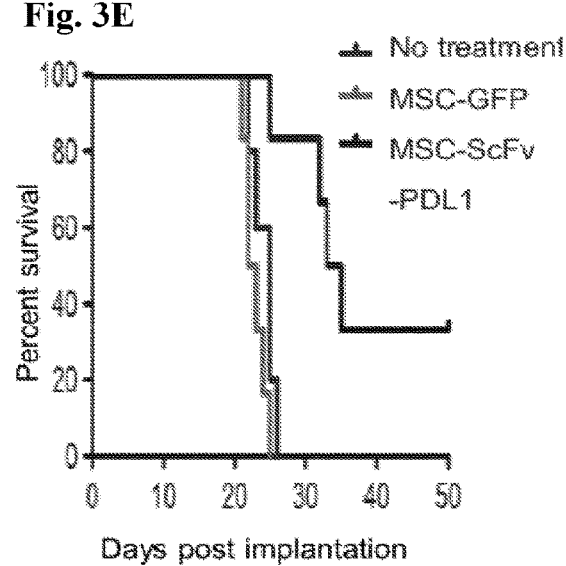

IFNβ belongs to type I interferons that bind to the interferon-α/β cell surface receptor complex (IFNAR)[2] and induces the classical JAK-STAT pathway as well as PI3K and p38 MAPK pathways[3]. A number of pre-clinical studies have shown that IFNβ has direct anti-tumor activity[4-6] and also acts as an immunostimulatory molecule by indirectly provoking an antitumor response via modulation of the immune system[7-9]. However, despite these bi-functional modes of action, the clinical translation of IFNβ treatments for cancer so far has been restricted by its short half-life and systemic toxicity[10-12]. While not wishing to be bound by theory, it was hypothesized that stem cell-based on-site delivery could address the issues related to the short half-life of IFNβ, while achieving therapeutic concentrations locally without causing systemic toxicity[13,14]. Based on this rationale, lenti- and retro-viral vectors were generated bearing a highly secretable variant of human and mouse IFNβ, and mouse MSCs were transduced to express mIFNβ (MSC-mIFNβ). The in vitro data reveal that mouse GBM cells express IFNβ receptors, IFNAR1/2, and MSC-released mIFNβ results in phosphorylation of STAT1 and p38 and suppresses proliferation of mouse GBM via induction of cell cycle arrest (FIG. 2A-D). In vivo, intratumoral injection of MSC-mIFNβ into established CT2A-FmC tumors resulted in a significantly prolonged survival in immunocompetent (C57/B6) as compared to immunocompromised (SCID) mice (FIG. 2E). Based on in vivo findings, the immunomodulatory effects from the direct anti-GBM response of mIFNβ were considered.

PD-L1 expression across different cancer types is seen in a small subset of tumor cells and previous studies have shown only limited correlation between basic PD-L1 expression levels and immune checkpoint blockade efficacy[15,16]. Moreover, GBM are considered immunologically cold and have low levels of T and NK cell infiltrations which might be responsible for their limited PD-L1 levels in GBM. Although IFNβ has bimodal immunomodulatory and cytotoxic functions, it has also been known to upregulate PD-L1 expression on tumor cells via the JAK/STAT/IRF1 signaling pathway[17], thus influencing immune-modulatory function of IFNβ. It has been shown that both recombinant IFNβ and MSC-IFNβ treatment results in the increased PD-L1 expression on GBM tumor cells in culture. This upregulation can be blocked by the use of IFNaR1 blocking antibody, MAR1, 5A3 (FIGS. 5A-B). In vivo, intratumoral implantation of MSC-IFNβ results in the upregulation of PD-L1 on tumor cells as compared to controls (FIG. 5C). These findings are exciting and support the rationale for the combined use of MSC mediated delivery of IFNβ and ScFV-PD-L1 in GBM.

PD-L1 has been identified as a factor associated with poor prognosis in a range of cancers, and was reported to be mainly induced by PTEN loss in GBM[18]. Previous studies have shown that PTEN loss increases PD-L1 expression in colorectal cancer[19] and promotes immune resistance in GBM[20]. Immune checkpoint blockade with monoclonal antibodies targeting PD-1 or PD-L1 has recently shown favorable results in the clinical therapy of multiple cancer types[21,22]. Despite important clinical benefits, systemically delivered anti PD-1 and PD-L1 therapies are associated with a diverse spectrum of immune-related adverse events (irAEs) that are occasionally severe or even fatal[23,24]. Thus, it would be ideal to use MSC that release both IFNβ and ScFV-PDL1 and demonstrate their therapeutic efficacy in mouse tumor cells of GBM.

A retroviral vector was constructed bearing human and mouse specific ScFv-PDL1 encoding murine Ig κ-chain V-J2-C signal peptide and the single chain variable region of the YW234.55.S70 antibody against murine PD-L1 and assessed for its therapeutic in vitro and in vivo. Specifically, mouse GBM express cell surface PD-L1, and MSC engineered to express ScFv-PDL1 (MSC-SCFv-PDL1) suppress tumor growth in vitro (using EGFRvIII CAR T assay) and in vivo and increase survival of mice bearing tumors (FIG. 3A-E). These findings lend validity to the use of MSC delivered immune checkpoint inhibitors in GBM and further strengthen the rationale for the locally-delivered MSC mediated IFNβ and immune checkpoint therapies in resected solid tumors.

Figure 4:
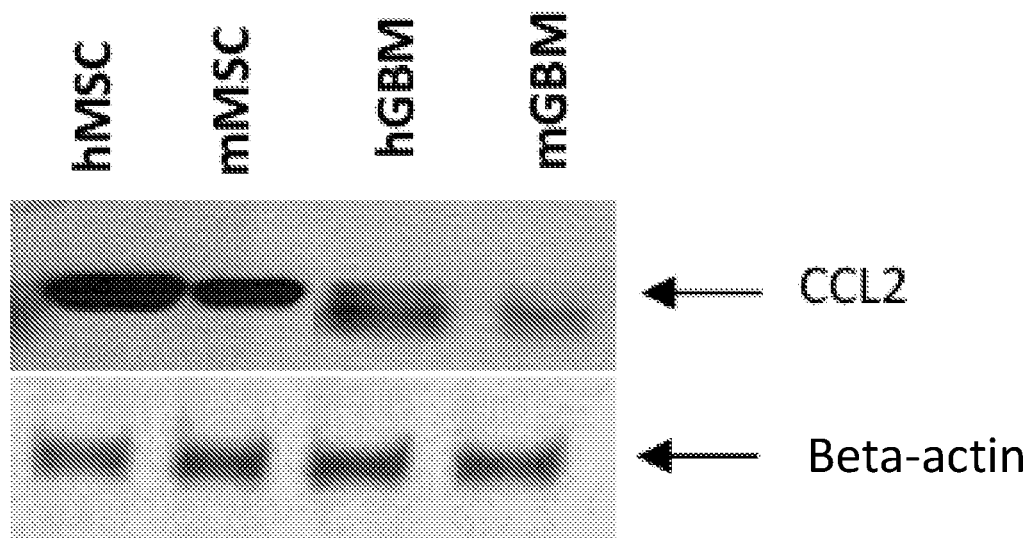
FIG. 4 depicts experimental data showing MSCs expressing CCL-2. Mouse and human MSC and GBM cells were cultured and Western blot analysis was performed using anti CCL2 antibody on the conditioned medium obtained after 24 hours of culturing cells.

Chimeric antigen receptor (CAR) T cells[25] have demonstrated impressive clinical efficacy for a number of hematological cancers, however their success has been limited in solid tumors[26]. Previous studies have developed CARs directed to the mutant variant of cell surface receptor, EGFR (EGFRvIII; known to be specifically expressed in GBM[27]) and shown their efficacy in mouse models of intact GBM[28]. Although these studies offer promise, inadequate recruitment of CAR T cells and their functionality in the immune-evasive environment of tumors[25] remain a serious challenge in developing optimal CAR T therapies for GBM. The chemokine CCL2 is known to play an important role in the recruitment of T cells to tumors[29-31] and recent loss of function studies reveal that MSCs express significant levels of CCL2, allowing their long lasting contact with T cells[32]. It was confirmed that both human and mouse MSC express CCL2 (FIG. 4) and implantation of encapsulated MSC in the tumor resection-cavity can lead to heightened tropism of adoptively transferred CAR T cells. The fate of systemically delivered imageable EGFRvIII-CAR T can be assessed in mouse tumor models of resection.

Figure 6A:
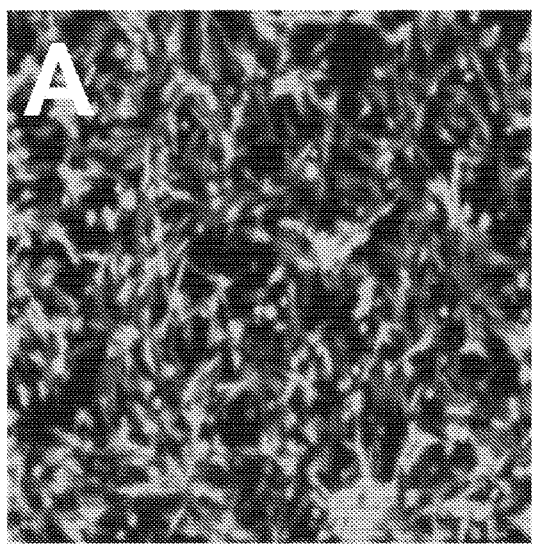
FIG. 6A-F shows MSC mediated IL-12 expression induces CD4 and CD8 T cell response in vitro and influences tumor volumes in vivo.
Figure 6B:
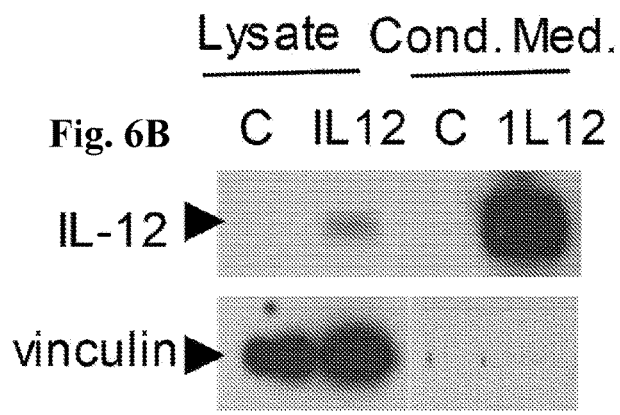
Figure 6C:
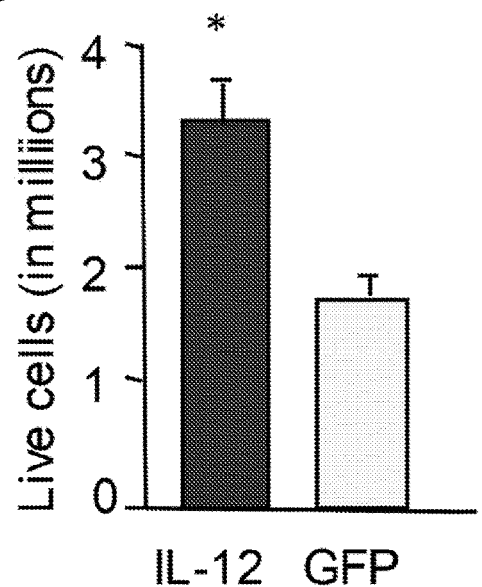
Figure 6D:
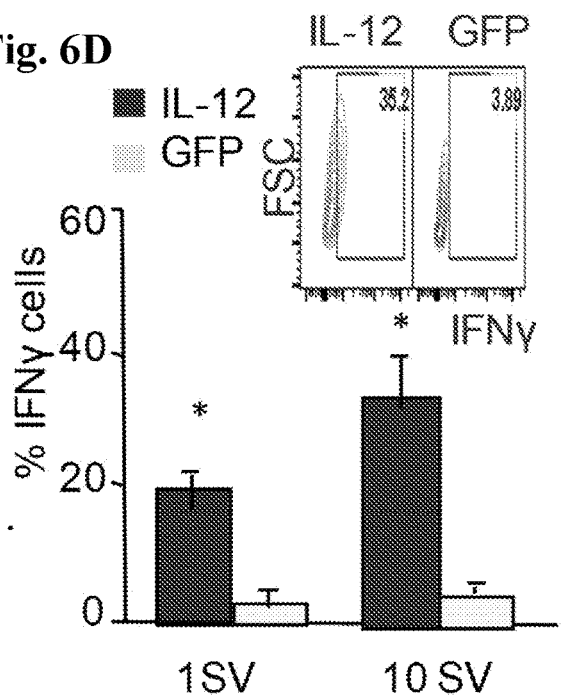
Figure 6E:
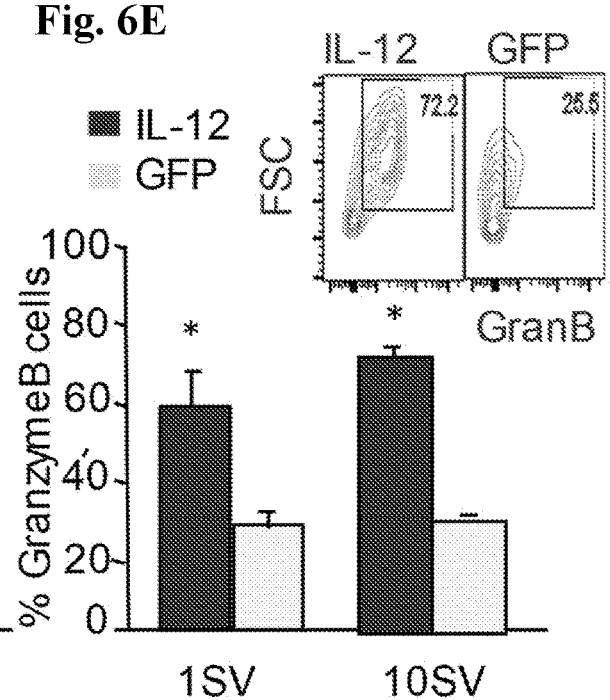
Figure 6F:
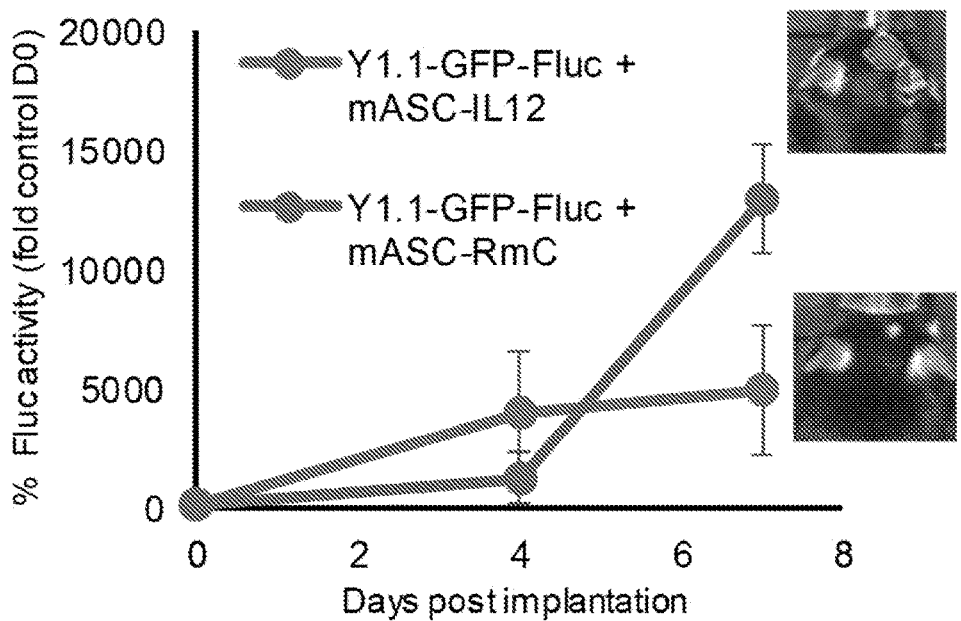

Immunomodulatory cytokines can stimulate vigorous antitumor responses and are candidates for increasing CAR T cell efficacy in solid tumors. While any cytokine that promotes immune cell activation or cytotoxic activity can be of benefit, IL-12 in particular has been explored as a candidate for tumor immunotherapy, due to its ability to activate both innate and adaptive immunity[33]. However, its short half-life, severe side effects associated with systemic administration[42,4333,34] and a very narrow therapeutic benefit have hampered its use in this manner. Described herein are studies that demonstrate the benefit of local delivery of IL-12 directly into the tumor microenvironment. IL-12 is a heterodimeric protein composed of p35 and p40 subunits that bridges the innate and adaptive immune system[35]. IL-12 p35 subunit can homodimerize and IL-12 p40 subunit can associate with IL23a subunit to form IL23[35], therefore bioactive IL-12 requires the expression of both p40 and p35, and correct heterodimer assembly[36]. A dual promoter vector was constructed bearing secretable p35 and p40 subunits of IL-12, separated by a linker sequence that has been optimized previously[37]. Limiting IL-12 expression to within the tumor microenvironment may reduce unwanted toxicity while enhancing CAR T cell functionality; therefore, MSCs were engineered to express and deliver IL-12. The data presented here indicate that MSCs can be readily engineered to express functional IL-12 (FIGS. 6A-E) and MSC-IL-12 significantly influences tumor growth in vivo (FIG. 6F).

Figure 7A:
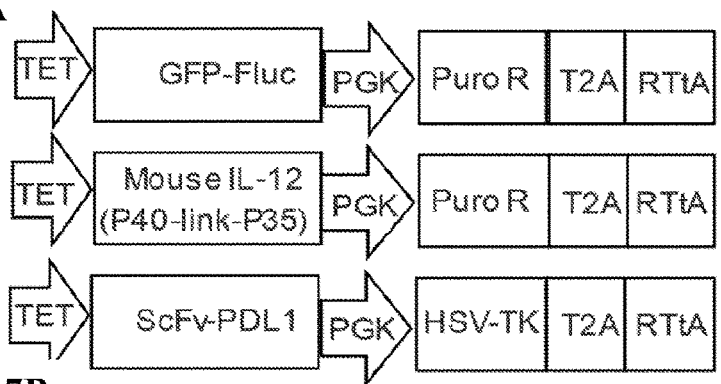
FIG. 7A-D shows efficiency of Tet regulatable system.
Figure 7B:
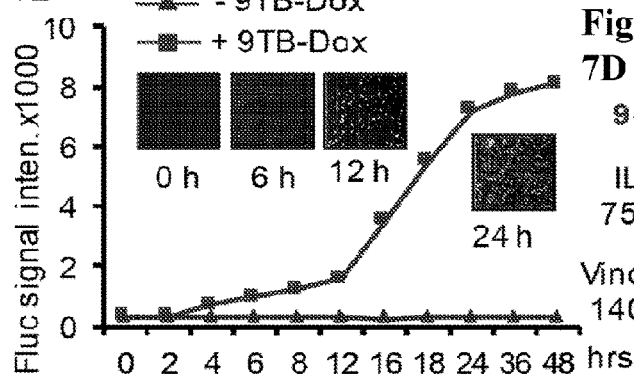
Figure 7C:
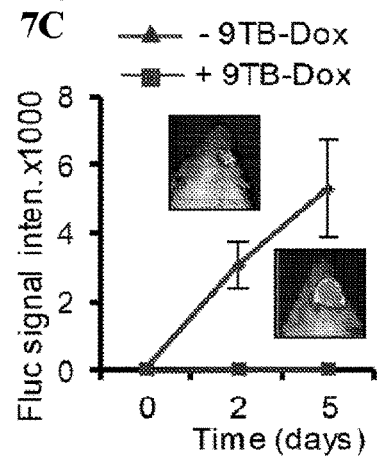
Figure 7D:
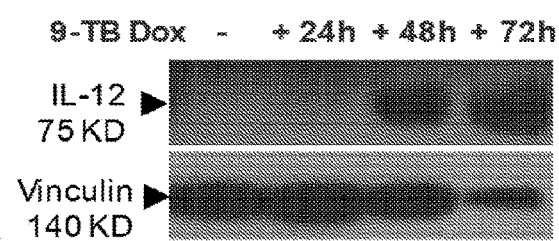

Prolonged treatment with IL-12 has shown detrimental effects on antitumor activity of T cells, leading to T cell exhaustion[38]. The regulatable release of IL-12 via MSC should overcome the problems associated with systemic and constitutive delivery of IL-12. Utilizing the pCW57.1 Dox-inducible lentiviral vector (Addgene)[39], double promoter lentiviral vectors were created for Tet regulatable GFP-Fluc, p40 and p35 subunits of IL-12 and ScFV-PDL1 (FIG. 7A). The data indicate that mouse MSC expressing GFP-Fluc are tightly regulated using 9-tert-Butyl Doxycycline (9 TB-Dox) both in vitro and in vivo (FIG. 7B-C). Furthermore, the data indicate that MSC transduced with LV-TET-IL12 show a tightly regulated time dependent increase in IL-12 expression post 9 TB-Dox treatment (FIG. 7D).

Figure 8A:
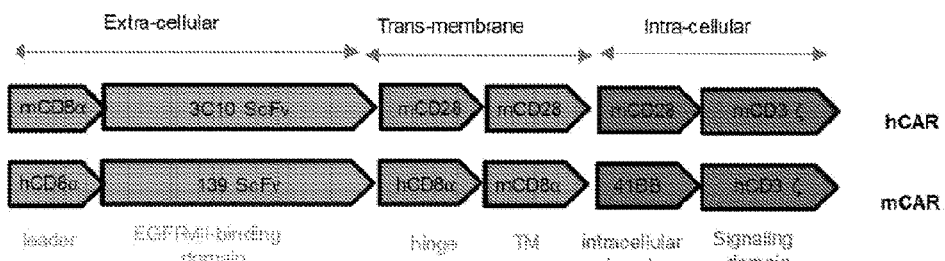
FIG. 8A-F shows EGFRvIII CAR engineered T cells have anti-tumor effects in culture.
Figure 8B:
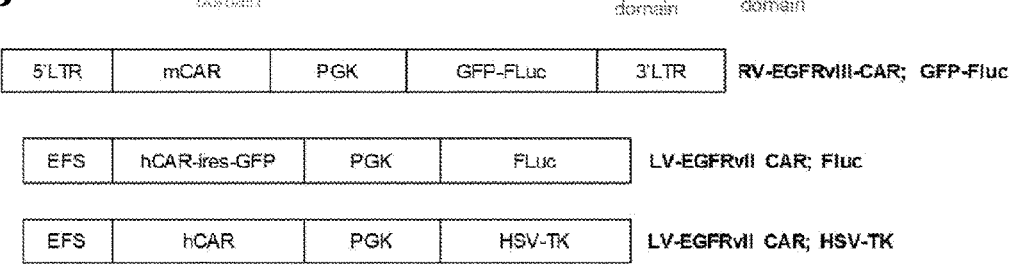
Figure 8C:
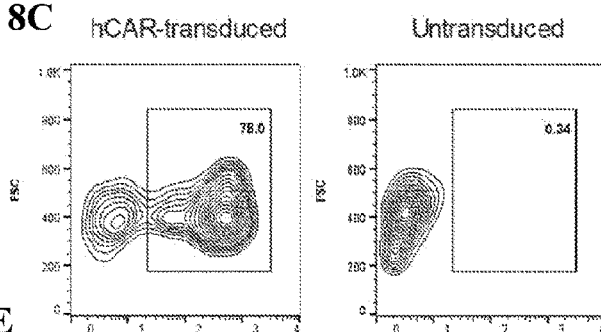
Figure 8D:
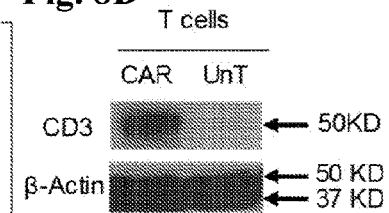
Figure 8E:
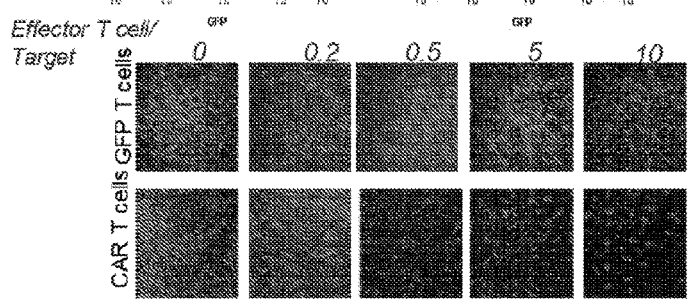
Figure 8F:
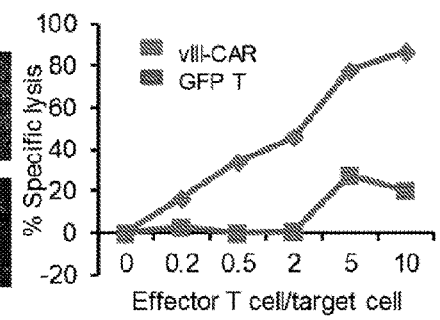

Previous studies have shown loss of functionality of CART cells post-tumor recruitment due to the up-regulation of inhibitory circuits[40]. Recent studies have indicated that PD-L1 upregulation in the tumor microenvironment results in PD-1 mediated inhibition of T cell function[41]. While not wishing to be bound by theory, it was hypothesized that if CAR T cells become exhausted in solid tumors[40], immune-checkpoint blockade can improve the potency of CAR T cell therapies[21,22] against such tumors. The combined efficacy of engineered MSCs expressing scFV-PDL1 and CAR T therapy in syngeneic GBM models of resection were tested. Mouse- and human-specific EGFRvIII CARs were created and engineered with dual promoter lentiviral and retroviral vectors respectively bearing GFP-Fluc and EGFRvIII specific ScFv for generation of human and mouse CAR T cells (FIG. 8A-B). The data show that T cells can be activated and transduced efficiently with LVs (FIG. 8C-E), with their functionality shown in vitro (FIG. 8F). These findings lend validity to the use of MSC in recruiting CAR T cells to solid tumors and further strengthen the rationale for the locally delivered MSC and systemically delivered CAR T in resected solid tumors.

Example 3: Intravenously Injected CAR-T Cells are not Effective Against Brain Tumors CAR T cells were intravenously injected into mice bearing brain tumors (FIG. 9).

Figure 9A:
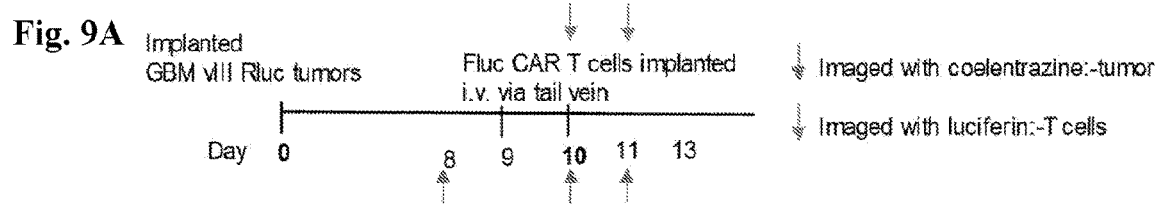
FIG. 9A-B shows EGFRvIII CAR engineered T cells injected intravenously have no efficacy in mice bearing brain tumors.
Figure 9B:
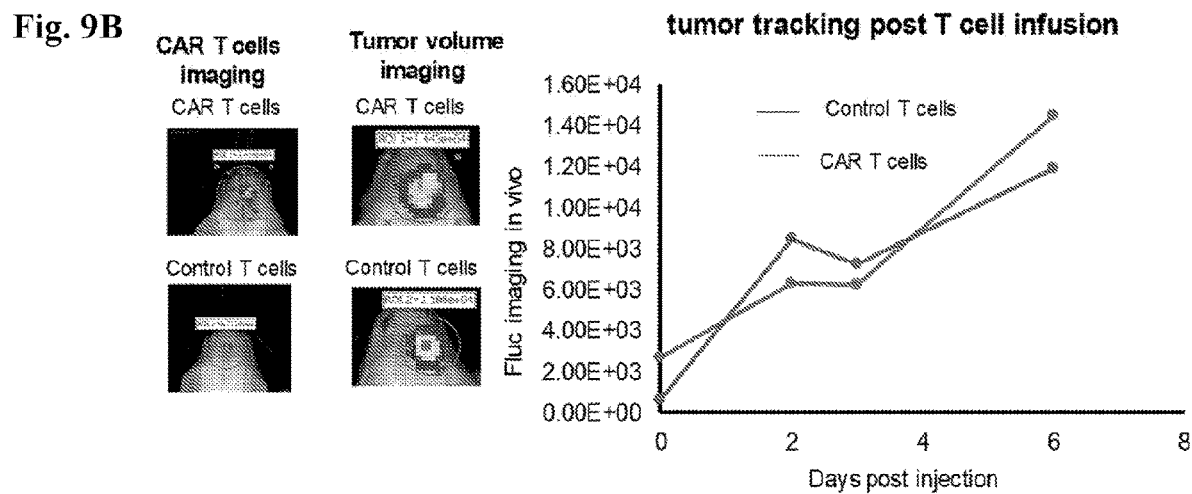

CAR T cells were delivered on day 10 post-tumor implantation (FIG. 9A). Fluc imaging of intravenously-administered CAR T cells show that there is not a significant difference between CAR T cells and control T cells delivered intravenously (FIG. 9B).

Example 4: Intratumorally Implanted CAR-T Cells have Therapeutic Efficacy

Figure 10A:
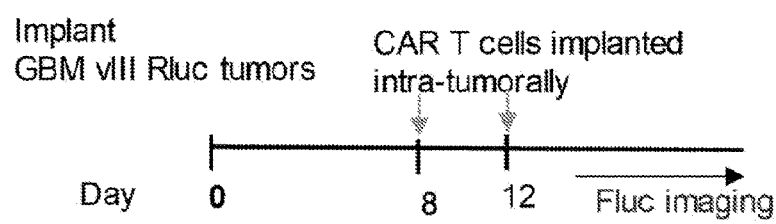
FIG. 10A depicts the experimental outline.
Figure 10B:
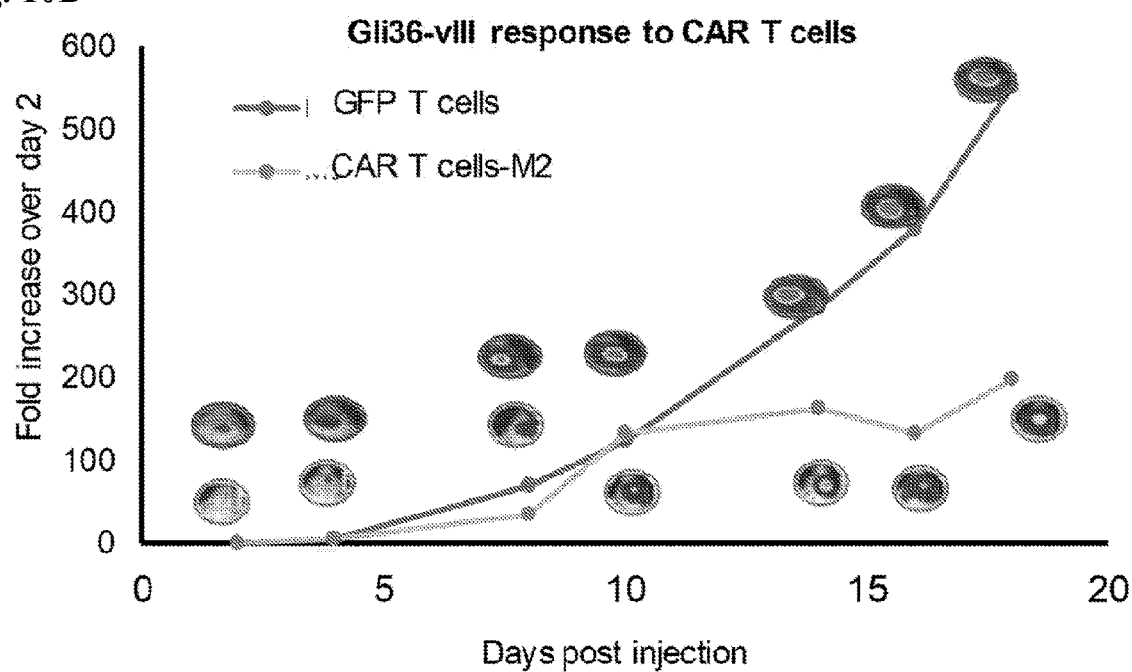

EGFRγII CAR T cells were implanted intratumorally on days 8 and 12 post tumor implantation (FIG. 10A). As a control, T cells were also implanted into control animals. Fluc imaging revealed that CAR T cells delivered intratumorally had dramatic therapeutic efficacy in mice with brain tumors (FIG. 10B).

Example 5: The Combination of CAR T Cells and IL-12-Producing MSCs Encapsulated in the sECM and Implanted in the GBM Tumor Resection Cavity have Therapeutic Efficacy While resection of the primary GBM tumor mass has shown clinical benefit, adjuvant chemotherapy post-tumor resection has provided limited additional benefit[42-45]. One of the major impediments to the efficient delivery of systemically delivered therapeutic agents is the blood brain barrier (BBB)[46] and vascular dysfunction in the tumor[47]. Additionally, many of the currently used drugs have a short systemic half-life and peak concentrations which prevent drugs from ultimately reaching the brain and accumulating to therapeutic concentrations within individual brain tumor cells[48]. These factors necessitate exploration of local delivery options of therapeutics to the tumors in the brain. It has been shown that stem cells exhibit potent pathotropic migratory properties, rendering them attractive for use as targeted delivery vectors in tumor therapy[43,49-53]. In particular, MSC are attractive for manipulation as they (i) exhibit high metabolic activity and thus strong expression of transgenes in vitro and in vivo; (ii) survive and integrate in the brain after transplantation; and (iii) have significantly low immunogenicity in the brain[54,55]. It has been shown that both mouse and human MSC engineered to express dual imaging marker, GFP-Fluc survive in the brains of immune-competent C57BL/6 and immune-compromised SCID mice up to at least 2 weeks[56,57].

These attributes render MSCs well-suited for targeted therapeutic delivery vehicles and strengthen the rationale for their use in GBM therapy. Although, direct intratumoral injection of therapeutic stem cells in intracranial tumors is effective, there are a number of limitations to test stem cell-based therapeutic interventions in mouse model of GBM resection that mimics the clinical scenario of tumor resection and treatment post-resection. These include developing methods to introduce stem cells into the resection cavity to prevent rapid "wash-out" of a significant number of cells by cerebrospinal fluid (CSF).

Figure 11A:
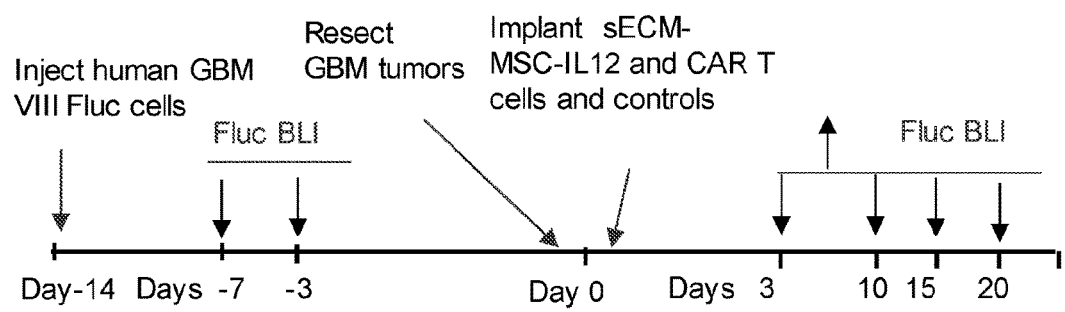
FIG. 11A-B shows sECM encapsulated EGFRvIII CAR engineered T cells and MSC releasing IL-12 placed in the tumor resection cavity have therapeutic benefits in mice bearing brain tumors.
Figure 11B:
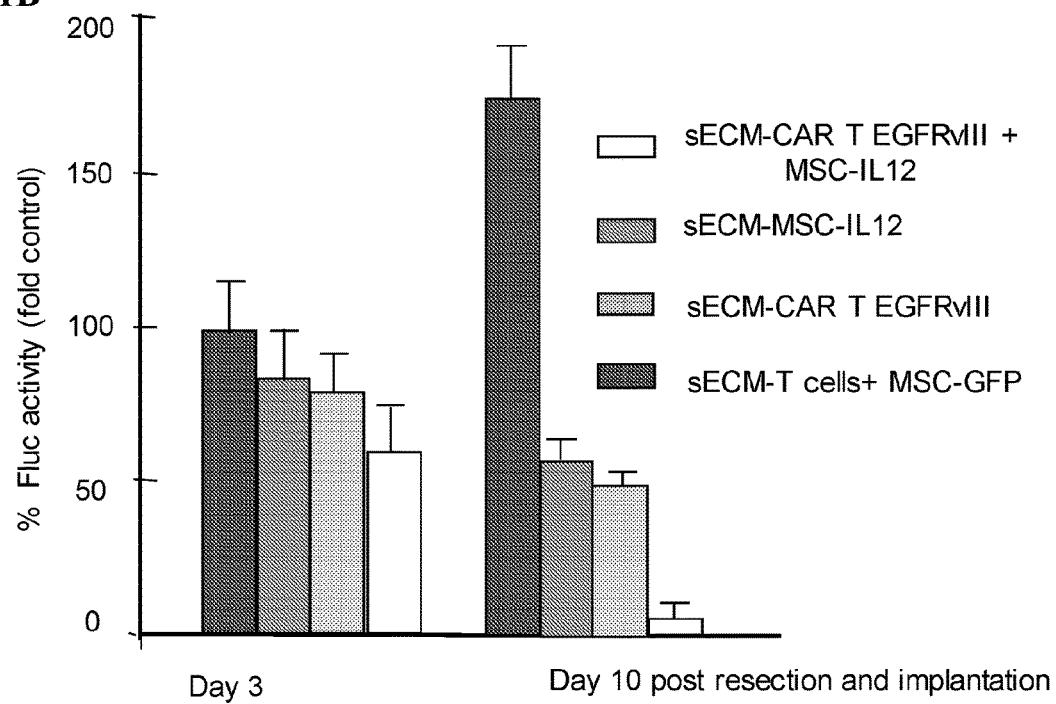

Previous reports have described the efficacy of second generation[58] and IL-12 secreting armored CAR T cells[59]. IL-12 was shown to significantly augment CAR T-cell efficacy in vitro and led to eradication of disseminated disease in a portion of treated mice[59]. Recently IL-12 armored CAR T cells were shown to overcome the inhibitory ascitic microenvironment, alter the ascitic cytokine and TAM microenvironment, and overcome PD-L1-mediated inhibition[60]. Due to their ability to provide a physiologic environment that promotes T cell and stem cell survival while permitting easy in vivo transplantation and cell retention, biodegradable sECM have been utilized in a variety of rodent models. It has been shown that sECM encapsulated stem cells expressing imageable GFP-Fluc when implanted in the GBM tumor resection cavity survive longer than non-encapsulated stem cells[61]. These data lend strong validity to the use of CART cells and MSC-IL-12 to target cells in the tumor microenvironment post-tumor resection. The present data indicate that the resection-induced immune reaction can be further modulated towards a tumor-specific immune response via local delivery of sECM-encapsulated EGFRvIII CAR T and MSCs expressing IL-12, resulting in the suppression of growth of residual tumors (FIG. 11A-B). Therefore, modulating non-specific immune reaction post-tumor debulking towards a tumor-specific immune response provides an ideal immunotherapy strategy in GBM treatment, where complete resection is not generally possible, and where the blood brain barrier can hamper tumor localization by MSCs or CAR-Ts administered systemically. Where it is demonstrated herein to be effective against the highly treatment-refractory GBM, this approach is specifically contemplated for use following the resection of any solid tumor.

REFERENCES

1. Valparaiso, A. P., Vicente, D. A., Bograd, B. A., Elster, E. A. & Davis, T. A. Modeling acute traumatic injury. The Journal of surgical research 194, 220-232 (2015).
2. Platanias, L. C. Mechanisms of type-I- and type-II-interferon-mediated signalling. Nature reviews. Immunology 5, 375-386 (2005).
3. Pokrovskaja, K., Panaretakis, T. & Grander, D. Alternative signaling pathways regulating type I interferon-induced apoptosis. J Interferon Cytokine Res 25, 799-810 (2005).
4. Dong, Z., et al. Suppression of angiogenesis, tumorigenicity, and metastasis by human prostate cancer cells engineered to produce interferon-beta. Cancer Res 59, 872-879 (1999).
5. Qin, X. Q., et al. Interferon-beta gene therapy inhibits tumor formation and causes regression of established tumors in immune-deficient mice. Proc Natl Acad Sci USA 95, 14411-14416 (1998).
6. Lykhova, A. A., et al. Suppression of proliferation, tumorigenicity and metastasis of lung cancer cells after their transduction by interferon-beta gene in baculovirus vector. Cytokine 71, 318-326 (2014).
7. Fuertes, M. B., et al. Host type I IFN signals are required for antitumor CD8+ T cell responses through CD8{alpha}+ dendritic cells. J Exp Med 208, 2005-2016 (2011).
8. Jablonska, J., Leschner, S., Westphal, K., Lienenklaus, S. & Weiss, S. Neutrophils responsive to endogenous IFN-beta regulate tumor angiogenesis and growth in a mouse tumor model. The Journal of clinical investigation 120, 1151-1164 (2010).
9. Tough, D. F., Borrow, P. & Sprent, J. Induction of bystander T cell proliferation by viruses and type I interferon in vivo. Science 272, 1947-1950 (1996).
10. Fierlbeck, G., et al. Pharmacodynamics of recombinant IFN-beta during long-term treatment of malignant melanoma. J Interferon Cytokine Res 16, 777-781 (1996).
11. Salmon, P., Le Cotonnec, J. Y., Galazka, A., Abdul-Ahad, A. & Darragh, A. Pharmacokinetics and pharmacodynamics of recombinant human interferon-beta in healthy male volunteers. J Interferon Cytokine Res 16, 759-764 (1996).
12. Trinchieri, G. Type I interferon: friend or foe? J Exp Med 207, 2053-2063 (2010).
13. Choi, S. H., et al. Tumor resection boosts therapeutic efficacy of encapsulated stem cells expressing a highly secretable variant of interferon-beta in glioblastomas. Clin Cancer Res (2017).
14. Stuckey, D. W., Hingtgen, S. D., Karakas, N., Rich, B. E. & Shah, K. Engineering toxin-resistant therapeutic stem cells to treat brain tumors. Stem Cells (2014).
15. Gibney, G. T., Weiner, L. M. & Atkins, M. B. Predictive biomarkers for checkpoint inhibitor-based immunotherapy. Lancet Oncol 17, e542-e551 (2016).
16. Zou, W., Wolchok, J. D. & Chen, L. PD-L1 (B7-H1) and PD-1 pathway blockade for cancer therapy: Mechanisms, response biomarkers, and combinations. Science translational medicine 8, 328rv324 (2016).
17. Garcia-Diaz, A., et al. Interferon Receptor Signaling Pathways Regulating PD-L1 and PD-L2 Expression. Cell reports 19, 1189-1201 (2017).
18. Parsa, A. T., et al. Loss of tumor suppressor PTEN function increases B7-H1 expression and immunoresistance in glioma. Nature medicine 13, 84-88 (2007).
19. Song, M., et al. PTEN loss increases PD-L1 protein expression and affects the correlation between PD-L1 expression and clinical parameters in colorectal cancer. PloS one 8, e65821 (2013).
20. Peng, W., et al. Loss of PTEN Promotes Resistance to T Cell-Mediated Immunotherapy. Cancer discovery 6, 202-216 (2016).
21. Reardon, D. A., et al. Glioblastoma Eradication Following Immune Checkpoint Blockade in an Orthotopic, Immunocompetent Model. Cancer Immunol Res 4, 124-135 (2016).
22. Sharma, P. & Allison, J. P. The future of immune checkpoint therapy. Science 348, 56-61 (2015).
23. Champiat, S., et al. Management of immune checkpoint blockade dysimmune toxicities: a collaborative position paper. Ann Oncol 27, 559-574 (2016).
24. Naidoo, J., et al. Toxicities of the anti-PD-1 and anti-PD-L1 immune checkpoint antibodies. Ann Oncol 27, 1362 (2016).

25. Scarfo, I. & Maus, M. V. Current approaches to increase CAR T cell potency in solid tumors: targeting the tumor microenvironment. J Immunother Cancer 5, 28 (2017).
26. Priceman, S. J., Forman, S. J. & Brown, C. E. Smart CARs engineered for cancer immunotherapy. Curr Opin Oncol 27, 466-474 (2015).
27. Wong, A. J., et al. Increased expression of the epidermal growth factor receptor gene in malignant gliomas is invariably associated with gene amplification. Proc Natl Acad Sci USA 84, 6899-6903 (1987).
28. Johnson, L. A., et al. Rational development and characterization of humanized anti-EGFR variant III chimeric antigen receptor T cells for glioblastoma. Science translational medicine 7, 275ra222 (2015).
29. Brown, C. E., et al. Tumor-derived chemokine MCP-1/CCL2 is sufficient for mediating tumor tropism of adoptively transferred T cells. J Immunol 179, 3332-3341 (2007).
30. Lanca, T., et al. Protective role of the inflammatory CCR2/CCL2 chemokine pathway through recruitment of type 1 cytotoxic gammadelta T lymphocytes to tumor beds. J Immunol 190, 6673-6680 (2013).
31. Lanca, T. & Silva-Santos, B. Recruitment of gammadelta T lymphocytes to tumors: A new role for the pleiotropic chemokine CCL2. Oncoimmunology 2, e25461 (2013).
32. Lee, H. K., et al. CCL2 deficient mesenchymal stem cells fail to establish long-lasting contact with T cells and no longer ameliorate lupus symptoms. Scientific reports 7, 41258 (2017).
33. Lasek, W., Zagozdzon, R. & Jakobisiak, M. Interleukin 12: still a promising candidate for tumor immunotherapy? Cancer immunology, immunotherapy: CII 63, 419-435 (2014).
34. Alkayyal, A. A., et al. NK-Cell Recruitment Is Necessary for Eradication of Peritoneal Carcinomatosis with an IL12-Expressing Maraba Virus Cellular Vaccine. Cancer Immunol Res 5, 211-221 (2017).
35. Del Vecchio, M., et al. Interleukin-12: biological properties and clinical application. Clin Cancer Res 13, 4677-4685 (2007).
36. Gubler, U., et al. Coexpression of two distinct genes is required to generate secreted bioactive cytotoxic lymphocyte maturation factor. Proc Natl Acad Sci USA 88, 4143-4147 (1991).
37. van de Water, J. A., et al. Therapeutic stem cells expressing variants of EGFR-specific nanobodies have antitumor effects. Proc Natl Acad Sci USA 109, 16642-16647 (2012).
38. Yang, Z. Z., et al. IL-12 upregulates TIM-3 expression and induces T cell exhaustion in patients with follicular B cell non-Hodgkin lymphoma. The Journal of clinical investigation 122, 1271-1282 (2012).
39. Wang, T., Wei, J. J., Sabatini, D. M. & Lander, E. S. Genetic screens in human cells using the CRISPR-Cas9 system. Science 343, 80-84 (2014).
40. Moon, E. K., et al. Multifactorial T-cell hypofunction that is reversible can limit the efficacy of chimeric antigen receptor-transduced human T cells in solid tumors. Clin Cancer Res 20, 4262-4273 (2014).
41. Cherkassky, L., et al. Human CART cells with cell-intrinsic PD-1 checkpoint blockade resist tumor-mediated inhibition. The Journal of clinical investigation 126, 3130-3144 (2016).
42. Minniti, G., et al. Radiotherapy plus concomitant and adjuvant temozolomide for glioblastoma in elderly patients. J Neurooncol 88, 97-103 (2008).
43. Shah, K. Stem cell-based therapies for tumors in the brain: are we there yet? Neuro Oncol 18, 1066-1078 (2016).
44. Wen, P. Y., et al. Phase I/II study of erlotinib and temsirolimus for patients with recurrent malignant gliomas: North American Brain Tumor Consortium trial 04-02. Neuro Oncol 16, 567-578 (2014).
45. Wen, P. Y. & Kesari, S. Malignant gliomas in adults. N Engl J Med 359, 492-507 (2008).
46. Muldoon, L. L., et al. Chemotherapy delivery issues in central nervous system malignancy: a reality check. J Clin Oncol 25, 2295-2305 (2007).
47. Jain, R. K., et al. Angiogenesis in brain tumours. Nat Rev Neurosci 8, 610-622 (2007).
48. Sarin, H. Recent progress towards development of effective systemic chemotherapy for the treatment of malignant brain tumors. J Transl Med 7, 77 (2009).
49. Aboody, K. S., et al. Neural stem cell-mediated enzyme/prodrug therapy for glioma: preclinical studies. Science translational medicine 5, 184ra159 (2013).
50. Ehtesham, M., et al. The use of interleukin 12-secreting neural stem cells for the treatment of intracranial glioma. Cancer Res 62, 5657-5663 (2002).
51. Lee, J., et al. Cellular and genetic characterization of human adult bone marrow-derived neural stem-like cells: a potential antiglioma cellular vector. Cancer Res 63, 8877-8889 (2003).
52. Nakamizo, A., et al. Human bone marrow-derived mesenchymal stem cells in the treatment of gliomas. Cancer Res 65, 3307-3318 (2005).
53. Stuckey, D. W. & Shah, K. Stem cell-based therapies for cancer treatment: separating hope from hype. Nat Rev Cancer 14, 683-691 (2014).
54. Aboody, K. S., et al. Neural stem cells display extensive tropism for pathology in adult brain: evidence from intracranial gliomas. Proc Natl Acad Sci USA 97, 12846-12851 (2000).
55. Corsten, M. F. & Shah, K. Therapeutic stem-cells for cancer treatment: hopes and hurdles in tactical warfare. Lancet Oncol 9, 376-384 (2008).
56. Martinez-Quintanilla, J., et al. Therapeutic efficacy and fate of bimodal engineered stem cells in malignant brain tumors. Stem Cells 31, 1706-1714 (2013).
57. Sasportas, L. S., et al. Assessment of therapeutic efficacy and fate of engineered human mesenchymal stem cells for cancer therapy. Proc Natl Acad Sci USA 106, 4822-4827 (2009).
58. Chekmasova, A. A., et al. Successful eradication of established peritoneal ovarian tumors in SCID-Beige mice following adoptive transfer of T cells genetically targeted to the MUC16 antigen. Clin Cancer Res 16, 3594-3606 (2010).
59. Koneru, M., Purdon, T. J., Spriggs, D., Koneru, S. & Brentjens, R. J. IL-12 secreting tumor-targeted chimeric antigen receptor T cells eradicate ovarian tumors in vivo. Oncoimmunology 4, e994446 (2015).
60. Yeku, O. O., Purdon, T. J., Koneru, M., Spriggs, D. & Brentjens, R. J. Armored CAR T cells enhance antitumor efficacy and overcome the tumor microenvironment. Scientific reports 7, 10541 (2017).
61. Kauer, T. M., Figueiredo, J. L., Hingtgen, S. & Shah, K. Encapsulated therapeutic stem cells implanted in the tumor resection cavity induce cell death in gliomas. Nat Neurosci (2012).

SEQUENCES
(PD-L1-*Homo sapiens*-Isoform a)

SEQ ID NO: 1

```
  1 MRIFAVFIFM TYWHLLNAFT VTVPKDLYVV EYGSNMTIEC KFPVEKQLDL AALIVYWEME

61 DKNIIQFVHG EEDLKVQHSS YRQRARLLKD QLSLGNAALQ ITDVKLQDAG VYRCMISYGG

121 ADYKRITVKV NAPYNKINQR ILVVDPVTSE HELTCQAEGY PKAEVIWTSS DHQVLSGKTT

181 TTNSKREEKL FNVTSTLRIN TTTNEIFYCT FRRLDPEENH TAELVIPELP LAHPPNERTH

241 LVILGAILLC LGVALTFIFR LRKGRMMDVK KCGIQDTNSK KQSDTHLEET
```

(PD-1-*Homo sapiens*)

SEQ ID NO: 2

```
  1 MQIPQAPWPV VWAVLQLGWR PGWFLDSPDR PWNPPTFSPA LLVVTEGDNA TFTCSFSNTS

61 ESFVLNWYRM SPSNQTDKLA AFPEDRSQPG QDCRFRVTQL PNGRDFHMSV VRARRNDSGT

121 YLCGAISLAP KAQIKESLRA ELRVTERRAE VPTAHPSPSP RPAGQFQTLV VGVVGGLLGS

181 LVLLVWVLAV ICSRAARGTI GARRTGQPLK EDPSAVPVFS VDYGELDFQW REKTPEPPVP

241 CVPEQTEYAT IVFPSGMGTS SPARRGSADG PRSAQPLRPE DGHCSWPL
```

(CTLA-4-*Homo sapiens*)

SEQ ID NO: 3

```
  1 MACLGFQRHK AQLNLATRTW PCTLLFFLLF IPVFCKAMHV AQPAVVLASS RGIASFVCEY

61 ASPGKATEVR VTVLRQADSQ VTEVCAATYM MGNELTFLDD SICTGTSSGN QVNLTIQGLR

121 AMDTGLYICK VELMYPPPYY LGIGNGTQIY VIDPEPCPDS DFLLWILAAV SSGLFFYSFL

181 LTAVSLSKML KKRSPLTTGV YVKMPPTEPE CEKQFQPYFI PIN
```

(TIM-3-*Homo sapiens*)

SEQ ID NO: 4

```
  1 MSKEPLILWL MIEFWWLYLT PVTSETVVTE VLGHRVTLPC LYSSWSHNSN SMCWGKDQCP

61 YSGCKEALIR TDGMRVTSRK SAKYRLQGTI PRGDVSLTIL NPSESDSGVY CCRIEVPGWF

121 NDVKINVRLN LQRASTTTHR TATTTTRRTT TTSPTTTRQM TTTPAALPTT VVTTPDLTTG

181 TPLQMTTIAV FTTANTCLSL TPSTLPEEAT GLLTPEPSKE GPILTAESET VLPSDSWSSV

241 ESTSADTVLL TSKESKVWDL PSTSHVSMWK TSDSVSSPQP GASDTAVPEQ NKTTKTGQMD

301 GIPMSMKNEM PISQLLMIIA PSLGFVLFAL FVAFLLRGKL METYCSQKHT RLDYIGDSKN

361 VLNDVQHGRE DEDGLFTL
```

(LAG-3-*Homo sapiens*)

SEQ ID NO: 5

```
  1 MWEAQFLGLL FLQPLWVAPV KPLQPGAEVP VVWAQEGAPA QLPCSPTIPL QDLSLLRRAG

61 VTWQHQPDSG PPAAAPGHPL APGPHPAAPS SWGPRPRRYT VLSVGPGGLR SGRLPLQPRV

121 QLDERGRQRG DFSLWLRPAR RADAGEYRAA VHLRDRALSC RLRLRLGQAS MTASPPGSLR

181 ASDWVILNCS FSRPDRPASV HWFRNRGQGR VPVRESPHHH LAESFLFLPQ VSPMDSGPWG

241 CILTYRDGFN VSIMYNLTVL GLEPPTPLTV YAGAGSRVGL PCRLPAGVGT RSFLTAKWTP

301 PGGGPDLLVT GDNGDFTLRL EDVSQAQAGT YTCHIHLQEQ QLNATVTLAI ITVTPKSFGS

361 PGSLGKLLCE VTPVSGQERF VWSSLDTPSQ RSFSGPWLEA QEAQLLSQPW QCQLYQGERL

421 LGAAVYFTEL SSPGAQRSGR APGALPAGHL LLFLILGVLS LLLLVTGAFG FHLWRRQWRP

481 RRFSALEQGI HPPQAQSKIE ELEQEPEPEP EPEPEPEPEP EPEQL
```

SEQ ID NO: 6

(TIGIT-*Homo sapiens*)

```
  1 MRWCLLLIWA QGLRQAPLAS GMMTGTIETT GNISAEKGGS IILQCHLSST TAQVTQVNWE

61 QQDQLLAICN ADLGWHISPS FKDRVAPGPG LGLTLQSLTV NDTGEYFCIY HTYPDGTYTG

121 RIFLEVLESS VAEHGARFQI PLLGAMAATL VVICTAVIVV VALTRKKKAL RIHSVEGDLR

181 RKSAGQEEWS PSAPSPPGSC VQAEAAPAGL CGEQRGEDCA ELHDYFNVLS YRSLGNCSFF
```

```
241 TETG
```

(TIGIT-*Mus musculus*)
SEQ ID NO: 7
```
  1 MHGWLLLVWV QGLIQAAFLA TGATAGTIDT KRNISAEEGG SVILQCHFSS DTAEVTQVDW
 61 KQQDQLLAIY SVDLGWHVAS VFSDRVVPGP SLGLTFQSLT MNDTGEYFCT YHTYPGGIYK
121 GRIFLKVQES SVAQFQTAPL GGTMAAVLGL ICLMVTGVTV LARKKSIRMH SIESGLGRTE
181 AEPQEWNLRS LSSPGSPVQT QTAPAGPCGE QAEDDYADPQ EYFNVLSYRS LESFIAVSKT
241 G
```

(CTLA-4 *Mus musculus*)
SEQ ID NO: 8
```
  1 MACLGLRRYK AQLQLPSRTW PFVALLTLLF IPVFSEAIQV TQPSVVLASS HGVASFPCEY
 61 SPSHNTDEVR VTVLRQTNDQ MTEVCATTFT EKNTVGFLDY PFCSGTFNES RVNLTIQGLR
121 AVDTGLYLCK VELMYPPPYF VGMGNGTQIY VIDPEPCPDS DFLLWILAAV SLGLFFYSFL
181 VTAVSLSKML KKRSPLTTGV YVKMPPTEPE CEKQFQPYFI PIN
```

(TIM-3-*Homo sapiens*)
SEQ ID NO: 9
```
  1 MFSHLPFDCV LLLLLLLLTR SSEVEYRAEV GQNAYLPCFY TPAAPGNLVP VCWGKGACPV
 61 FECGNVVLRT DERDVNYWTS RYWLNGDFRK GDVSLTIENV TLADSGIYCC RIQIPGIMND
121 EKFNLKLVIK PAKVTPAPTR QRDFTAAFPR MLTTRGHGPA ETQTLGSLPD INLTQISTLA
181 NELRDSRLAN DLRDSGATIR IGIYIGAGIC AGLALALIFG ALIFKWYSHS KEKIQNLSLI
241 SLANLPPSGL ANAVAEGIRS EENIYTIEEN VYEVEEPNEY YCYVSSRQQP SQPLGCRFAM
301 P
```

(TIM-3-*Mus musculus*)
SEQ ID NO: 10
```
  1 MFSGLTLNCV LLLLQLLLAR SLENAYVFEV GKNAYLPCSY TLSTPGALVP MCWGKGFCPW
 61 SQCTNELLRT DERNVTYQKS SRYQLKGDLN KGDVSLIIKN VTLDDHGTYC CRIQFPGLMN
121 DKKLELKLDI KAAKVTPAQT AHGDSTTASP RTLTTERNGS ETQTLVTLHN NNGTKISTWA
181 DEIKDSGETI RTAIHIGVGV SAGLTLALII GVLILKWYSC KKKKLSSLSL ITLANLPPGG
241 LANAGAVRIR SEENIYTIEE NVYEVENSNE YYCYVNSQQP S
```

(LAG-3-*Mus musculus*)
SEQ ID NO: 11
```
  1 MREDLLLGFL LLGLLWEAPV VSSGPGKELP VVWAQEGAPV HLPCSLKSPN LDPNFLRRGG
 61 VIWQHQPDSG QPTPIPALDL HQGMPSPRQP APGRYTVLSV APGGLRSGRQ PLHPHVQLEE
121 RGLQRGDFSL WLRPALRTDA GEYHATVRLP NRALSCSLRL RVGQASMIAS PSGVLKLSDW
181 VLLNCSFSRP DRPVSVHWFQ GQNRVPVYNS PRHFLAETFL LPQVSPLDS GTWGCVLTYR
241 DGFNVSITYN LKVLGLEPVA PLTVYAAEGS RVELPCHLPP GVGTPSLLIA KWTPPGGGPE
301 LPVAGKSGNF TLHLEAVGLA QAGTYTCSIH LQGQQLNATV TLAVITVTPK SFGLPGSRGK
361 LLCEVTPASG KERFVWRPLN NLSRSCPGPV LEIQEARLLA ERWQCQLYEG QRLLGATVYA
421 AESSSGAHSA RRISGDLKGG HLVLVLILGA LSLFLLVAGA FGFHWWRKQL LLRRFSALEH
481 GIQPFPAQRK IEELERELET EMGQEPEPEP EPQLEPEPRQ L
```

(PD-L1-*Homo sapiens*-isoform b)
SEQ ID NO: 12
```
  1 MRIFAVFIFM TYWHLLNAPY NKINQRILVV DPVTSEHELT CQAEGYPKAE VIWTSSDHQV
 61 LSGKTTTTNS KREEKLFNVT STLRINTTTN EIFYCTFRRL DPEENHTAEL VIPELPLAHP
121 PNERTHLVIL GAILLCLGVA LTFIFRLRKG RMMDVKKCGI QDTNSKKQSD THLEET
```

(PD-L-1-*Homo sapiens*-isoform c)
SEQ ID NO: 13
```
  1 MRIFAVFIFM TYWHLLNAFT VTVPKDLYVV EYGSNMTIEC KFPVEKQLDL AALIVYWEME
```

-continued

```
 61 DKNIIQFVHG EEDLKVQHSS YRQRARLLKD QLSLGNAALQ ITDVKLQDAG VYRCMISYGG
121 ADYKRITVKV NAPYNKINQR ILVVDPVTSE HELTCQAEGY PKAEVIWTSS DHQVLSGKTT
181 TTNSKREEKL FNVTSTLRIN TTTNEIFYCT FRRLDPEENH TAELVIPGNI LNVSIKICLT
241 LSPST
```

(PD-L-1-*Mus musculus*)

SEQ ID NO: 14

```
  1 MRIFAGIIFT ACCHLLRAFT ITAPKDLYVV EYGSNVTMEC RFPVERELDL LALVVYWEKE
 61 DEQVIQFVAG EEDLKPQHSN FRGRASLPKD QLLKGNAALQ ITDVKLQDAG VYCCIISYGG
121 ADYKRITLKV NAPYRKINQR ISVDPATSEH ELICQAEGYP EAEVIWTNSD HQPVSGKRSV
181 TTSRTEGMLL NVTSSLRVNA TANDVFYCTF WRSQPGQNHT AELIIPELPA THPPQNRTHW
241 VLLGSILLFL IVVSTVLLFL RKQVRMLDVE KCGVEDTSSK NRNDTQFEET
```

(PD-1-*Mus musculus*)

SEQ ID NO: 15

```
  1 MWVRQVPWSF TWAVLQLSWQ SGWLLEVPNG PWRSLTFYPA WLTVSEGANA TFTCSLSNWS
 61 EDLMLNWNRL SPSNQTEKQA AFCNGLSQPV QDARFQIIQL PNRHDFHMNI LDTRRNDSGI
121 YLCGAISLHP KAKIEESPGA ELVVTERILE TSTRYPSPSP KPEGRFQGMV IGIMSALVGI
181 PVLLLLAWAL AVFCSTSMSE ARGAGSKDDT LKEEPSAAPV PSVAYEELDF QGREKTPELP
241 TACVHTEYAT IVFTEGLGAS AMGRRGSADG LQGPRPPRHE DGHCSWPL
```

(Ipilimumab heavy chain-US20150283234)

SEQ ID NO: 16

QVQLVESGGGVVQPGRSLRLSCAASGFTFSSYTMHWVRQAPGKGLEWVTFISYDGNNKYY
ADSVKGRFTISRDNSKNTLYLQMNSLRAEDTAIYYCARTGWLGPFDYWGQGTLVTVSSAS
TKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKRVEPKSCDKTHTCPPCPAPELLGGPS
VFLFPPKPKDTLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVYTLPPSRDELT
KNQVSLTCLVKGFYPSDIAVEWESNGQPENNYKTTPPVLDSDGSFFLYSKLTVDKSRWQQ
GNVFSCSVMHEALHNHYTQKSLSLSPGK (Ipilimumab light chain-US20150283234)

SEQ ID NO: 17

EIVLTQSPGTLSLSPGERATLSCRASQSVGSSYLAWYQQKPGQAPRLLIYGAFSRATGIP
DRFSGSGSGTDFTLTISRLEPEDFAVYYCQQYGSSPWTFGQGTKVEIKRTVAAPSVFIFP
PSDEQLKSGTASVVCLLNNFYPREAKVQWKVDNALQSGNSQESVTEQDSKDSTYSLSSTL
TLSKADYEKHKVYACEVTHQGLSSPVTKSFNRGEC (Pembrolizumab heavy chain sequence-US2012135408)

SEQ ID NO: 18

QVQLVQSGVEVKKPGASVKVSCKASGYTFTNYYMYWVRQAPGQGLEWMGGINPSNGGTNF
NEKFKNRVTLTTDSSTTTAYMELKSLQFDDTAVYYCARRDYRFDMGFDYWGQGTTVTVSS
ASTKGPSVFPLAPCSRSTSESTAALGCLVKDYFPEPVTVSWNSGALTSGVHTFPAVLQSS
GLYSLSSVVTVPSSSLGTKTYTCNVDHKPSNTKVDKRVESKYGPPCPPCPAPEFLGGPSV
FLFPPKPKDTLMISRTPEVTCVVVDVSQEDPEVQFNWYVDGVEVHNAKTKPREEQFNSTY
RVVSVLTVLHQDWLNGKEYKCKVSNKGLPSSIEKTISKAKGQPREPQVYTLPPSQEEMTK
NQVSLTCLVKGFYPSDIAVEWESNGQPENNYKTTPPVLDSDGSFFLYSRLTVDKSRWQEG
NVFSCSVMHEALHNHYTQKSLSLSLGK (Pembrolizumab light chain sequence-US2012135408)

SEQ ID NO: 19

-continued

EIVLTQSPATLSLSPGERATLSCRASKGVSTSGYSYLHWYQQKPGQAPRLLIYLASYLES

GVPARFSGSGSGTDFTLTISSLEPEDFAVYYCQHSRDLPLTFGGGTKVEIKRTVAAPSVF

IFPPSDEQLKSGTASVVCLLNNFYPREAKVQWKVDNALQSGNSQESVTEQDSKDSTYSLS

STLTLSKADYEKHKVYACEVTHQGLSSPVTKSFNRGEC (Nivolumab-heavy chain sequence-US2013173223) SEQ ID NO: 20

QVQLVESGGGVVQPGRSLRLDCKASGITFSNSGMHWVRQAPGKGLEWVAVIWYDGSKRYY

ADSVKGRFTISRDNSKNTLFLQMNSLRAEDTAVYYCATNDDYWGQGTLVTVSSASTKGPS

VFPLAPCSRSTSESTAALGCLVKDYFPEPVTVSWNSGALTSGVHTFPAVLQSSGLYSLSS

VVTVPSSSLGTKTYTCNVDHKPSNTKVDKRVESKYGPPCPPCPAPEFLGGPSVFLFPPKP

KDTLMISRTPEVTCVVVDVSQEDPEVQFNWYVDGVEVHNAKTKPREEQFNSTYRVVSVLT

VLHQDWLNGKEYKCKVSNKGLPSSIEKTISKAKGQPREPQVYTLPPSQEEMTKNQVSLTC

LVKGFYPSDIAVEWESNGQPENNYKTTPPVLDSDGSFFLYSRLTVDKSRWQEGNVFSCSV

MHEALHNHYTQKSLSLSLGK (Nivolumab-light chain sequence-US2013173223) SEQ ID NO: 21

EIVLTQSPATLSLSPGERATLSCRASQSVSSYLAWYQQKPGQAPRLLIYDASNRATGIPA

RFSGSGSGTDFTLTISSLEPEDFAVYYCQQSSNWPRTFGQGTKVEIKRTVAAPSVFIFPP

SDEQLKSGTASVVCLLNNFYPREAKVQWKVDNALQSGNSQESVTEQDSKDSTYSLSSTLT

LSKADYEKHKVYACEVTHQGLSSPVTKSFNRGEC (Atezolizumab-heavy chain sequence) SEQ ID NO: 22

EVQLVESGGGLVQPGGSLRLSCAASGFTFSDSWIHWVRQAPGKGLEWVAWISPYGGSTYY

ADSVKGRFTISADTSKNTAYLQMNSLRAEDTAVYYCARRHWPGGFDYWGQGTLVTVSSAS

TKGPSVFPLAPSSKSTSGGTAALGCLVKDYFPEPVTVSWNSGALTSGVHTFPAVLQSSGL

YSLSSVVTVPSSSLGTQTYICNVNHKPSNTKVDKKVEPKSCDKTHTCPPCPAPELLGGPS

VFLFPPKPKDTLMISRTPEVTCVVVDVSHEDPEVKFNWYVDGVEVHNAKTKPREEQYAST

YRVVSVLTVLHQDWLNGKEYKCKVSNKALPAPIEKTISKAKGQPREPQVYTLPPSREEMT

KNQVSLTCLVKGFYPSDIAVEWESNGQPENNYKTTPPVLDSDGSFFLYSKLTVDKSRWQQ

GNVFSCSVMHEALHNHYTQKSLSLSPGK (Atezolizumab-light chain sequence) SEQ ID NO: 23

DIQMTQSPSSLSASVGDRVTITCRASQDVSTAVAWYQQKPGKAPKLLIYSASFLYSGVPS

RFSGSGSGTDFTLTISSLQPEDFATYYCQQYLYHPATFGQGTKVEIKRTVAAPSVFIFPP

SDEQLKSGTASVVCLLNNFYPREAKVQWKVDNALQSGNSQESVTEQDSKDSTYSLSSTLT

LSKADYEKHKVYACEVTHQGLSSPVTKSFNRGEC (anti-TIM antibody heavy chain-WO2018129553A1) SEQ ID NO: 24

EVQLLESGGGLVQPGGSLRLSCAAASGFTFSSYDMSWVRQAPGKGLDWVSTISG

GGTYTYYQDSVKGRFTISRDNSKNTLYLQMNSLRAEDTAVYYCASMDYWGQG

TTVTVSSA (anti-TIM antibody light chain-WO2018129553A1) SEQ ID NO: 25

DIQMTQSPSSLSASVGDRVTITCRASQSIRRYLNWYHQKPGKAPKLLIYG ASTLQ

SGVPSRFSGSGSGTDFTLTISSLQPEDFAVYYCQQSHSAPLTFGGGTKVEIKR (EGFR vIII-Homo sapiens) SEQ ID NO: 26

1 MRPSGTAGAA LLALLAALCP ASRALEEKKV CQGTSNKLTQ LGTFEDHFLS LQRMFNNCEV

-continued

```
  61 VLGNLEITYV QRNYDLSFLK TIQEVAGYVL IALNTVERIP LENLQIIRGN MYYENSYALA
 121 VLSNYDANKT GLKELPMRNL QGQKCDPSCP NGSCWGAGEE NCQKLTKIIC AQQCSGRCRG
 181 KSPSDCCHNQ CAAGCTGPRE SDCLVCRKFR DEATCKDTCP PLMLYNPTTY QMDVNPEGKY
 241 SFGATCVKKC PRNYVVTDHG SCVRACGADS YEMEEDGVRK CKKCEGPCRK VCNGIGIGEF
 301 KDSLSINATN IKHFKNCTSI SGDLHILPVA FRGDSFTHTP PLDPQELDIL KTVKEITGFL
 361 LIQAWPENRT DLHAFENLEI IRGRTKQHGQ FSLAVVSLNI TSLGLRSLKE ISDGDVIISG
 421 NKNLCYANTI NWKKLFGTSG QKTKIISNRG ENSCKATGQV CHALCSPEGC WGPEPRDCVS
 481 CRNVSRGREC VDKCNLLEGE PREFVENSEC IQCHPECLPQ AMNITCTGRG PDNCIQCAHY
 541 IDGPHCVKTC PAGVMGENNT LVWKYADAGH VCHLCHPNCT YGCTGPGLEG CPTNGPKIPS
 601 IATGMVGALL LLLVVALGIG LFMRRRHIVR KRTLRRLLQE RELVEPLTPS GEAPNQALLR
 661 ILKETEFKKI KVLGSGAFGT VYKGLWIPEG EKVKIPVAIK ELREATSPKA NKEILDEAYV
 721 MASVDNPHVC RLLGICLTST VQLITQLMPF GCLLDYVREH KDNIGSQYLL NWCVQIAKGM
 781 NYLEDRRLVH RDLAARNVLV KTPQHVKITD FGLAKLLGAE EKEYHAEGGK VPIKWMALES
 841 ILHRIYTHQS DVWSYGVTVW ELMTFGSKPY DGIPASEISS ILEKGERLPQ PPICTIDVYM
 901 IMVKCWMIDA DSRPKFRELI IEFSKMARDP QRYLVIQGDE RMHLPSPTDS NFYRALMDEE
 961 DMDDVVDADE YLIPQQGFFS SPSTSRTPLL SSLSATSNNS TVACIDRNGL QSCPIKEDSF
1021 LQRYSSDPTG ALTEDSIDDT FLPVPGEWLV WKQSCSSTSS THSAAASLQC PSQVLPPASP
1081 EGETVADLQT Q
```

(EGFR vIII-*Mus musculus*)
SEQ ID NO: 27

```
   1 MRPSGTARTT LLVLLTALCA AGGALEEKKV CQGTSNRLTQ LGTFEDHFLS LQRMYNNCEV
  61 VLGNLEITYV QRNYDLSFLK TIQEVAGYVL IALNTVERIP LENLQIIRGN ALYENTYALA
 121 ILSNYGTNRT GLRELPMRNL QEILIGAVRF SNNPILCNMD TIQWRDIVQN VFMSNMSMDL
 181 QSHPSSCPKC DPSCPNGSCW GGGEENCQKL TKIICAQQCS HRCRGRSPSD CCHNQCAAGC
 241 TGPRESDCLV CQKFQDEATC KDTCPPLMLY NPTTYQMDVN PEGKYSFGAT CVKKCPRNYV
 301 VTDHGSCVRA CGPDYYEVEE DGIRKCKKCD GPCRKVCNGI GIGEFKDTLS INATNIKHFK
 361 YCTAISGDLH ILPVAFKGDS FTRTPPLDPR ELEILKTVKE ITGFLLIQAW PDNWTDLHAF
 421 ENLEIIRGRT KQHGQFSLAV VGLNITSLGL RSLKEISDGD VIISGNRNLC YANTINWKKL
 481 FGTPNQKTKI MNNRAEKDCK AVNHVCNPLC SSEGCWGPEP RDCVSCQNVS RGRECVEKCN
 541 ILEGEPREFV ENSECIQCHP ECLPQAMNIT CTGRGPDNCI QCAHYIDGPH CVKTCPAGIM
 601 GENNTLVWKY ADANNVCHLC HANCTYGCAG PGLQGCEVWP SGPKIPSIAT GIVGGLLFIV
 661 VVALGIGLFM RRRHIVRKRT LRRLQEREL VEPLTPSGEA PNQAHLRILK ETEFKKIKVL
 721 GSGAFGTVYK GLWIPEGEKV KIPVAIKELR EATSPKANKE ILDEAYVMAS VDNPHVCRLL
 781 GICLTSTVQL ITQLMPYGCL LDYVREHKDN IGSQYLLNWC VQIAKGMNYL EDRRLVHRDL
 841 AARNVLVKTP QHVKITDFGL AKLLGAEEKE YHAEGGKVPI KWMALESILH RIYTHQSDVW
 901 SYGVTVWELM TFGSKPYDGI PASDISSILE KGERLPQPPI CTIDVYMIMV KCWMIDADSR
 961 PKFRELILEF SKMARDPQRY LVIQGDERMH LPSPTDSNFY RALMDEEDME DVVDADEYLI
1021 PQQGFFNSPS TSRTPLLSSL SATSNNSTVA CINRNGSCRV KEDAFLQRYS SDPTGAVTED
1081 NIDDAFLPVP EYVNQSVPKR PAGSVQNPVY HNQPLHPAPG RDLHYQNPHS NAVGNPEYLN
1141 TAQPTCLSSG FNSPALWIQK GSHQMSLDNP DYQQDFFPKE TKPNGIFKGP TAENAEYLRV
1201 APPSSEFIGA
```

What is claimed is:

1. A method of treating glioblastoma multiforme (GBM) in a subject, the method comprising:
   a) resecting a glioblastoma multiforme (GBM) tumor from the subject, wherein the resecting creates a cavity formerly occupied by tumor tissue;
   b) administering a genetically modified T cell expressing on its cell surface a chimeric T cell antigen receptor comprising a heterologous binding domain that specifically binds to EGFRvIII expressed on the surface of cells of the cancer, and an intracellular signaling domain, wherein binding of the heterologous binding domain to the tumor antigen on the surface of a cancer cell activates the intracellular signaling domain and the T cell, and wherein the genetically modified T cell is encapsulated in a matrix placed in the resection cavity; and
   c) administering a first genetically modified mesenchymal stem cell, that expresses an Interleukin-12 (IL-12) polypeptide, wherein the genetically modified mesenchymal stem cell is encapsulated in a matrix placed in the resection cavity,
   wherein the heterologous immunomodulatory polypeptide potentiates GBM cancer cell killing by the genetically modified T cell.

* * * * *